US011957045B2

(12) United States Patent
Love et al.

(10) Patent No.: US 11,957,045 B2
(45) Date of Patent: Apr. 9, 2024

(54) METAL COORDINATED PHOTOACTIVE COMPOUNDS FOR TRANSPARENT PHOTOVOLTAIC DEVICES

(71) Applicant: Ubiquitous Energy, Inc., Redwood City, CA (US)

(72) Inventors: John A. Love, Mountain View, CA (US); Vineet Kumar, Fremont, CA (US); Austin Smith, Redwood City, CA (US); Matthew E. Sykes, Chicago, IL (US); Richa Pandey, Sunnyvale, CA (US); Miles C. Barr, Redwood City, CA (US); Ajara A. Safko, Redwood City, CA (US)

(73) Assignee: Ubiquitous Energy, Inc., Redwood City, CA (US)

( * ) Notice: Subject to any disclaimer, the term of this patent is extended or adjusted under 35 U.S.C. 154(b) by 0 days.

(21) Appl. No.: 17/581,689

(22) Filed: Jan. 21, 2022

(65) Prior Publication Data
US 2022/0246869 A1 Aug. 4, 2022

Related U.S. Application Data

(60) Provisional application No. 63/140,733, filed on Jan. 22, 2021.

(51) Int. Cl.
*H10K 85/30* (2023.01)
*C07F 3/06* (2006.01)
(Continued)

(52) U.S. Cl.
CPC ............. *H10K 85/381* (2023.02); *C07F 3/06* (2013.01); *H10K 30/20* (2023.02); *H10K 30/82* (2023.02); *H10K 71/164* (2023.02)

(58) Field of Classification Search
CPC . H01L 51/0092; H01L 51/001; H01L 51/424; H01L 51/442; H10K 85/381; H10K 30/20; H10K 30/82; H10K 71/164
See application file for complete search history.

(56) References Cited

U.S. PATENT DOCUMENTS

2004/0254383 A1 12/2004 Yu et al.
2012/0126213 A1* 5/2012 Gresser .................. H10K 30/00
257/E51.038
(Continued)

FOREIGN PATENT DOCUMENTS

EP 3816168 A1 * 5/2021 ............... C07F 5/02
WO WO-2018186389 A1 * 10/2018 ........... C07D 487/22

OTHER PUBLICATIONS

PCT/US2022/013412, "Invitation to Pay Additional Fees and, Where Applicable, Protest Fee", Mar. 31, 2022, 2 pages.
(Continued)

*Primary Examiner* — Golam Mowla
(74) *Attorney, Agent, or Firm* — Kilpatrick Townsend & Stockton LLP

(57) ABSTRACT

Photoactive compounds are disclosed. The disclosed photoactive compounds include metal complexes with dipyrromethene-based ligands, which can be substituted with a variety of different side chains or groups or can include various fused ring configurations, such as including aromatic or heteroaromatic groups. The metal complexes may include two dipyrromethene-based ligands, which can be the same or different. The photoactive compounds can be used as photoactive materials in organic photovoltaic devices, such as visibly transparent or opaque photovoltaic devices.

20 Claims, 18 Drawing Sheets

(51) Int. Cl.
  *H10K 30/20*  (2023.01)
  *H10K 30/82*  (2023.01)
  *H10K 71/16*  (2023.01)

(56) References Cited

U.S. PATENT DOCUMENTS

2012/0154944 A1  6/2012  Kanna
2020/0035932 A1  1/2020  Yoshioka et al.

OTHER PUBLICATIONS

PCT/US2022/013412, "International Search Report and Written Opinion", dated Jun. 3, 2022, 10 pages.
Sakamoto, et al., "Fluorescent Azadipyrrinato zinc(II) Complex: Hybridisation with a Dipyrrinato Ligand", Dalton Transactions, vol. 41, No. 46, Oct. 2012, pp. 14035-14037.

* cited by examiner

- X, Y, and Z are layer thicknesses:
  - Can be any range
  - Typically between 0 and 300 nm
  - More typically between 0 and 100 nm
- A:B is a blend ratio :
  - Can be any range
  - Typically between 1:20 and 20:1
  - More typically between 1:5 and 5:1

Planar Heterojunction:

Planar-Mixed Heterojunction

Mixed Heterojunction / Bulk Heterojunction / Gradient Heterojunction

METAL COORDINATED PHOTOACTIVE COMPOUNDS FOR TRANSPARENT PHOTOVOLTAIC DEVICES

CROSS-REFERENCE TO RELATED APPLICATIONS

This application claims the benefit of and priority to U.S. Provisional Application No. 63/140,733, filed on Jan. 22, 2021, which is hereby incorporated by reference in its entirety.

FIELD

This application relates generally to the field of optically active materials and devices, and, more particularly, to photoactive materials for use in organic photovoltaic devices, photovoltaic devices, and methods for making photovoltaic devices.

BACKGROUND

The surface area necessary to take advantage of solar energy remains an obstacle to offsetting a significant portion of non-renewable energy consumption. For this reason, low-cost, transparent, organic photovoltaic (OPV) devices that can be integrated onto window panes in homes, skyscrapers, and automobiles are desirable. For example, window glass utilized in automobiles and architecture are typically 70-80% and 55-90% transmissive, respectively, to the visible spectrum, e.g., light with wavelengths from about 450 to 650 nanometers (nm). The limited mechanical flexibility, high module cost and, more importantly, the band-like absorption of inorganic semiconductors limit their potential utility to transparent solar cells.

In contrast, the optical characteristics of organic and molecular semiconductors results in absorption spectra that are highly structured with absorption minima and maxima that are uniquely distinct from the band absorption of their inorganic counterparts. However, a variety of organic and molecular semiconductors exist, but many of exhibit strong absorption in the visible spectrum and thus are not optimal for use in window glass-based photovoltaics.

SUMMARY

Described herein are materials, methods, and systems related to organic photovoltaic devices and, in some cases, especially useful for visibly transparent organic photovoltaic devices as well as partially transparent organic photovoltaic devices and opaque organic photovoltaic devices. More particularly, the present description provides photoactive compounds, such as useful as acceptor molecules or donor molecules, and methods and systems incorporating the disclosed compounds as a photoactive material of a photovoltaic device.

The disclosed photoactive compounds include those comprising a metal chelated dipyrromethene. Example metal chelated dipyrromethenes include metal complexes with a metal having a stable +2 oxidation state, formed with two dipyrromethene ligands, such as in a bidentate structures. In some cases, the ligands are the same as one other, forming a homoleptic structure. In some cases the ligands are different from one other, forming a heteroleptic

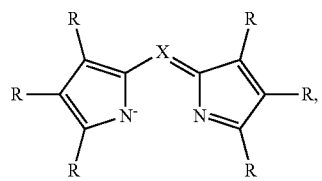

structure. An example dipyrromethene ligand comprises where X is N or C—R. Example metals include Zn, Co, Cu, Ni, Fe, Pb, Mg, Pd, Pt, or Sn.

The dipyrromethene ligands may include various substituents, R. Example R substituents include, but are not limited to, H, F, Cl, Br, I, $CF_3$, CN, a substituted silyl group, a substituted or unsubstituted alkyl group, a substituted or unsubstituted alkenyl group, a substituted or unsubstituted alkynyl group, a substituted or unsubstituted alkoxy group, a substituted or unsubstituted 5-membered ring, a substituted or unsubstituted 5-membered heterocyclic ring, a substituted or unsubstituted 6-membered ring, a substituted or unsubstituted 6-membered heterocyclic ring, or a substituted or unsubstituted 5-6 membered fused rings (e.g., where two R substituents form a ring).

In some examples, the rings of the dipyrromethene ligand may be fused at the alpha or beta positions, with a structure of

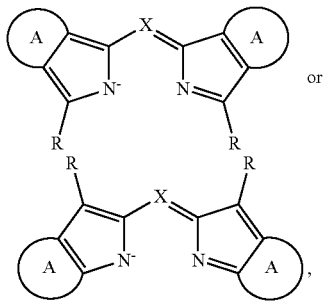

respectively, wherein each A, independently, is a 5-membered ring, a 6-membered ring, or a fused ring group including, but not limited to, aromatic and heteroaromatic moieties. Example substituents for R include, but are not limited to, H, F, Cl, Br, I, $CF_3$, CN, a substituted silyl group, a substituted or unsubstituted alkyl group, a substituted or unsubstituted alkenyl group, a substituted or unsubstituted alkynyl group, a substituted or unsubstituted alkoxy group, a substituted or unsubstituted 5-membered ring, a substituted or unsubstituted 5-membered heterocyclic ring, a substituted or unsubstituted 6-membered ring, a substituted or unsubstituted 6-membered heterocyclic ring, or a substituted or unsubstituted fused ring.

In some examples, two R substituents of a dipyrromethene ligand may form a ring, such as a 5-membered ring, a 6-membered ring, or a fused ring group. In some examples, the dipyrromethene ligand may have a structure of

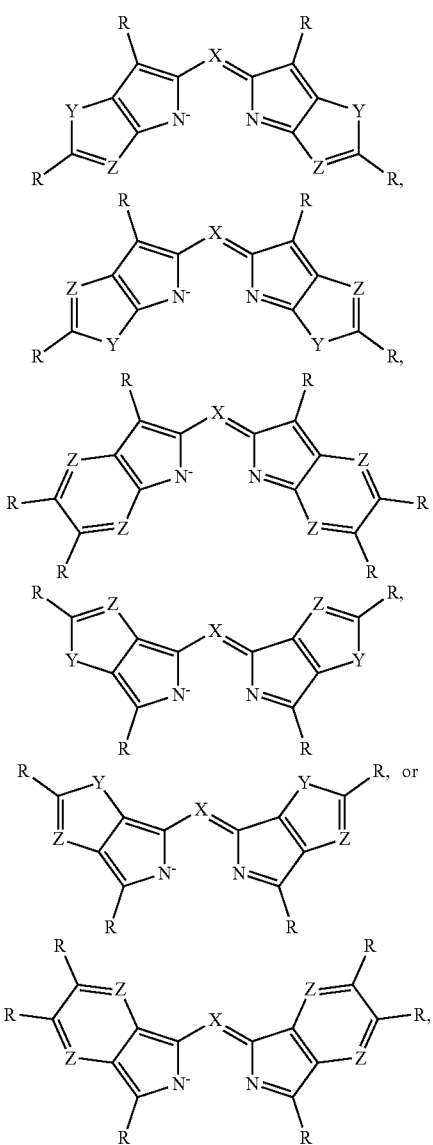

where each Y is independently C—R, O, N, alkyl substituted N, alkyl substituted Si, S, Se, or Te, and each Z is independently C—R or N. In some examples, R may be H, F, Cl, Br, I, $CF_3$, CN, a substituted silyl group, a substituted or unsubstituted alkyl group, a substituted or unsubstituted alkenyl group, a substituted or unsubstituted alkynyl group, a substituted or unsubstituted alkoxy group, a substituted or unsubstituted 5-membered ring, a substituted or unsubstituted 5-membered heterocyclic ring, a substituted or unsubstituted 6-membered ring, a substituted or unsubstituted 6-membered heterocyclic ring, or a substituted or unsubstituted 5-6 membered fused ring.

The photoactive compounds may be suitable for deposition using vacuum deposition techniques like thermal evaporation. In some cases, the molecular weight of the photoactive compounds may impact the volatility of the compounds, as compounds that have a very high molecular weight may end up thermally decomposing before they sublime. In some examples, an upper limit on the molecular weight of a photoactive compound may be about 1500 atomic mass units.

Photovoltaic devices incorporating the photoactive compounds, methods of making the photoactive compounds, and methods of making photovoltaic devices incorporating the photoactive compounds are also described herein.

These and other examples, embodiments, and aspects of the invention along with many of its advantages and features are described in more detail in conjunction with the text below and attached figures.

DETAILED DESCRIPTION

The present disclosure relates to photoactive compounds, which may be useful as electron acceptor compounds or electron donor compounds, photovoltaic devices incorporating the disclosed photoactive compounds as photoactive materials, and methods of making and using photovoltaic devices. The disclosed photoactive compounds may possess properties, such as relatively low molecular weights, relatively high vapor pressures, or the like, that allow for the compounds to be purified and/or deposited using vapor phase techniques such as sublimation, thermal evaporation, and vapor deposition. In addition, the photoactive compounds exhibit strong absorption, allowing for use in organic photovoltaic devices. In some cases, the photoactive compounds exhibit absorption of light more strongly in the near-infrared and/or ultraviolet regions and less strongly in the visible region, permitting their use in visibly transparent photovoltaic devices. In other cases, the photoactive compounds are useful in semi-transparent and opaque photovoltaic devices.

The disclosed photoactive compounds may be useful as electron donors; however, the disclosed photoactive compounds may also be useful as electron acceptors in some cases, depending on the pairing of the photoactive compounds with other compounds in an organic photovoltaic device.

Figure 1:
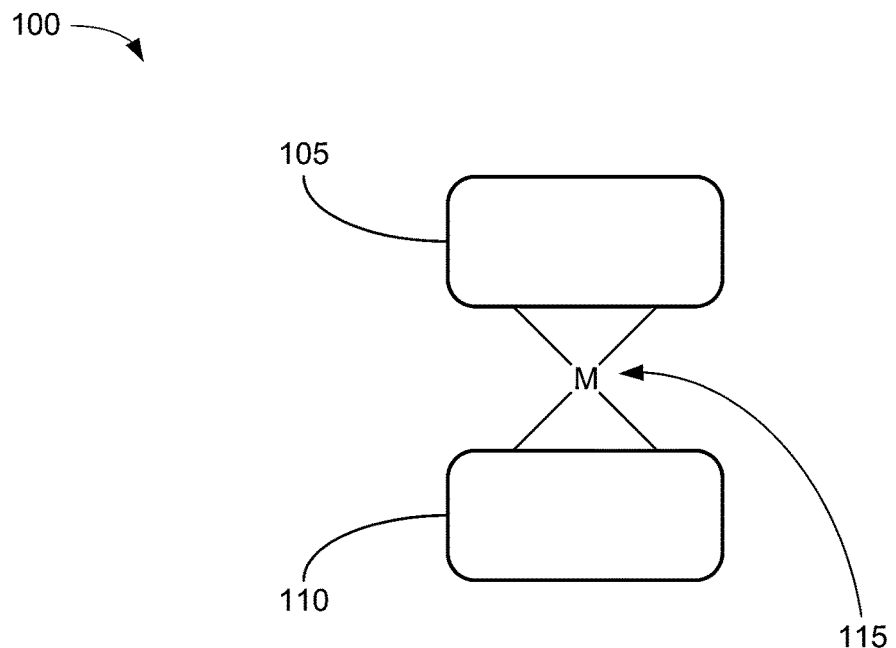
FIG. 1 provides a schematic representation of a photoactive compound in accordance with some examples.

For example, the disclosed compounds may exhibit a bidentate dipyrromethene chelated structure. FIG. 1 provides a schematic representation of a photoactive compound 100 having a bidentate dipyrromethene chelated structure. FIG. 1 shows a first dipyrromethene ligand 105, a second dipyrromethene ligand 110, and a coordinating metal atom 115 between first dipyrromethene ligand 105 and second dipyrromethene ligand 110.

In some cases, first dipyrromethene ligand 105 and second dipyrromethene ligand 110 are identical. Such a configuration may be referred to as a homoleptic compound or structure. In some cases, first dipyrromethene ligand 105 and second dipyrromethene ligand 110 are different. Such a configuration may be referred to as a heteroleptic compound or structure.

Figure 2:
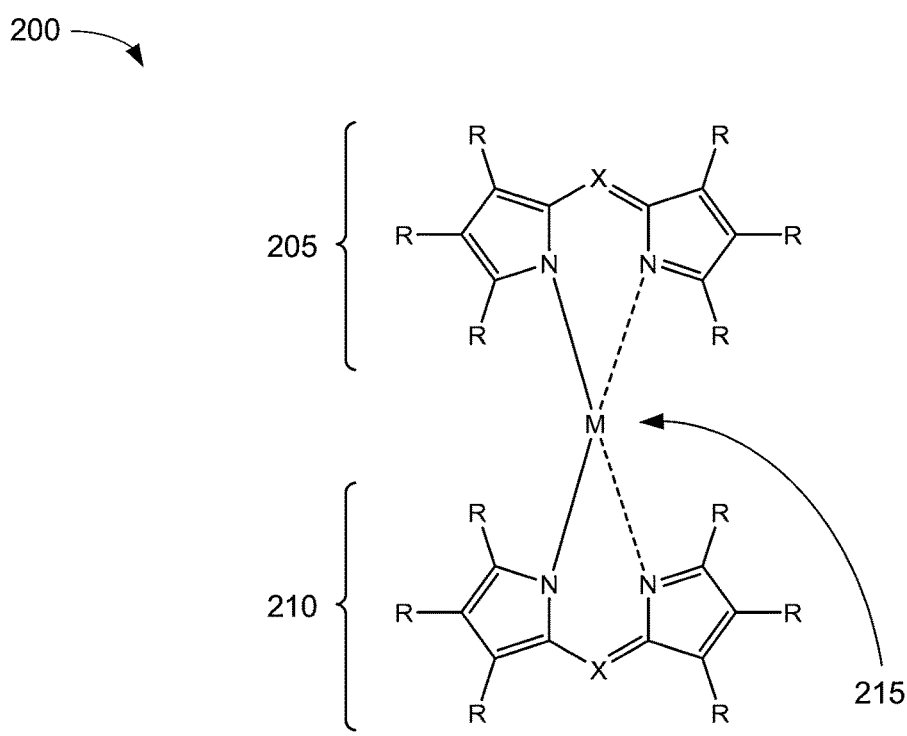
FIG. 2 provides a schematic representation of another photoactive compound in accordance with some examples.

FIG. 2 provides a chemical structure of a photoactive compound 200 having a zinc chelated dipyrromethene structure, where X may comprise N or C—R and where R may comprise any suitable group, such as H, a halogen, or an organic group, optionally including one or more heteroatoms. FIG. 2 shows a similar structural motif as FIG. 1, with photoactive compound 200 comprising a first dipyrromethene ligand 205, a second dipyrromethene ligand 210, and a metal atom 215, which may be Zn or another metal. It will be appreciated that the chemical structure of photoactive compound 200 can be provided herein as an abbreviated structure, such as having a formula of

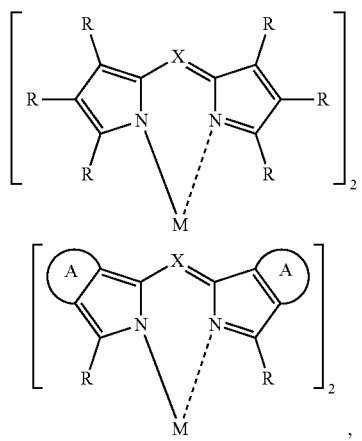

,

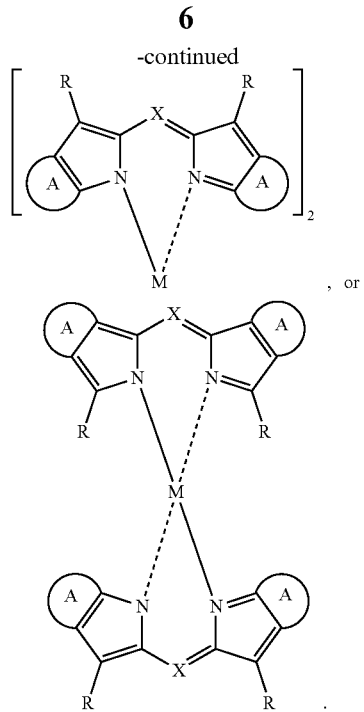

, or

This type of abbreviated structure is used herein to indicate two dipyrromethene ligands are chelated to the metal atom, and may identify homoleptic compounds as well as heteroleptic compounds, such as when generic structures (e.g., containing one or more R groups) are used. Further details and examples of the disclosed photoactive compounds are described below.

In some examples, for purification and use of the disclosed photoactive compounds, a very high molecular weight may be undesirable, such as about 1500 amu or higher, about 1450 amu or higher, about 1400 amu or higher, about 1350 amu or higher, about 1300 amu or higher, about 1250 amu or higher, about 1200 amu or higher, about 1150 amu or higher, about 1100 amu or higher, about 1050 amu or higher, about 1000 amu or higher, about 950 amu or higher, about 900 amu or higher, or between 900 amu and 2000 amu or a subrange thereof. Some compounds with very high molecular weights may have limited volatilities and useful methods of purifying and using photoactive compounds may employ an evaporation or sublimation-based method. In addition, the photoactive compounds may be deposited as part of a photovoltaic device using a thermal evaporation technique and compounds of very high molecular weight may be difficult to deposit using thermal evaporation. In various examples, the photoactive compounds described herein have a molecular weight of 200 amu to 1500 amu, less than or about 1450 amu, less than or about 1400 amu, less than or about 1350 amu, less than or about 1300 amu, less than or about 1250 amu, less than or about 1200 amu, less than or about 1150 amu, less than or about 1100 amu, less than or about 1050 amu, less than or about 1000 amu, less than or about 950 amu, less than or about 900 amu, less than or about 850 amu, less than or about 800 amu, less than or about 750 amu, less than or about 700 amu, less than or about 650 amu, less than or about 600 amu, less than or about 550 amu, less than or about 500 amu, less than or about 450 amu, less than or about 400 amu, less than or about 350 amu, less than or about 300 amu, less than or about 250 amu, or less than or about 200 amu.

To achieve desired optical properties, photoactive compounds may exhibit a molecular electronic structure where photons of light are absorbed, which results in promotion of an electron to a higher molecular orbital, with an energy difference matching that of the absorbed photon, which may result in generation of an electron-hole pair or exciton, which can subsequently separate into distinct electrons and holes, such as at an interface with another material. Compounds exhibiting extended aromaticity or extended conjugation may be beneficial, as compounds with extended aromaticity or extended conjugation may exhibit electronic absorption with energies matching that of near-infrared, visible, and/or ultraviolet photons. In addition to conjugation and aromaticity, absorption features may be modulated by inclusion of heteroatoms in the organic structure of the visibly transparent photoactive compounds, such as oxygen, nitrogen, or sulfur atoms. When a metal atom is included in the photoactive compounds, the identity of the metal atom may also impact the absorption energy.

In general the terms and phrases used herein have their art-recognized meaning, which can be found by reference to standard texts, journal references and contexts known to those skilled in the art. The following definitions are provided to clarify their specific use in the context of the invention.

As used herein, "maximum absorption strength" refers to the largest absorption value in a particular spectral region, such as the ultraviolet band (e.g., from 200 nm to 450 nm or from 280 nm to 450 nm), the visible band (e.g., from 450 nm to 650 nm), or the near-infrared band (e.g., from 650 nm to 1400 nm), of a particular molecule, for example. In some examples, a maximum absorption strength may correspond to an absorption strength of an absorption feature that is a local or absolute maximum, such as an absorption band or peak, and may be referred to as a peak absorption. In some examples, a maximum absorption strength in a particular band may not correspond to a local or absolute maximum but may instead correspond to the largest absorption value in the particular band. Such a configuration may occur, for example, when an absorption feature spans multiple bands (e.g., visible and near-infrared), and the absorption values from the absorption feature that occur within one band are smaller than those occurring within the adjacent band, such as when the peak of the absorption feature is located within the near-infrared band but a tail of the absorption feature extends to the visible band. In some examples, a photoactive compound described herein may having an absorption peak at a wavelength greater than about 650 nanometers (i.e., in the near-infrared), and the photoactive compound's absorption peak may be greater in magnitude than the photoactive compound's absorption at any wavelength between about 450 and 650 nanometers.

In an example, disclosed compositions or compounds are isolated or purified. In an example, an isolated or purified compound is at least partially isolated or purified as would be understood in the art. In an example, a disclosed composition or compound has a chemical purity of 80%, optionally for some applications 90%, optionally for some applications 95%, optionally for some applications 99%, optionally for some applications 99.9%, optionally for some applications 99.99%, and optionally for some applications 99.999% pure. Purification of the disclosed compositions or compounds may be performed using any desirable technique. Purification by sublimation and crystallization (e.g., vacuum sublimation) may be a particularly useful technique.

Compounds disclosed herein optionally contain one or more ionizable groups. Ionizable groups include groups from which a proton can be removed (e.g., —COOH) or added (e.g., amines) and groups which can be quaternized (e.g., amines). All possible ionic forms of such molecules and salts thereof are intended to be included individually in the disclosure herein. With regard to salts of the compounds described herein, it will be appreciated that a wide variety of available counter-ions may be selected that are appropriate for preparation of salts for a given application. In specific applications, the selection of a given anion or cation for preparation of a salt can result in increased or decreased solubility of that salt.

The disclosed compounds optionally contain one or more chiral centers. Accordingly, this disclosure includes racemic mixtures, diastereomers, enantiomers, tautomers and mixtures enriched in one or more stereoisomer. Disclosed compounds including chiral centers encompass the racemic forms of the compound as well as the individual enantiomers and non-racemic mixtures thereof.

As used herein, the terms "group" and "moiety" may refer to a functional group of a chemical compound. Groups of the disclosed compounds refer to an atom or a collection of atoms that are a part of the compound. Groups of the disclosed compounds may be attached to other atoms of the compound via one or more covalent bonds. Groups may also be characterized with respect to their valence state. The present disclosure includes groups characterized as monovalent, divalent, trivalent, etc. valence states. In examples, the term "substituent" may be used interchangeably with the terms "group" and "moiety." Groups may also be characterized with respect to their ability to donate or receive an electron, and such characterization may, in some examples, refer to a relative character of the group to donate or receive an electron as compared to other groups.

As is customary and well known in the art, hydrogen atoms in chemical formulas disclosed herein are not always explicitly shown, for example, hydrogen atoms bonded to the carbon atoms of aliphatic, aromatic, alicyclic, carbocyclic, and/or heterocyclic rings are not always explicitly shown in the formulas recited. The structures provided herein, for example in the context of the description of any specific formulas and structures recited, are intended to convey the chemical composition of disclosed compounds of methods and compositions. It will be appreciated that the structures provided do not indicate the specific positions of atoms and bond angles between atoms of these compounds.

As used herein, the terms "alkylene" and "alkylene group" are used synonymously and refer to a divalent group derived from an alkyl group as defined herein. The present disclosure includes compounds having one or more alkylene groups. Alkylene groups in some compounds function as attaching and/or spacer groups. Disclosed compounds optionally include substituted and/or unsubstituted $C_1$-$C_{20}$ alkylene, $C_1$-$C_{10}$ alkylene and $C_1$-$C_5$ alkylene groups.

As used herein, the terms "cycloalkylene" and "cycloalkylene group" are used synonymously and refer to a divalent group derived from a cycloalkyl group as defined herein. The present disclosure includes compounds having one or more cycloalkylene groups. Cycloalkyl groups in some compounds function as attaching and/or spacer groups. Disclosed compounds optionally include substituted and/or unsubstituted $C_3$-$C_{20}$ cycloalkylene, $C_3$-$C_{10}$ cycloalkylene and $C_3$-$C_5$ cycloalkylene groups.

As used herein, the terms "arylene" and "arylene group" are used synonymously and refer to a divalent group derived from an aryl group as defined herein. The present disclosure includes compounds having one or more arylene groups. In some examples, an arylene is a divalent group derived from an aryl group by removal of hydrogen atoms from two intra-ring carbon atoms of an aromatic ring of the aryl group. Arylene groups in some compounds function as attaching and/or spacer groups. Arylene groups in some compounds function as chromophore, fluorophore, aromatic antenna, dye, and/or imaging groups. Disclosed compounds optionally include substituted and/or unsubstituted $C_5$-$C_{30}$ arylene, $C_5$-$C_{20}$ arylene, $C_5$-$C_{10}$ arylene, and $C_1$-$C_5$ arylene groups.

As used herein, the terms "heteroarylene" and "heteroarylene group" are used synonymously and refer to a divalent group derived from a heteroaryl group as defined herein. The present disclosure includes compounds having one or more heteroarylene groups. In some examples, a heteroarylene is a divalent group derived from a heteroaryl group by removal of hydrogen atoms from two intra-ring carbon atoms or intra-ring nitrogen atoms of a heteroaromatic or aromatic ring of the heteroaryl group. Heteroarylene groups in some compounds function as attaching and/or spacer groups. Heteroarylene groups in some compounds function as chromophore, aromatic antenna, fluorophore, dye, and/or imaging groups. Disclosed compounds optionally include substituted and/or unsubstituted $C_5$-$C_{30}$ heteroarylene, $C_5$-$C_{20}$ heteroarylene, $C_5$-$C_{10}$ heteroarylene, and $C_1$-$C_5$ heteroarylene groups.

As used herein, the terms "alkenylene" and "alkenylene group" are used synonymously and refer to a divalent group derived from an alkenyl group as defined herein. The present disclosure includes compounds having one or more alkenylene groups. Alkenylene groups in some compounds function as attaching and/or spacer groups. Disclosed compounds optionally include substituted and/or unsubstituted $C_2$-$C_{20}$ alkenylene, $C_2$-$C_{10}$ alkenylene and $C_2$-$C_5$ alkenylene groups.

As used herein, the terms "cylcoalkenylene" and "cylcoalkenylene group" are used synonymously and refer to a divalent group derived from a cylcoalkenyl group as defined herein. The present disclosure includes compounds having one or more cylcoalkenylene groups. Cycloalkenylene groups in some compounds function as attaching and/or spacer groups. Disclosed compounds optionally include substituted and/or unsubstituted $C_3$-$C_{20}$ cylcoalkenylene, $C_3$-$C_{10}$ cylcoalkenylene and $C_3$-$C_5$ cylcoalkenylene groups.

As used herein, the terms "alkynylene" and "alkynylene group" are used synonymously and refer to a divalent group derived from an alkynyl group as defined herein. The present disclosure includes compounds having one or more alkynylene groups. Alkynylene groups in some compounds function as attaching and/or spacer groups. Disclosed compounds optionally include substituted and/or unsubstituted $C_2$-$C_{20}$ alkynylene, $C_2$-$C_{10}$ alkynylene and $C_2$-$C_5$ alkynylene groups.

As used herein, the term "halo" refers to a halogen group, such as a fluoro (—F), chloro (—Cl), bromo (—Br), or iodo (—I).

The term "heterocyclic" refers to ring structures containing at least one other kind of atom, in addition to carbon, in the ring. Examples of such atoms include oxygen, sulfur, selenium, tellurium, nitrogen, phosphorus, silicon, germanium, boron, aluminum, and, in some cases, a transition metal. Examples of heterocyclic rings include, but are not limited to, pyrrolidinyl, piperidyl, imidazolidinyl, tetrahydrofuranyl, tetrahydrothienyl, furanyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl, and tetrazolyl groups. Atoms of heterocyclic rings can be bonded to a wide range of other atoms and functional groups, for example, provided as substituents. Heterocyclic rings include aromatic heterocycles and non-aromatic heterocycles.

The term "carbocyclic" refers to ring structures containing only carbon atoms in the ring. Carbon atoms of carbocyclic rings can be bonded to a wide range of other atoms and functional groups, for example, provided as substituents. Carbocyclic rings include aromatic carbocyclic rings and non-aromatic carbocyclic rings.

The term "alicyclic" refers to a ring that is not an aromatic ring. Alicyclic rings include both carbocyclic and heterocyclic rings.

The term "aliphatic" refers to non-aromatic hydrocarbon compounds and groups. Aliphatic groups generally include carbon atoms covalently bonded to one or more other atoms, such as carbon and hydrogen atoms. Aliphatic groups may, however, include a non-carbon atom, such as an oxygen atom, a nitrogen atom, a sulfur atom, etc., in place of a carbon atom. Non-substituted aliphatic groups include only hydrogen substituents. Substituted aliphatic groups include non-hydrogen substituents, such as halo groups and other substituents described herein. Aliphatic groups can be straight chain, branched, or cyclic. Aliphatic groups can be saturated, meaning only single bonds join adjacent carbon (or other) atoms. Aliphatic groups can be unsaturated, meaning one or more double bonds or triple bonds join adjacent carbon (or other) atoms.

Alkyl groups include straight-chain, branched, and cyclic alkyl groups. Alkyl groups include those having from 1 to 30 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. The term cycloalkyl specifically refers to an alky group having a ring structure such as ring structure comprising 3-30 carbon atoms, optionally 3-20 carbon atoms and optionally 3-10 carbon atoms, including an alkyl group having one or more rings. Cycloalkyl groups include those having a 3-, 4-, 5-, 6-, 7-, 8-, 9-, or 10-member carbon ring(s) and particularly those having a 3-, 4-, 5-, 6-, or 7-member ring(s). The carbon rings in cycloalkyl groups can also carry alkyl groups. Cycloalkyl groups can include bicyclic and tricycloalkyl groups. Alkyl groups are optionally substituted. Substituted alkyl groups include, among others, those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully-halogenated or semi-halogenated alkyl groups, such as alkyl groups having one or more hydrogens replaced with one or more fluorine atoms, chlorine atoms, bromine atoms and/or iodine atoms. Substituted alkyl groups include fully-fluorinated or semi-fluorinated alkyl groups, such as alkyl groups having one or more hydrogens replaced with one or more fluorine atoms.

An alkoxy group is an alkyl group that has been modified by linkage to oxygen and can be represented by the formula R—O and can also be referred to as an alkyl ether group. Examples of alkoxy groups include, but are not limited to, methoxy, ethoxy, propoxy, butoxy, and heptoxy. Alkoxy groups include substituted alkoxy groups wherein the alkyl portion of the groups is substituted as provided herein in connection with the description of alkyl groups. As used herein MeO— refers to $CH_3O$—.

Alkenyl groups include straight-chain, branched, and cyclic alkenyl groups. Alkenyl groups include those having 1, 2, or more double bonds and those in which two or more of the double bonds are conjugated double bonds. Alkenyl groups include those having from 2 to 20 carbon atoms. Alkenyl groups include small alkenyl groups having 2 to 4 carbon atoms. Alkenyl groups include medium length alkenyl groups having from 5-10 carbon atoms. Alkenyl groups include long alkenyl groups having more than 10 carbon atoms, particularly those having 10-20 carbon atoms. Cycloalkenyl groups include those in which a double bond is in the ring or in an alkenyl group attached to a ring. The term cycloalkenyl specifically refers to an alkenyl group having a ring structure, including an alkenyl group having a 3-, 4-, 5-, 6-, 7-, 8-, 9-, or 10-member carbon ring(s) and particularly those having a 3-, 4-, 5-, 6-, or 7-member ring(s). The carbon rings in cycloalkenyl groups can also carry alkyl groups. Cycloalkenyl groups can include bicyclic and tricyclic alkenyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully-halogenated or semi-halogenated alkenyl groups, such as alkenyl groups having one or more hydrogens replaced with one or more fluorine atoms, chlorine atoms, bromine atoms, and/or iodine atoms. Substituted alkenyl groups include fully-fluorinated or semi-fluorinated alkenyl groups, such as alkenyl groups having one or more hydrogen atoms replaced with one or more fluorine atoms.

Aryl groups include groups having one or more 5-, 6- or 7-member aromatic and/or heterocyclic aromatic rings. The term heteroaryl specifically refers to aryl groups having at least one 5-, 6-, or 7-member heterocyclic aromatic rings. Aryl groups can contain one or more fused aromatic and heteroaromatic rings or a combination of one or more aromatic or heteroaromatic rings and one or more non-aromatic rings that may be fused or linked via covalent bonds. Heterocyclic aromatic rings can include one or more N, O, or S atoms in the ring, among others. Heterocyclic aromatic rings can include those with one, two or three N atoms, those with one or two O atoms, and those with one or two S atoms, or combinations of one or two or three N, O, or S atoms, among others. Aryl groups are optionally substituted. Substituted aryl groups include among others those which are substituted with alkyl or alkenyl groups, which groups in turn can be optionally substituted. Specific aryl groups include phenyl, biphenyl groups, pyrrolidinyl, imidazolidinyl, tetrahydrofuranyl, tetrahydrothienyl, furanyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semi-fluorinated aryl groups, such as aryl groups having one or more hydrogens replaced with one or more fluorine atoms. Aryl groups include, but are not limited to, aromatic group-containing or heterocyclic aromatic group-containing groups corresponding to any one of the following: benzene, naphthalene, naphthoquinone, diphenylmethane, fluorene, anthracene, anthraquinone, phenanthrene, tetracene, tetracenedione, pyridine, quinoline, isoquinoline, indoles, isoindole, pyrrole, imidazole, oxazole, thiazole, pyrazole, pyrazine, pyrimidine, purine, benzimidazole, furan, benzofuran, dibenzofuran, carbazole, acridine, acridone, phenanthridine, thiophene, benzothiophene, dibenzothiophene, xanthene, xanthone, flavone, coumarin, azulene, or anthracycline. As used herein, a group corresponding to the groups listed above expressly includes an aromatic or heterocyclic aromatic group, including monovalent, divalent and polyvalent groups, of the aromatic and heterocyclic aromatic groups listed herein are provided in a covalently bonded configuration in the disclosed compounds at any suitable point of attachment. In examples, aryl groups contain between 5 and 30 carbon atoms. In examples, aryl groups contain one aromatic or heteroaromatic six-membered ring and one or more additional five- or six-membered aromatic or heteroaromatic ring. In examples, aryl groups contain between five and eighteen carbon atoms in the rings. Aryl groups optionally have one or more aromatic rings or heterocyclic aromatic rings having one or more electron donating groups, electron withdrawing groups and/or targeting ligands provided as substituents.

Arylalkyl and alkylaryl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl and arylalkyl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully-halogenated or semi-halogenated arylalkyl groups, such as arylalkyl groups having one or more alkyl and/or aryl groups having one or more hydrogens replaced with one or more fluorine atoms, chlorine atoms, bromine atoms, and/or iodine atoms.

As to any of the groups described herein which contain one or more substituents, it is understood that such groups do not contain any substitution or substitution patterns which are sterically impractical and/or synthetically non-feasible. In addition, the disclosed compounds include all stereochemical isomers arising from the substitution of these compounds. Optional substitution of alkyl groups includes substitution with one or more alkenyl groups, aryl groups, or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for any alkyl, alkenyl and aryl group includes substitution with one or more of the following substituents, among others:
 halogen, including fluorine, chlorine, bromine, or iodine;
 pseudohalides, including —CN;
 —COOR where R is a hydrogen or an alkyl group or an aryl group or, more specifically, where R is a methyl, ethyl, propyl, butyl, or phenyl group, all of which are optionally substituted;

—COR where R is a hydrogen or an alkyl group or an aryl group or, more specifically, where R is a methyl, ethyl, propyl, butyl, or phenyl group, all of which are optionally substituted;

—CON(R)$_2$ where each R, independently of each other R, is a hydrogen or an alkyl group or an aryl group or, more specifically, where R is a methyl, ethyl, propyl, butyl, or phenyl group, all of which are optionally substituted; and where R and R can optionally form a ring which can contain one or more double bonds and can contain one or more additional carbon atoms;

—OCON(R)$_2$ where each R, independently of each other R, is a hydrogen or an alkyl group or an aryl group and, more specifically, where R is a methyl, ethyl, propyl, butyl, or phenyl group, all of which are optionally substituted; and where R and R can optionally form a ring which can contain one or more double bonds and can contain one or more additional carbon atoms;

—N(R)$_2$ where each R, independently of each other R, is a hydrogen, or an alkyl group, or an acyl group or an aryl group or, more specifically, where R is a methyl, ethyl, propyl, butyl, phenyl, or acetyl group, all of which are optionally substituted; and where R and R can optionally form a ring which can contain one or more double bonds and can contain one or more additional carbon atoms;

—SR, where R is hydrogen or an alkyl group or an aryl group or, more specifically, where R is hydrogen, methyl, ethyl, propyl, butyl, or a phenyl group, all of which are optionally substituted;

—SO$_2$R, or —SOR where R is an alkyl group or an aryl group or, more specifically, where R is a methyl, ethyl, propyl, butyl, or phenyl group, all of which are optionally substituted;

—OCOOR where R is an alkyl group or an aryl group;

—SO$_2$N(R)$_2$ where each R, independently of each other R, is a hydrogen, an alkyl group, or an aryl group, all of which are optionally substituted, and wherein R and R can optionally form a ring which can contain one or more double bonds and can contain one or more additional carbon atoms;

—OR where R is H, an alkyl group, an aryl group, or an acyl group, all of which are optionally substituted. In a particular example R can be an acyl, yielding —OCOR" where R" is a hydrogen or an alkyl group or an aryl group and more specifically where R" is methyl, ethyl, propyl, butyl, or phenyl groups, all of which are optionally substituted.

Specific substituted alkyl groups include haloalkyl groups, particularly trihalomethyl groups and specifically trifluoromethyl groups. Specific substituted aryl groups include mono-, di-, tri, tetra- and penta-halo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups; and methoxyphenyl groups, particularly 4-methoxyphenyl groups.

The term "electron acceptor" refers to a chemical composition that can accept an electron from another structure or compound. The term electron acceptor may be used, in some cases, in a relative sense to identify a characteristic of a compound or a subgroup thereof as having a stronger affinity for receiving an additional electron as compared to another compound or a subgroup. In an organic photovoltaic, an electron acceptor may be a compound having an ability to receive electrons from an electron donor. An electron acceptor may be a photoactive compound that generates an electron-hole pair (exciton) upon photoabsorption of light and which can transfer generated holes to an electron donor.

The term "electron donor" refers to a chemical composition that can donate an electron to another structure or compound. The term electron donor may be used, in some cases, in a relative sense to identify a characteristic of a compound or a subgroup thereof as having a weaker affinity for receiving an additional electron as compared to another compound or a subgroup. In an organic photovoltaic, an electron donor may be a compound having an ability to transfer electrons to an electron acceptor. An electron donor may be a photoactive compound that generates an electron-hole pair (exciton) upon photoabsorption of light and which can transfer generated electrons to an electron acceptor.

As used herein, the terms visible transparency, visibly transparent, and the like refer to an optical property of a material that exhibits an overall absorption, average absorption, or maximum absorption in the visible band of 0%-70%, such as less than or about 70%, less than or about 65%, less than or about 60%, less than or about 55%, less than or about 50%, less than or about 45%, less than or about 40%, less than or about 35%, less than or about 30%, less than or about 25%, or less than or about 20%. Stated another way, visibly transparent materials may transmit 30%-100% of incident visible light, such as greater than or about 80% of incident visible light, greater than or about 75% of incident visible light, greater than or about 70% of incident visible light, greater than or about 65% of incident visible light, greater than or about 60% of incident visible light, greater than or about 55% of incident visible light, greater than or about 50% of incident visible light, greater than or about 45% of incident visible light, greater than or about 40% of incident visible light, greater than or about 35% of incident visible light, or greater than or about 30% of incident visible light. Visibly transparent materials are generally considered at least partially see-through (i.e., not completely opaque) when viewed by a human. Optionally, visibly transparent materials may be colorless (i.e., not exhibit strong visible absorption features that would provide an appearance of a particular color) when viewed by a human.

As used herein, the term "visible" refers to a band of electromagnetic radiation for which the human eye is sensitive. For example, visible light may refer to light having wavelengths between about 450 nm and about 650 nm.

The term "near-infrared" or "NIR" refers to a band of electromagnetic radiation having wavelengths longer than those for which the human eye is sensitive. For example, near-infrared light may refer to light having wavelengths greater than 650 nm, such as between about 650 nm and about 1400 nm or between about 650 nm and 2000 nm.

The term "ultraviolet" or "UV" refers to a band of electromagnetic radiation having wavelengths shorter than those for which the human eye is sensitive. For example, ultraviolet light may refer to light having wavelengths less than 450 nm, such as between about 200 nm and about 450 nm or between about 280 nm and 450 nm.

Figure 3A:
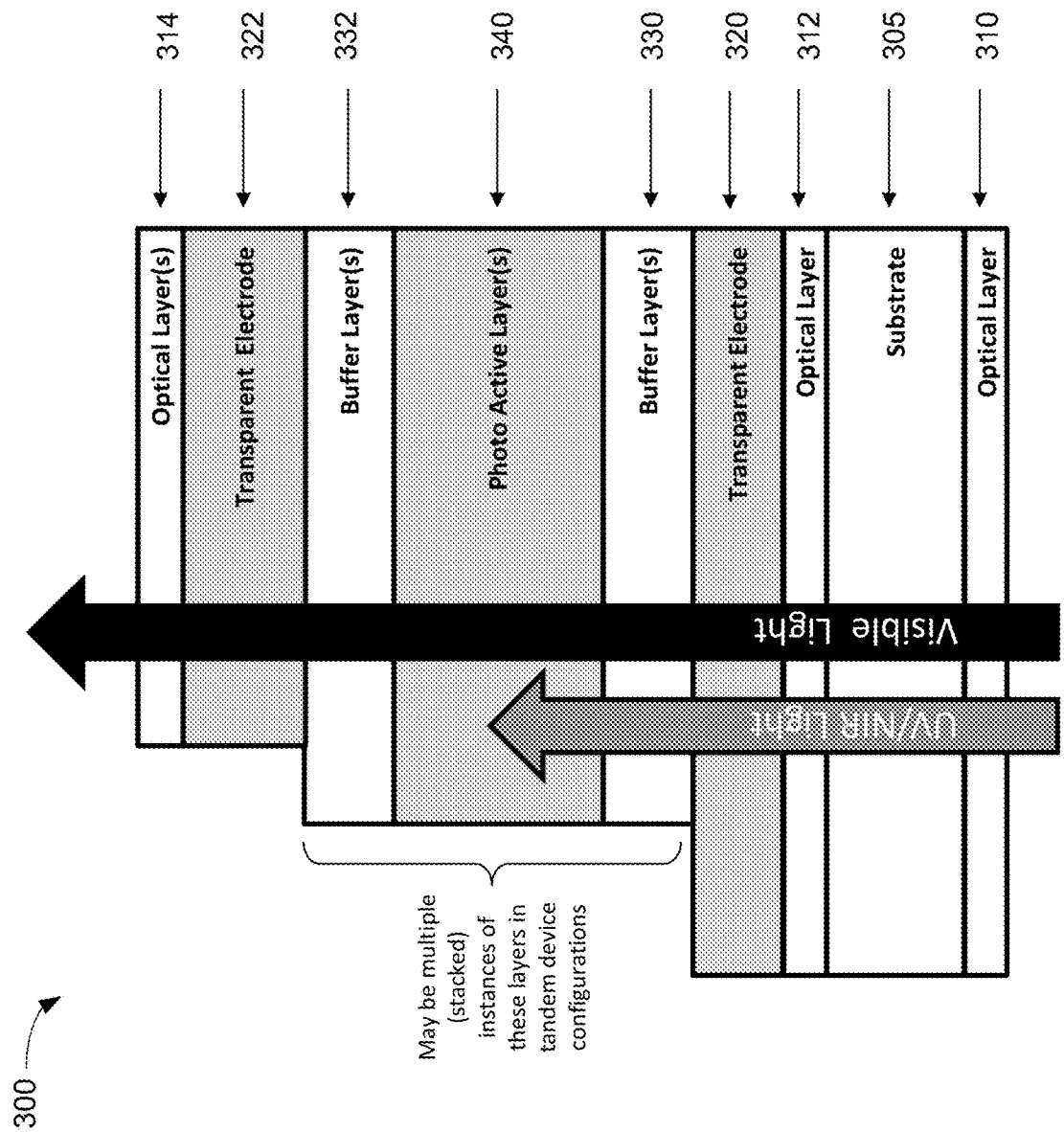
FIG. 3A is a simplified schematic diagram illustrating a visibly transparent photovoltaic device according to some examples.

The disclosed compounds can be used in any application, though the specific application described herein is for use as photoactive compounds in an organic photovoltaic device, such as electron acceptor compounds or electron donor compounds. In some examples, the disclosed compounds are paired with a counterpart photoactive material (e.g., an electron donor material or an electron acceptor material) to form heterojunction structures comprising an electron donor compound and a counterpart electron acceptor material or comprising an electron acceptor compound and a counterpart electron donor material, as further described below, for use in generating and separating electron-hole pairs for converting electromagnetic radiation (e.g., ultraviolet light, visible light, and/or near-infrared light) into useful electrical energy (e.g., voltage/current). In a specific example, the photovoltaic device incorporating one or more of the disclosed photoactive compounds is a visibly transparent photovoltaic device. In other examples, the photovoltaic device incorporating one or more of the disclosed photoactive compounds is a partially transparent photovoltaic device, a colored partially transparent photovoltaic device, or an opaque photovoltaic device FIG. 3A is a simplified schematic diagram illustrating a photovoltaic device according to some examples. As illustrated in FIG. 3A, the photovoltaic device 300 includes a number of layers and elements discussed more fully below. As discussed in relation to FIG. 4, the photovoltaic device 300 may be visibly transparent, which indicates that the photovoltaic device absorbs optical energy at wavelengths outside the visible wavelength band of 450 nm to 650 nm, for example, while substantially transmitting visible light inside the visible wavelength band. As illustrated in FIG. 3A, UV and/or NIR light is absorbed in the layers and elements of the photovoltaic device while visible light is transmitted through the device, though in some cases, such as in a partially transparent photovoltaic device or an opaque photovoltaic device, visible light may be absorbed, such as by a photoactive layer.

Substrate 305, which can be glass or other visibly transparent materials providing sufficient mechanical support to the other layers and structures illustrated, supports optical layers 310 and 312. These optical layers can provide a variety of optical properties, including antireflection (AR) properties, wavelength selective reflection or distributed Bragg reflection properties, index matching properties, encapsulation, or the like. Optical layers may advantageously be visibly transparent. An additional optical layer 314 can be utilized, for example, as an AR coating, an index matching later, a passive infrared or ultraviolet absorption layer, etc. Optionally, optical layers may be transparent to ultraviolet and/or near-infrared light or transparent to at least a subset of wavelengths in the ultraviolet and/or near-infrared bands. Depending on the configuration, additional optical layer 314 may also be a passive visible absorption layer or a neutral filter, for example. Example substrate materials include various glasses and rigid or flexible polymers. Multilayer substrates may also be utilized. Substrates may have any suitable thickness to provide the mechanical support needed for the other layers and structures, such as, for example, thicknesses from 1 mm to 20 mm. In some cases, the substrate may be or comprise an adhesive film to allow application of the photovoltaic device 300 to another structure, such as a window pane, display device, etc.

It will be appreciated that, although some of devices described herein exhibit visible transparency, photovoltaic devices are also disclosed herein that are not fully visibly transparent, as some of the photoactive compounds described herein may exhibit visible absorption. In the case of a visibly transparent photovoltaic device that overall exhibits visible transparency, such as a transparency in the 450-650 nm range greater than 30%, greater than 40%, greater than 50%, greater than 60%, greater than 70%, or up to or approaching 100%, certain materials taken individually may exhibit absorption in portions of the visible spectrum. Optionally, each individual material or layer in a visibly transparent photovoltaic device has a high transparency in the visible range, such as greater than 30% (i.e., between 30% and 100%). It will be appreciated that transmission or absorption may be expressed as a percentage and may be dependent on the material's absorbance properties, a thickness or path length through an absorbing material, and a concentration of the absorbing material, such that a material with an absorbance in the visible spectral region may still exhibit a low absorption or high transmission if the path length through the absorbing material is short and/or the absorbing material is present in low concentration.

As described herein and below, various photoactive materials in various photoactive layers advantageously can exhibit minimal absorption in the visible region (e.g., less than 20%, less than 30%, less than 40%, less than 50%, less than 60%, or less than 70%), and instead exhibit high absorption in the near-infrared and/or ultraviolet regions (e.g., an absorption peak of greater than 50%, greater than 60%, greater than 70%, or greater than 80%). For some applications, absorption in the visible region may be as large as 70%. Various configurations of other materials, such as the substrate, optical layers, and buffer layers, may be useful for allowing these materials to provide overall visible transparency, even though the materials may exhibit some amount of visible absorption. For example, a thin film of a metal may be included in a transparent electrode, such as a metal that exhibits visible absorption, like Ag or Cu; when provided in a thin film configuration, however, the overall transparency of the film may be high. Similarly, materials included in an optical or buffer layer may exhibit absorption in the visible range, but may be provided at a concentration or thickness where the overall amount of visible light absorption is low, providing visible transparency.

The photovoltaic device 300 also includes a set of transparent electrodes 320 and 322 with a photoactive layer 340 positioned between electrodes 320 and 322. These electrodes, which can be fabricated using ITO, thin metal films, or other suitable visibly transparent materials, provide electrical connection to one or more of the various layers illustrated. For example, thin films of copper, silver, or other metals may be suitable for use as a visibly transparent electrode, even though these metals may absorb light in the visible band. When provided as a thin film, however, such as a film having a thickness of 1 nm to 200 nm (e.g., about 5 nm, about 10 nm, about 15 nm, about 20 nm, about 25 nm, about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, about 95 nm, about 100 nm, about 105 nm, about 110 nm, about 115 nm, about 120 nm, about 125 nm, about 130 nm, about 135 nm, about 140 nm, about 145 nm, about 150 nm, about 155 nm, about 160 nm, about 165 nm, about 170 nm, about 175 nm, about 180 nm, about 185 nm, about 190 nm, or about 195 nm), an overall transmittance of the thin film in the visible band may remain high, such as greater than 30%, greater than 40%, greater than 50%, greater than 60%, greater than 70%, greater than 80%, or greater than 90%. Advantageously, thin metal films, when used as transparent electrodes, may exhibit lower absorption in the ultraviolet band than other semiconducting materials that may be useful as a transparent electrode, such as ITO, as some semiconducting transparent conducting oxides exhibit a band gap that occurs in the ultraviolet band and thus are highly absorbing or opaque to ultraviolet light. In some cases, however, an ultraviolet absorbing transparent electrode may be used, such as to screen at least a portion of the ultraviolet light from underlying components, as ultraviolet light may degrade certain materials.

A variety of deposition techniques may be used to generate a transparent electrode, including vacuum deposition techniques, such as atomic layer deposition, chemical vapor deposition, physical vapor deposition, thermal evaporation, sputter deposition, epitaxy, etc. Solution based deposition techniques, such as spin-coating, may also be used in some cases. In addition, various components, such as transparent electrodes, may be patterned using techniques known in the art of microfabrication, including lithography, lift off, etching, etc.

Buffer layers 330 and 332 and photoactive layer 340 are utilized to implement the electrical and optical properties of the photovoltaic device. These layers can be layers of a single material or can include multiple sub-layers as appropriate to the particular application. Thus, the term "layer" is not intended to denote a single layer of a single material, but can include multiple sub-layers of the same or different materials. In some cases, layers may partially or completely overlap. In some examples, buffer layer 330, photoactive layer(s) 340 and buffer layer 332 are repeated in a stacked configuration to provide tandem device configurations, such as including multiple heterojunctions. In some examples, the photoactive layer(s) include electron donor materials and electron acceptor materials, also referred to as donors and acceptors. These donors and acceptors can, in some cases, be visibly transparent, but absorb outside the visible wavelength band to provide the photoactive properties of the device. In the case of partially transparent and opaque photovoltaic devices, the donors and/or acceptors can absorb in the visible region.

Useful buffer layers include those that function as electron transport layers, electron blocking layers, hole transport layers, hole blocking layers, exciton blocking layers, optical spacers, physical buffer layers, charge recombination layers, or charge generation layers. Buffer layers may exhibit any suitable thickness to provide the buffering effect desired and may optionally be present or absent. Useful buffer layers, when present, may have thicknesses from 1 nm to 1 µm. Various materials may be used as buffer layers, including fullerene materials, carbon nanotube materials, graphene materials, metal oxides, such as molybdenum oxide, titanium oxide, zinc oxide, etc., polymers, such as poly(3,4-ethylenedioxythiophene), polystyrene sulfonic acid, polyaniline, etc., copolymers, polymer mixtures, and small molecules, such as bathocuproine. Buffer layers may be applied using a deposition process (e.g., thermal evaporation) or a solution processing method (e.g., spin coating).

Figure 3B:
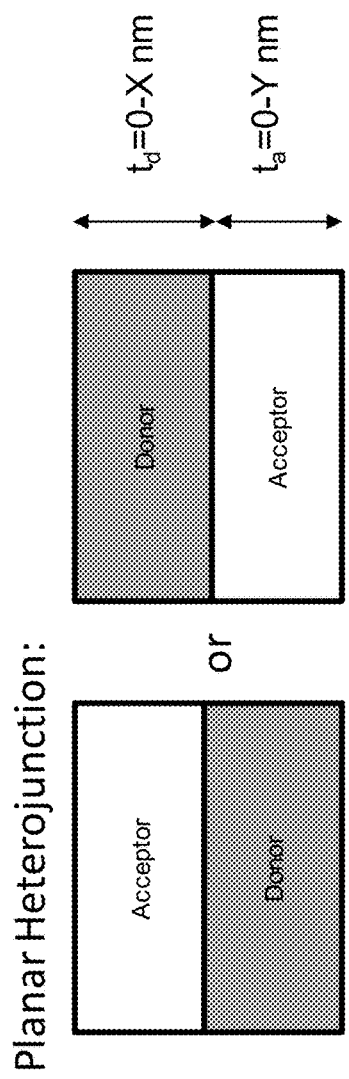
FIG. 3B provides an overview of various configurations of photoactive layer(s) in visibly transparent photovoltaic devices according to some examples.
Figure 3B:
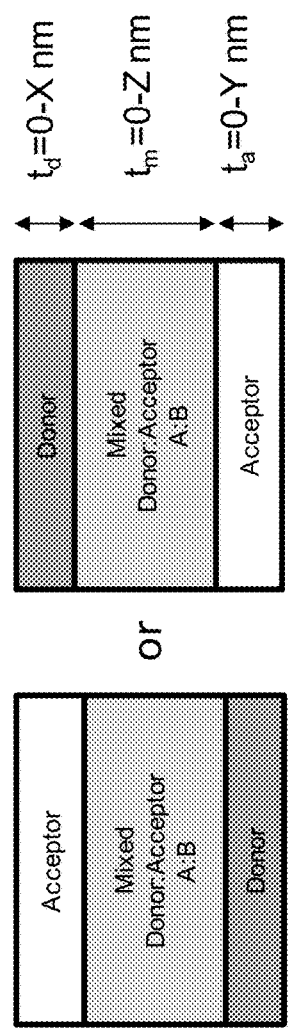
Figure 3B:
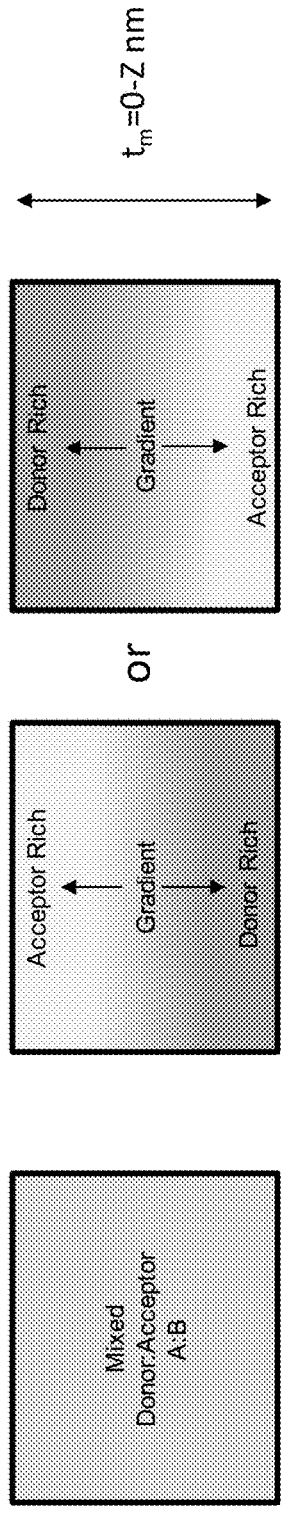

FIG. 3B depicts an overview of various example single junction configurations for photoactive layer 340. Photoactive layer 340 may optionally correspond to mixed donor/acceptor (bulk heterojunction) configurations, planar donor/acceptor configurations, planar and mixed donor/acceptor configurations, or gradient donor/acceptor configurations. Various materials may be used as the photoactive layers 340, such as visibly transparent materials that absorb in the ultraviolet band or the near-infrared band but that only absorb minimally, if at all, in the visible band. In this way, the photoactive material may be used to generate electron-hole pairs for powering an external circuit by way of ultraviolet and/or near-infrared absorption, leaving the visible light relatively unperturbed to provide visible transparency. In other cases, however, photoactive layers 340 may include materials that absorb in the visible region. As illustrated, photoactive layer 340 may comprise a planar heterojunction including separate donor and acceptor layers. Photoactive layer 340 may alternatively comprise a planar-mixed heterojunction structure including separate acceptor and donor layers and a mixed donor-acceptor layer. Photoactive layers 340 may alternatively comprise a mixed heterojunction structure including a fully mixed acceptor-donor layer or those including a mixed donor-acceptor layer with various relative concentration gradients.

Photoactive layers 340 may have any suitable thickness and may have any suitable concentration or composition of photoactive materials to provide a desired level of transparency and ultraviolet/near-infrared absorption characteristics. Example thicknesses of a photoactive layer may range from about 1 nm to about 1 µm, about 1 nm to about 300 nm, or about 1 nm to about 100 nm. In some cases, photoactive layers 340 may be made up of individual sub-layers or mixtures of layers to provide suitable photovoltaic power generation characteristics, as illustrated in FIG. 3B. The various configurations depicted in FIG. 3B may be used and dependent on the particular donor and acceptor materials used in order to provide advantageous photovoltaic power generation. For example, some donor and acceptor combinations may benefit from particular configurations, while other donor and acceptor combinations may benefit from other particular configurations. Donor materials and acceptor materials may be provided in any ratio or concentration to provide suitable photovoltaic power generation characteristics. For mixed layers, the relative concentration of donors to acceptors is optionally between about 20 to 1 and about 1 to 20. Optionally, the relative concentration of donors to acceptors is optionally between about 5 to 1 and about 1 to 5. Optionally, donors and acceptors are present in a 1 to 1 ratio.

It will be appreciated that, in various examples, photovoltaic device 300 comprises transparent electrode 320, photoactive layer(s) 340, and transparent electrode 322, and that any one or more of substrate 305, optical layers 310, 312, and 314, and/or buffer layers 330 and 332 may be optionally included or excluded.

As described more fully herein, disclosed examples can employ photoactive compounds for one or more of the buffer layers, optical layers, and/or the photoactive layers. These compounds can include suitably functionalized versions for modification of the electrical and/or optical properties of the core structure. As an example, the disclosed compounds can include functional groups that decrease the absorption properties in the visible wavelength band between 450 nm to 650 nm and increase the absorption properties in the NIR band at wavelengths greater than 650 nm.

As an example, the disclosed photoactive compounds are useful as an electron acceptor materials or electron donor materials, and may be paired with suitable counterpart materials of the opposite character, such as counterpart electron donor materials or counterpart electron acceptor materials, in order to provide a useful heterojunction-based photoactive layer in the photovoltaic device. Example electron donor photoactive materials or electron acceptor photoactive materials may be visibly transparent. In cases of partially transparent or opaque photovoltaic devices, the photoactive materials can absorb light in the visible region.

In examples, the chemical structure of the photoactive compounds can be functionalized with one or more directing groups, such as electron donating groups, electron withdrawing groups, or substitutions about or to a core metal atom or group, in order to provide desirable electrical characteristics to the material. For example, in some examples, the photoactive compounds are functionalized with amine groups, phenol groups, alkyl groups, phenyl groups, or other electron donating groups to improve the ability of the material to function as an electron donor in a photovoltaic device. As another example, in some examples, the photoactive compounds are functionalized with cyano groups, halogens, sulfonyl groups, or other electron withdrawing groups to improve the ability of the material to function as an electron acceptor in a photovoltaic device.

In examples, the photoactive compounds are functionalized to provide desirable optical characteristics. For example, in some examples, the photoactive compounds may be functionalized with an extended conjugation to redshift the absorption profile of the material. It will be appreciated that conjugation may refer to a delocalization of pi electrons in a molecule and may be characterized by alternating single and multiple bonds in a molecular chemical structure, and/or the presence of aromatic structures. For example, functionalizations that extend the electron conjugation may include fusing one or more aromatic groups to the molecular structure of the material. Other functionalizations that may provide extended conjugation include alkene functionalization, such as by a vinyl group, aromatic or heteroaromatic functionalization, carbonyl functionalization, such as by an acyl group, sulfonyl functionalization, nitro functionalization, cyano functionalization, etc. It will be appreciated that various molecular functionalizations may impact both the optical and the electrical properties of the photoactive compounds.

It will be appreciated that device function may be impacted by the morphology of the active layers in the solid state. Separation of electron donors and acceptors into discrete domains, with dimensions on the scale of the exciton diffusion length and large interfacial areas, can be advantageous for achieving high device efficiency. Advantageously, the molecular framework of the photoactive materials can be tailored to control the morphology of the materials. For example, the introduction of functional groups as described herein can have large impacts to the morphology of the material in the solid state, regardless of whether such modifications impact the energetics or electronic properties of the material. Such morphological variations can be observed in pure materials and when a particular material is blended with a corresponding donor or acceptor. Useful functionalities to control morphology include, but are not limited to, addition of alkyl chains, conjugated linkers, fluorinated alkanes, bulky groups (e.g., tert-butyl, phenyl, naphthyl or cyclohexyl), as well as more complex coupling procedures designed to force parts of the structure out of the plane of the molecule to inhibit excessive crystallization.

In examples, other molecular structural characteristics may provide desirable electrical and optical properties in the photoactive compounds. For example, in some examples, the photoactive compounds may exhibit portions of the molecule that may be characterized as electron donating while other portions of the molecule may be characterized as electron accepting. Without wishing to be bound by any theory, molecules including alternating electron donating and electron accepting portions may result in red-shifting the absorption characteristics of the molecule as compared to similar molecules lacking alternating electron donating and electron accepting portions. For example, alternating electron donating and electron accepting portions may decrease or otherwise result in a lower energy gap between a highest occupied molecular orbital and a lowest unoccupied molecular orbital. Organic donor and/or acceptor groups may be useful as R-group substituents, such as on any aryl, aromatic, heteroaryl, heteroaromatic, alkyl, or alkenyl group, in the visibly transparent photoactive compounds described herein. Example acceptor and donor groups are described below in more detail.

In examples, the photoactive compounds may exhibit symmetric structures, such as structures having two or more points of symmetry. Symmetric structures may include those where a core group is functionalized on opposite sides by the same groups, or where two of the same core groups are fused or otherwise bonded to one another. In other examples, the photoactive compounds may exhibit asymmetric structures, such as structures having fewer than two points of symmetry. Asymmetric structures may include those where a core group is functionalized on opposite sides by different groups or where two different core groups are fused or otherwise bonded to one another.

When the materials described herein are incorporated as a photoactive layer in a photovoltaic device, for example as an electron acceptor or an electron donor, the layer thicknesses can be controlled to vary device output, absorbance, or transmittance. For example, increasing the donor or acceptor layer thickness can increase the light absorption in that layer. In some cases, increasing a concentration of donor/acceptor materials in a donor or acceptor layer may similarly increase the light absorption in that layer. However, in some examples, a concentration of donor/acceptor materials may not be adjustable, such as when active material layers comprise pure or substantially pure layers of donor/acceptor materials or pure or substantially pure mixtures of donor/acceptor materials. Optionally, donor/acceptor materials may be provided in a solvent or suspended in a carrier, such as a buffer layer material, in which case the concentration of donor/acceptor materials may be adjusted. In some examples, the donor layer concentration is selected where the current produced is maximized. In some examples, the acceptor layer concentration is selected where the current produced is maximized.

However, the charge collection efficiency can decrease with increasing donor or acceptor thickness due to the increased "travel distance" for the charge carriers. Therefore, there may be a trade-off between increased absorption and decreasing charge collection efficiency with increasing layer thickness. It can thus be advantageous to select materials as described herein that have a high absorption coefficient and/or concentration to allow for increased light absorption per thickness. In some examples, the donor layer thickness is selected where the current produced is maximized. In some examples, the acceptor layer thickness is selected where the current produced is maximized.

In addition to the individual photoactive layer thicknesses formed from materials described herein, the thickness and composition of the other layers in the transparent photovoltaic device can also be selected to enhance absorption within the photoactive layers. The other layers (buffer layers, electrodes, etc.), are typically selected based on their optical properties (index of refraction and extinction coefficient) in the context of the thin film device stack and resulting optical cavity. For example, a near-infrared absorbing photoactive layer can be positioned in the peak of the optical field for the near-infrared wavelengths where it absorbs to maximize absorption and resulting current produced by the device. This can be accomplished by spacing the photoactive layer at an appropriate distance from the electrode using a second photoactive layer and/or optical layers as spacer. A similar scheme can be used for ultraviolet or visible absorbing photoactive layers. In many cases, the peaks of the longer wavelength optical fields will be positioned further from the more reflective of the two transparent electrodes compared to the peaks of the shorter wavelength optical fields. Thus, when using separate donor and acceptor photoactive layers, the donor and acceptor can be selected to position the more red absorbing (longer wavelength) material further from the more reflective electrode and the more blue absorbing (shorter wavelength) closer to the more reflective electrode.

In some examples, optical layers may be included to increase the intensity of the optical field at wavelengths where the donor absorbs in the donor layer to increase light absorption and hence, increase the current produced by the donor layer. In some examples, optical layers may be included to increase the intensity of the optical field at wavelengths where the acceptor absorbs in the acceptor layer to increase light absorption and hence, increase the current produced by the acceptor layer. In some examples, optical layers may be used to improve the transparency of the stack by either decreasing visible absorption or visible reflection. Further, the electrode material and thickness may be selected to enhance absorption outside the visible range within the photoactive layers, while preferentially transmitting light within the visible range.

Optionally, enhancing spectral coverage of a photovoltaic device is achieved by the use of a multi-cell series stack of photovoltaic devices, referred to as tandem cells, which may be included as multiple stacked instances of buffer layer 330, photoactive layer 340, and buffer layer 332, as described with reference to FIG. 3A. This architecture includes more than one photoactive layer, which are typically separated by a combination of buffer layer(s) and/or thin metal layers, for example. In this architecture, the currents generated in each subcell flow in series to the opposing electrodes and therefore, the net current in the cell is limited by the smallest current generated by a particular subcell, for example. The open circuit voltage (VOC) is equal to the sum of the VOCs of the subcells. By combining sub-cells fabricated with different donor-acceptors pairs which absorb in different regions of the solar spectrum, a significant improvement in efficiency relative to a single junction cell can be achieved.

Additional description related to the materials utilized in one or more of the buffer layers and the photoactive layers, including donor layers and/or acceptor layers, are provided below.

Figure 4:
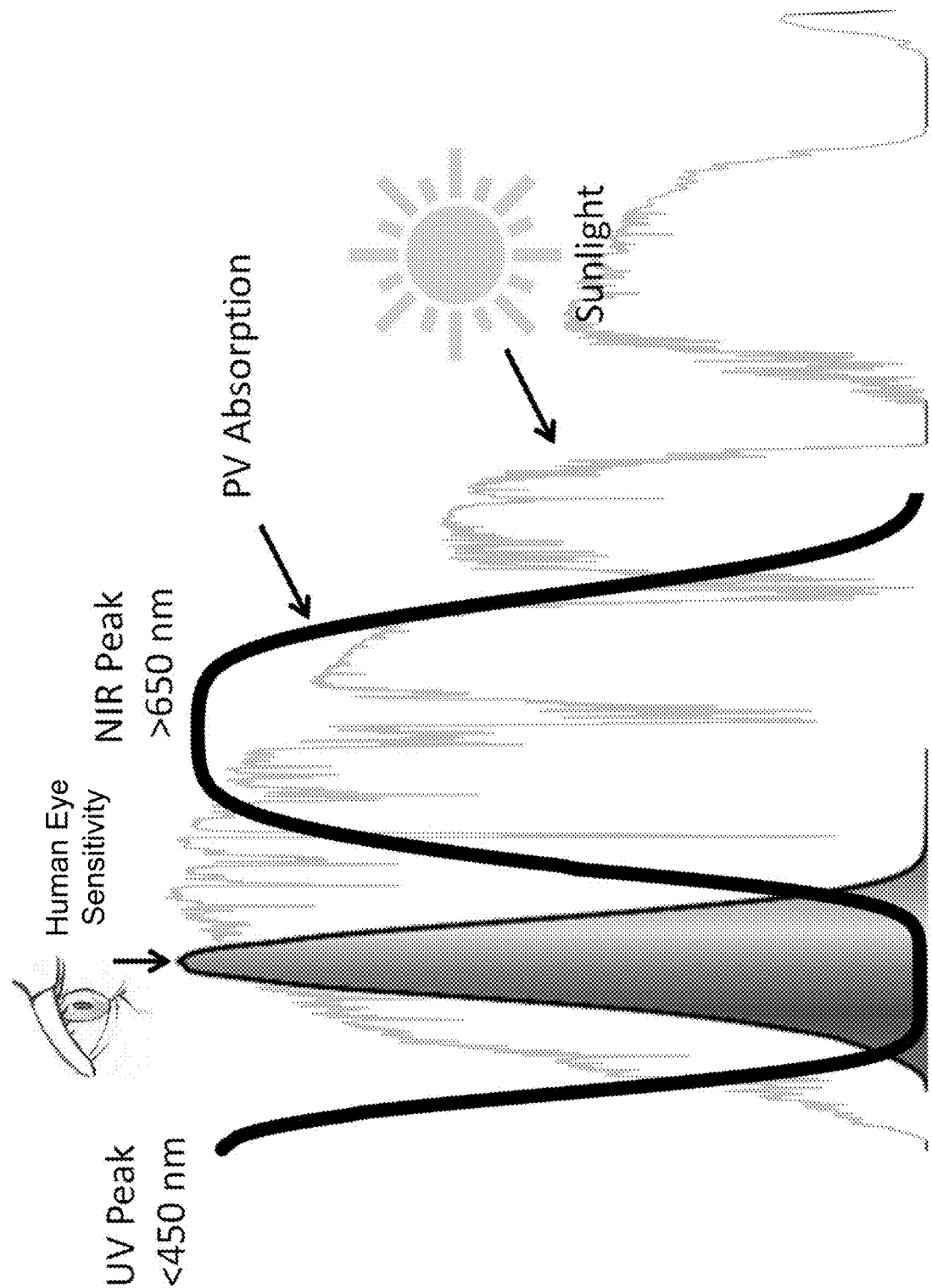
FIG. 4 is simplified plot illustrating the solar spectrum, human eye sensitivity, and exemplary transparent photovoltaic device absorption as a function of wavelength.

FIG. 4 is simplified plot illustrating the solar spectrum, human eye sensitivity, and exemplary visibly transparent photovoltaic device absorption as a function of wavelength. As illustrated in FIG. 4, examples of visibly transparent photovoltaic devices utilize photovoltaic structures that have low absorption in the visible wavelength band between about 450 nm and about 650 nm, but absorb in the UV and NIR bands, i.e., outside the visible wavelength band, enabling visibly transparent photovoltaic operation. The ultraviolet band or ultraviolet region may be described, in examples, as wavelengths of light of between about 200 nm and 450 nm. It will be appreciated that useful solar radiation at ground level may have limited amounts of ultraviolet less than about 280 nm and, thus, the ultraviolet band or ultraviolet region may be described as wavelengths of light of between about 280 nm and 450 nm, in some examples. The near-infrared band or near-infrared region may be described, in examples, as wavelengths of light of between about 650 nm and 1400 nm. Various compositions described herein may exhibit absorption including a NIR peak with a maximum absorption strength in the visible region that is smaller than that in the NIR region.

Figure 5:
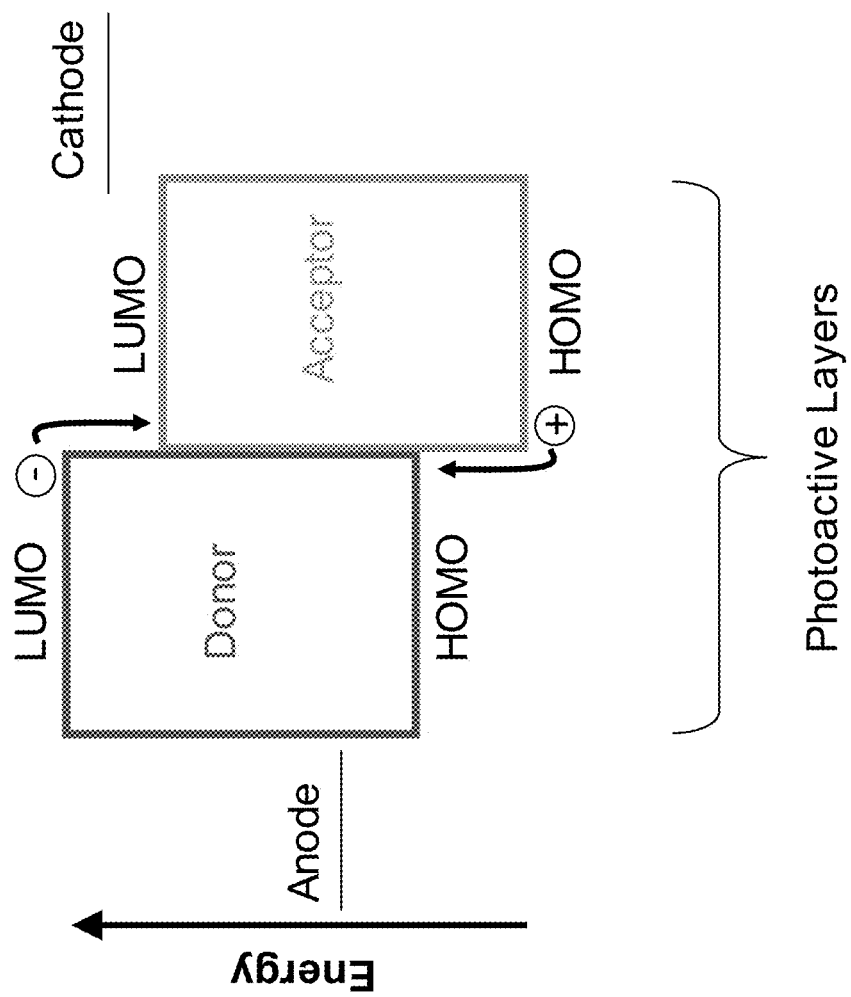
FIG. 5 is a simplified energy level diagram for a visibly transparent photovoltaic device according to some examples.

FIG. 5 provides a schematic energy level diagram overview for operation of an example organic photovoltaic device, such as visibly transparent photovoltaic device 300. For example, in such a photovoltaic device, various photoactive materials may exhibit electron donor or electron acceptor characteristics, depending on their properties and the types of materials that are used for buffer layers, counterpart materials, electrodes, etc. As depicted in FIG. 5, each of the donor and acceptor materials have a highest occupied molecular orbital (HOMO) and a lowest unoccupied molecular orbital (LUMO). A transition of an electron from the HOMO to the LUMO may be imparted by absorption of photons. The energy between the HOMO and the LUMO (the HOMO-LUMO gap) of a material represents approximately the energy of the optical band gap of the material. For the electron donor and electron acceptor materials useful with the transparent photovoltaic devices provided herein, the HOMO-LUMO gap for the electron donor and electron acceptor materials preferably falls outside the energy of photons in the visible range. For example, the HOMO-LUMO gap may be in the ultraviolet region or the near-infrared region, depending on the photoactive materials. In some cases, the HOMO-LUMO gap may be in the visible region or overlap with the visible region and the ultraviolet region or overlap with the visible region and the near-infrared region, such as for partially transparent or opaque photovoltaic devices. It will be appreciated that the HOMO is comparable to the valence band in conventional conductors or semiconductors, while the LUMO is comparable to the conduction band in conventional conductors or semiconductors.

The narrow absorption spectrum of many organic molecules, such as organic semiconductors, can make it difficult to absorb the entire absorption spectra using a single molecular species. Therefore, electron donor and acceptor molecules are generally paired to afford a complementary absorption spectrum and increase spectral coverage of light absorption. Additionally, the donor and acceptor molecules are selected such that their energy levels (HOMO and LUMO) lie favorably with respect to one another. The difference in the LUMO level of donor and acceptor provides a driving force for dissociation of electron-hole pairs (excitons) created on the donor whereas the difference in the HOMO levels of donor and acceptors provides driving force for dissociation of electron-hole pairs (excitons) created on the acceptor. In some examples, it may be useful for the acceptor to have high electron mobility to efficiently transport electrons to an adjacent buffer layer. In some examples, it may be useful for the donor to have high hole mobility to efficiently transport holes to the buffer layer. Additionally, in some examples, it may be useful to increase the difference in the LUMO level of the acceptor and the HOMO level of the donor to increase the open circuit voltage (VOC), since VOC has been shown to be directly proportional to the difference between LUMO of the acceptor and HOMO of the donor. Such donor-acceptor pairings within the photoactive layer may be accomplished by appropriately pairing one of the materials described herein with a complementary material, which could be a different photoactive compound described herein or a completely separate material system.

The buffer layer adjacent to the donor, generally referred to as the anode buffer layer or hole transport layer, is selected such that HOMO level or valence band (in the case of inorganic materials) of the buffer layer is aligned in the energy landscape with the HOMO level of the donor to transport holes from the donor to the anode (transparent electrode). In some examples, it may be useful for the buffer layer to have high hole mobility. The buffer layer adjacent to the acceptor, generally referred to as the cathode buffer layer or electron transport layer, is selected such that LUMO level or conduction band (in the case of inorganic materials) of the buffer layer is aligned in the energy landscape with the LUMO level of the acceptor to transport electrons from the acceptor to the cathode (transparent electrode). In some examples, it may be useful for the buffer layer to have high electron mobility.

Figures 6A, 6B:
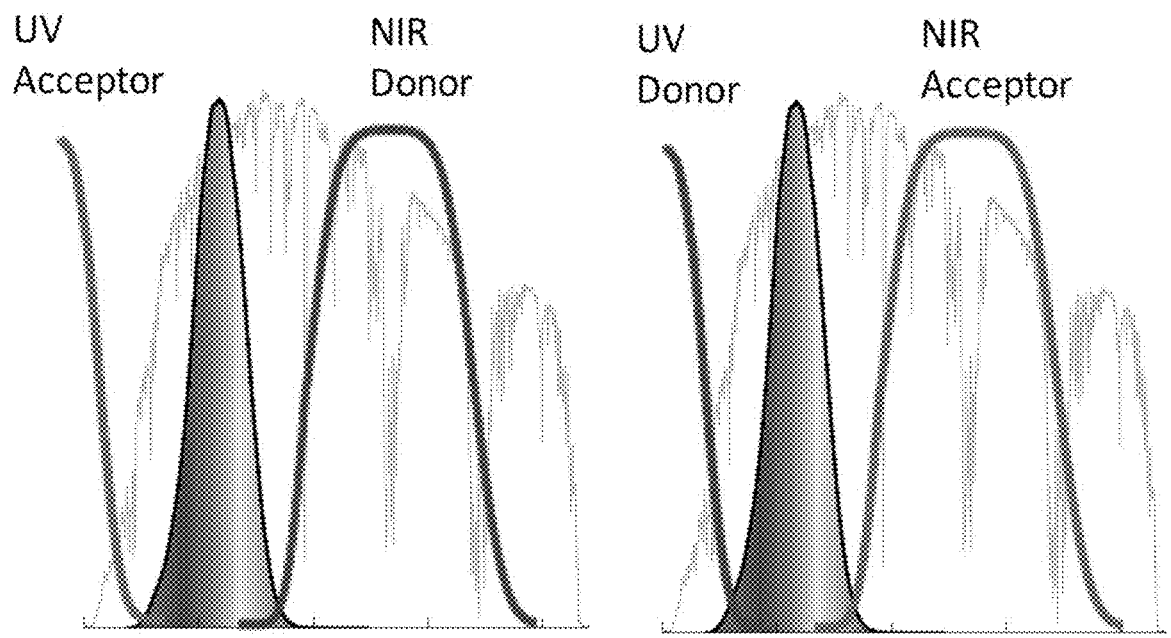
FIG. 6A, FIG. 6B, FIG. 6C, and FIG. 6D provide plots showing example absorption profiles for different electron acceptor and electron donor configurations, which can comprise the photoactive layers.

FIG. 6A, FIG. 6B, FIG. 6C, and FIG. 6D provide plots showing example absorption bands for different electron donor and electron acceptor configurations useful with visibly transparent photovoltaic devices. In FIG. 6A, the donor material exhibits absorption in the NIR, while the acceptor material exhibits absorption in the UV. FIG. 6B depicts the opposite configuration, where the donor material exhibits absorption in the UV, while the acceptor material exhibits absorption in the NIR.

Figures 6C, 6D:
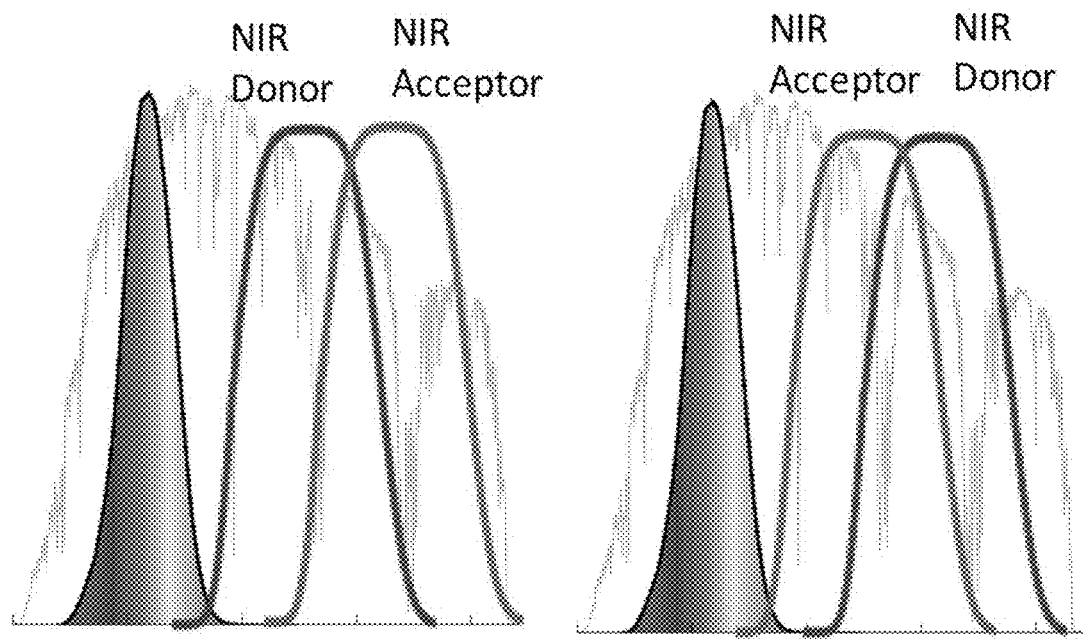

FIG. 6C depicts an additional configuration, where both the donor and acceptor materials exhibit absorption in the NIR. As illustrated in the figures, the solar spectrum exhibits significant amounts of useful radiation in the NIR with only relatively minor amounts in the ultraviolet, making the configuration depicted in FIG. 6C useful for capturing a large amount of energy from the solar spectrum. It will be appreciated that other examples are contemplated where both the donor and acceptor materials exhibit absorption in the NIR, such as depicted in FIG. 6D where the acceptor is blue shifted relative to the donor, opposite the configuration depicted in FIG. 6C, where the donor is blue shifted relative to the acceptor.

Figure 7:
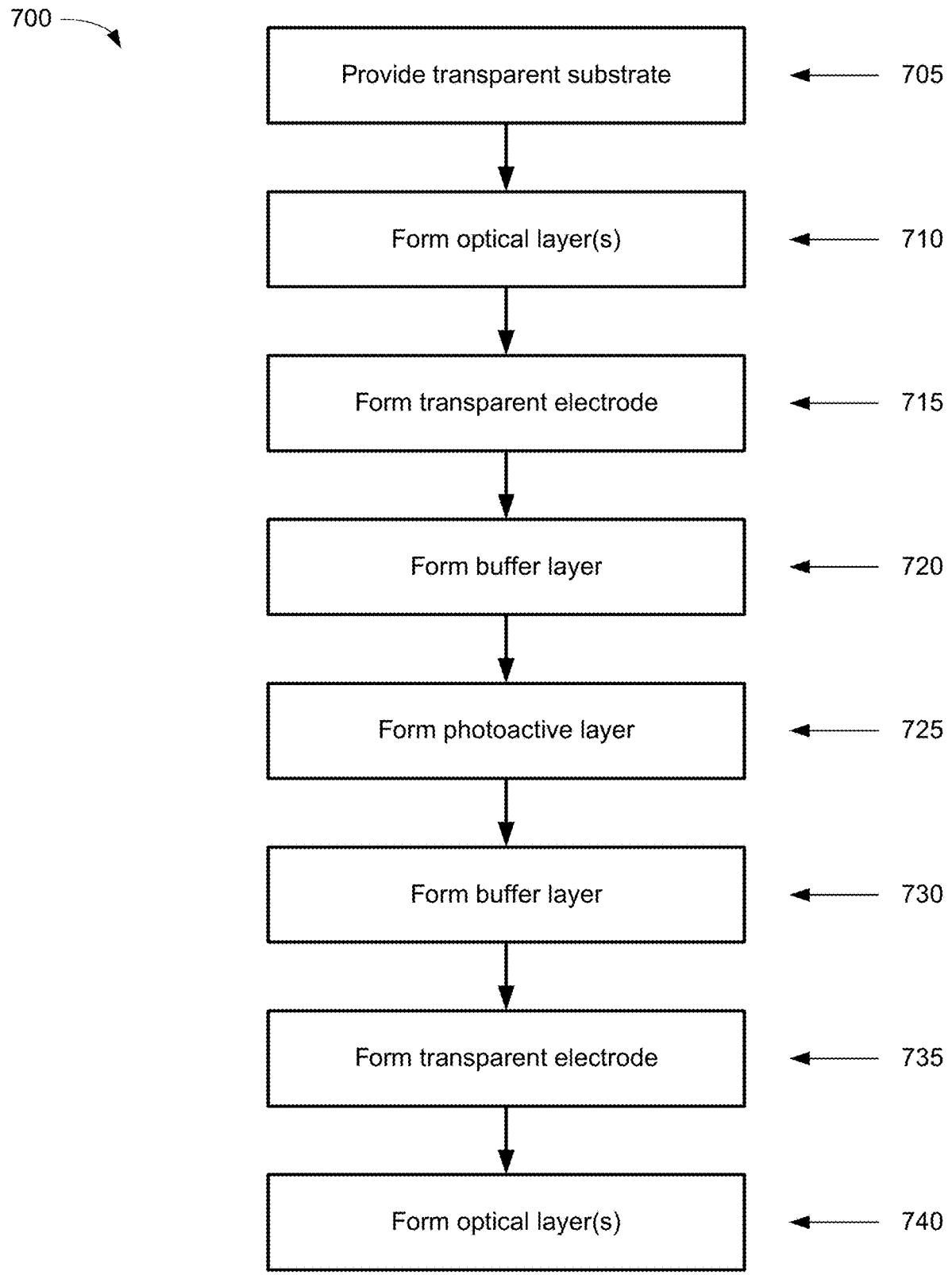
FIG. 7 provides an overview of a method of making visibly transparent photovoltaic devices according to some examples.

The present disclosure also provides methods for making photovoltaic devices, such as photovoltaic device 300. For example, FIG. 7 provides an overview of a method 700 for making a photovoltaic device in accordance with some examples. Method 700 begins at block 705, where a transparent substrate is provided. It will be appreciated that useful transparent substrates include visibly transparent substrates, such as glass, plastic, quartz, and the like. Flexible and rigid substrates are useful with various examples. Optionally, the transparent substrate is provided with one or more optical layers preformed on top and/or bottom surfaces.

At block 710, one or more optical layers are optionally formed on or over the transparent substrate, such as on top and/or bottom surfaces of the transparent substrate. Optionally, the one or more optical layers are formed on other materials, such as an intervening layer or material, such as a transparent conductor. Optionally, the one or more optical layers are positioned adjacent to and/or in contact with the visibly transparent substrate. It will be appreciated that formation of optical layers is optional, and some examples may not include optical layers adjacent to and/or in contact with the transparent substrate. Optical layers may be formed using a variety of methods including, but not limited to, one or more chemical deposition methods, such as plating, chemical solution deposition, spin coating, dip coating, chemical vapor deposition, plasma enhanced chemical vapor deposition, and atomic layer deposition, or one or more physical deposition methods, such as thermal evaporation, electron beam evaporation, molecular beam epitaxy, sputtering, pulsed laser deposition, ion beam deposition, and electrospray deposition. It will be appreciated that useful optical layers include visibly transparent optical layers. Useful optical layers include those that provide one or more optical properties including, for example, antireflection properties, wavelength selective reflection or distributed Bragg reflection properties, index matching properties, encapsulation, or the like. Useful optical layers may optionally include optical layers that are transparent to ultraviolet and/or near-infrared light. Depending on the configuration, however, some optical layers may optionally provide passive infrared and/or ultraviolet absorption. Optionally, an optical layer may include a visibly transparent photoactive compound described herein.

At block 715, a transparent electrode is formed. As described above, the transparent electrode may correspond to an indium tin oxide thin film or other transparent conducting film, such as thin metal films (e.g., Ag, Cu, etc.), multilayer stacks comprising thin metal films (e.g., Ag, Cu, etc.) and dielectric materials, or conductive organic materials (e.g., conducting polymers, etc.). It will be appreciated that transparent electrodes include visibly transparent electrodes. Transparent electrodes may be formed using one or more deposition processes, including vacuum deposition techniques, such as atomic layer deposition, chemical vapor deposition, physical vapor deposition, thermal evaporation, sputter deposition, epitaxy, etc. Solution based deposition techniques, such as spin-coating, may also be used in some cases. In addition, transparent electrodes may be patterned by way of microfabrication techniques, such as lithography, lift off, etching, etc.

At block 720, one or more buffer layers are optionally formed, such as on the transparent electrode. Buffer layers may be formed using a variety of methods including, but not limited to, one or more chemical deposition methods, such as a plating, chemical solution deposition, spin coating, dip coating, chemical vapor deposition, plasma enhanced chemical vapor deposition, and atomic layer deposition, or one or more physical deposition methods, such as thermal evaporation, electron beam evaporation, molecular beam epitaxy, sputtering, pulsed laser deposition, ion beam deposition, and electrospray deposition. It will be appreciated that useful buffer layers include visibly transparent buffer layers. Useful buffer layers include those that function as electron transport layers, electron blocking layers, hole transport layers, hole blocking layers, optical spacers, physical buffer layers, charge recombination layers, or charge generation layers. In some cases, the disclosed visibly transparent photoactive compounds may be useful as a buffer layer material. For example, a buffer layer may optionally include a visibly transparent photoactive compound described herein.

At block 725, one or more photoactive layers are formed, such as on a buffer layer or on a transparent electrode. As described above, photoactive layers may comprise electron acceptor layers and electron donor layers or co-deposited layers of electron donors and acceptors. Useful photoactive layers include those comprising the photoactive compounds described herein. Photoactive layers may be formed using a variety of methods including, but not limited to, one or more chemical deposition methods, such as a plating, chemical solution deposition, spin coating, dip coating, chemical vapor deposition, plasma enhanced chemical vapor deposition, and atomic layer deposition, or one or more physical deposition methods, such as thermal evaporation, electron beam evaporation, molecular beam epitaxy, sputtering, pulsed laser deposition, ion beam deposition, and electrospray deposition.

In some examples, photoactive compounds useful for photoactive layers may be deposited using a vacuum deposition technique, such as thermal evaporation. Vacuum deposition may take place in a vacuum chamber, such as at pressures of between about $10^{-5}$ Torr and about $10^{-8}$ Torr. In one example, vacuum deposition may take place at a pressure of about $10^{-7}$ Torr. As noted above, various deposition techniques may be applied. In some examples, thermal evaporation is used. Thermal evaporation may include heating a source of the material (i.e., the visibly transparent photoactive compound) to be deposited to a temperature of between 150° C. and 500° C. The temperature of the source of material may be selected so as to achieve a thin film growth rate of between about 0.01 nm/s and about 1 nm/s. For example, a thin film growth rate of 0.1 nm/s may be used. These growth rates are useful to generate thin films having thicknesses of between about 1 nm and 500 nm over the course of minutes to hours. It will be appreciated that various properties (e.g., the molecular weight, volatility, thermal stability) of the material being deposited may dictate or influence the source temperature or maximum useful source temperature. For example, a thermal decomposition temperature of the material being deposited may limit the maximum temperature of the source. As another example, a material being deposited that is highly volatile may require a lower source temperature to achieve a target deposition rate as compared to a material that is less volatile, where a higher source temperature may be needed to achieve the target deposition rate. As the material being deposited is evaporated from the source, it may be deposited on a surface (e.g., substrate, optical layer, transparent electrode, buffer layer, etc.) at a lower temperature. For example, the surface may have a temperature from about 10° C. to about 100° C. In some cases, the temperature of the surface may be actively controlled. In some cases, the temperature of the surface may not be actively controlled.

At block 730, one or more buffer layers are optionally formed, such as on the photoactive layer. The buffer layers formed at block 730 may be formed similar to those formed at block 720. It will be appreciated that blocks 720, 725, and 730 may be repeated one or more times, such as to form a multilayer stack of materials including a photoactive layer and, optionally, various buffer layers.

At block 735, a second transparent electrode is formed, such as on a buffer layer or on a photoactive layer. Second transparent electrode may be formed using techniques applicable to formation of first transparent electrode at block 715.

At block 740, one or more additional optical layers are optionally formed, such as on the second transparent electrode.

It should be appreciated that the specific steps illustrated in FIG. 7 provide a particular method of making a photovoltaic device according to various examples. Other sequences of steps may also be performed according to alternative examples. For example, alternative examples may perform the steps outlined above in a different order. Moreover, the individual steps illustrated in FIG. 7 may include multiple sub-steps that may be performed in various sequences as appropriate to the individual step. Furthermore, additional steps may be added or removed depending on the particular applications. It will be appreciated that many variations, modifications, and alternatives may be used.

Method 700 may optionally be extended to correspond to a method for generating electrical energy. For example, a method for generating electrical energy may comprise providing a photovoltaic device, such as by making a photovoltaic device according to method 700. Methods for generating electrical energy may further comprise exposing the photovoltaic device to visible, ultraviolet and/or near-infrared light to drive the formation and separation of electron-hole pairs, as described above with reference to FIG. 5, for example, for generation of electrical energy. The photovoltaic device may include the photoactive compounds described herein as photoactive materials, buffer materials, and/or optical layers.

Turning now to further details on photoactive compounds, in some examples, the photoactive compounds described herein comprises a zinc chelated dipyrromethene compound, such as having a formula of

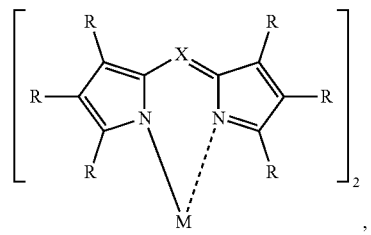

where X is N or C—R, and M is a metal with a stable +2 oxidation state. In some examples, M is Zn, Co, Cu, Ni, Fe, Pb, Mg, Mn, Pd, Pt, or Sn. In some cases, the identity of the metal atom can be useful for adjusting the absorption.

R groups for the disclosed photoactive compounds may comprise any suitable group, such as H, a halogen, or an organic group, optionally including one or more heteroatoms. In some cases, each R group may independently comprise H, F, Cl, Br, I, $CF_3$, CN, a substituted or unsubstituted alkyl group, a substituted or unsubstituted alkenyl group, a substituted or unsubstituted alkynyl group, a substituted or unsubstituted alkoxy group, a substituted or unsubstituted 5-membered ring, a substituted or unsubstituted 5-membered heterocyclic ring, a substituted or unsubstituted 6-membered ring, a substituted or unsubstituted 6-membered heterocyclic ring, or a substituted or unsubstituted fused ring. Specific example R groups include, but are not limited to H, F, Cl, Br, I, $CH_3$, $CF_3$, $C(CH_3)_3$, $CH(CH_3)_2$, $OCH_3$, $Si(CH_3)_3$,

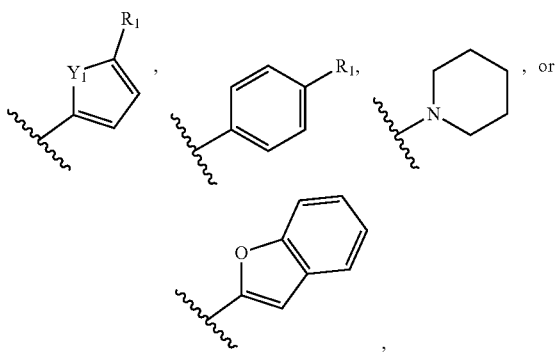

where $Y_1$ is NH, alkyl substituted N, alkyl substituted Si, O, or S, and where $R_1$ is H, F, Cl, Br, I, $CH_3$, $CF_3$, $C(CH_3)_3$, $CH(CH_3)_2$, $OCH_3$, or $Si(CH_3)_3$.

In some examples, the photoactive compounds described herein comprise a metal (e.g., zinc) chelated dipyrromethene compound, such as having a formula of

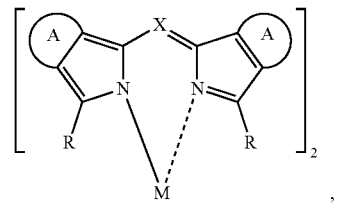

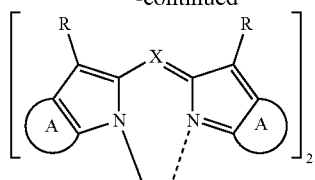

, or

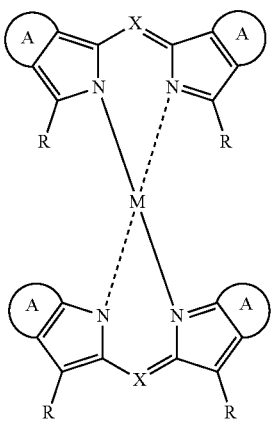

where X is N or C—R, and M is a metal with a stable +2 oxidation state. In some examples, M is Zn, Co, Cu, Ni, Fe, Pb, Mg, Mn, Pd, Pt, or Sn. Each A ring may comprise, independently, a 5-membered ring, a 6-membered ring, or a fused ring group including, but not limited to, non-aromatic, aromatic, and/or heteroaromatic moieties. In some examples R is, but is not limited to, H, F, Cl, Br, I, $CF_3$, a substituted silyl group, a substituted or unsubstituted alkyl group, a substituted or unsubstituted alkenyl group, a substituted or unsubstituted alkynyl group, a substituted or unsubstituted alkoxy group, a substituted or unsubstituted 5-membered ring, a substituted or unsubstituted 5-membered heterocyclic ring, a substituted or unsubstituted 6-membered ring, a substituted or unsubstituted 6-membered heterocyclic ring, or a substituted or unsubstituted fused ring.

In some examples, two R groups together can form a ring group optionally having one or more R substituents, such as a 5-membered ring, a 6-membered ring, or a fused ring group. Example photoactive compounds where two R groups together form a ring include

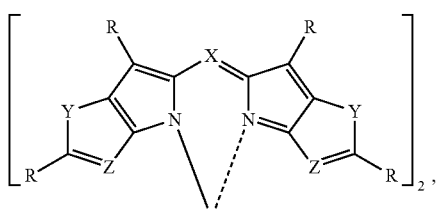

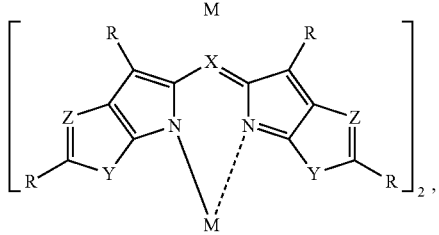

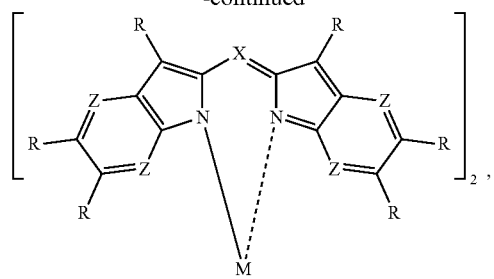

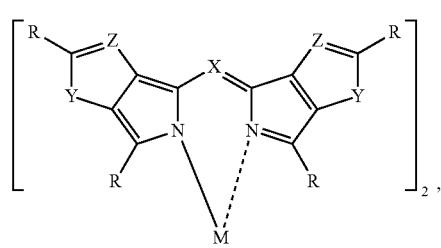

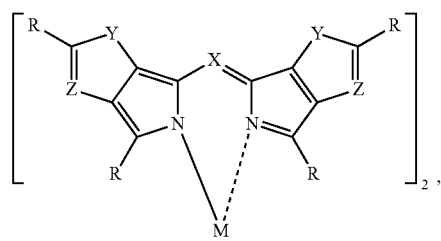

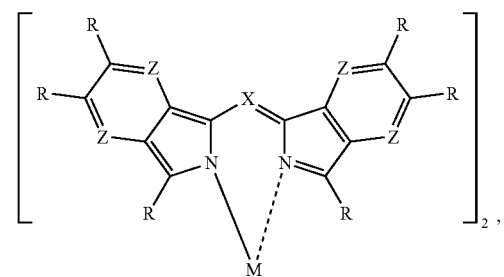

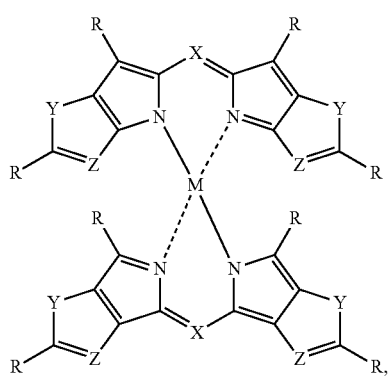

-continued
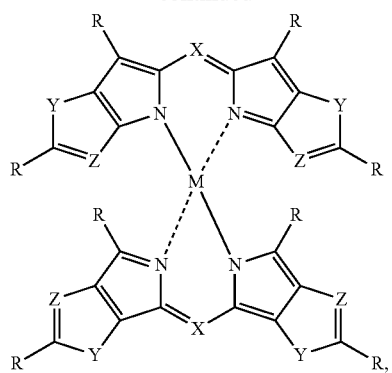
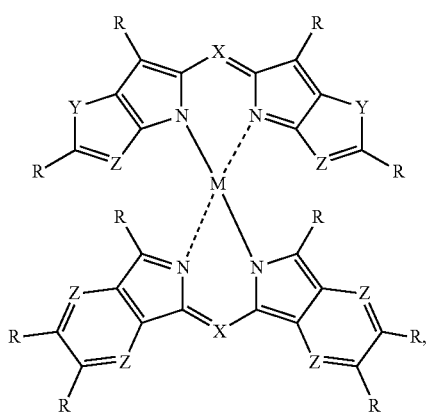
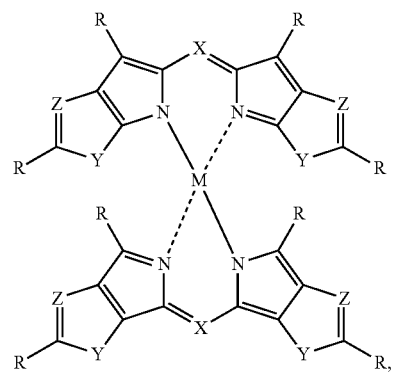
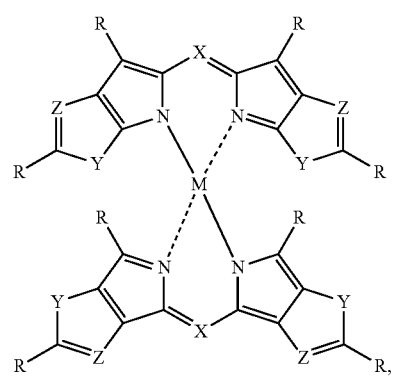
-continued
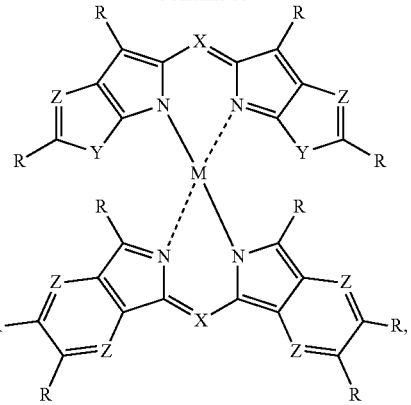
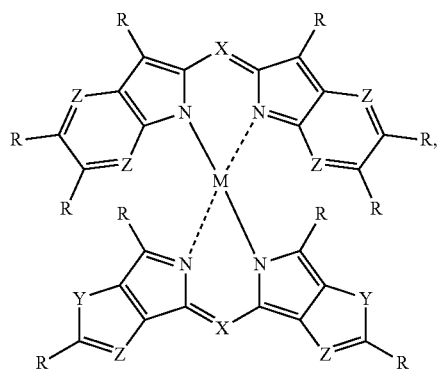
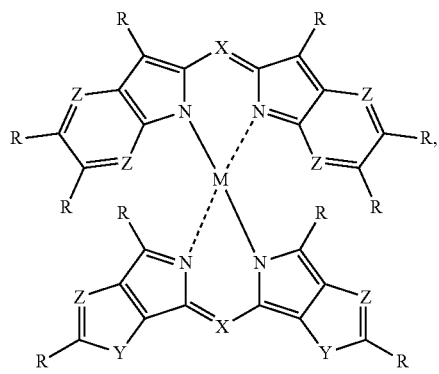
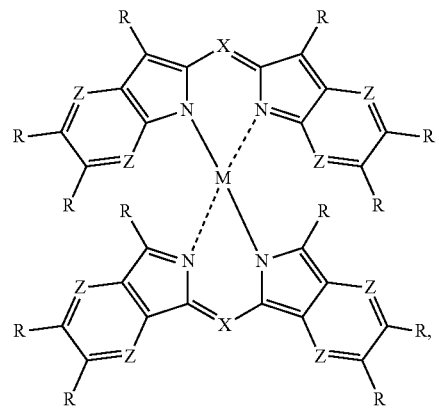

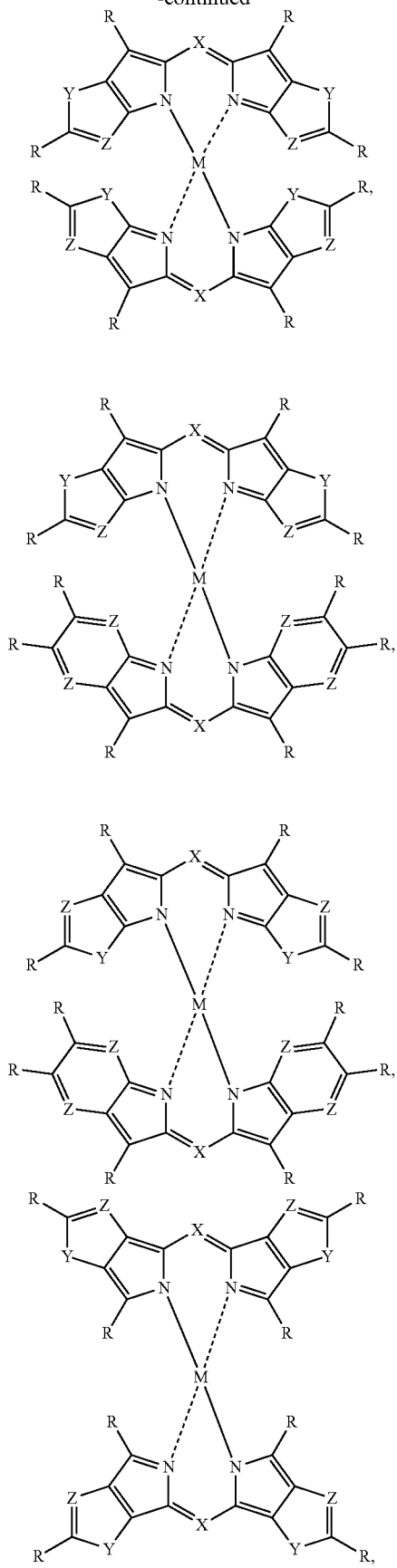

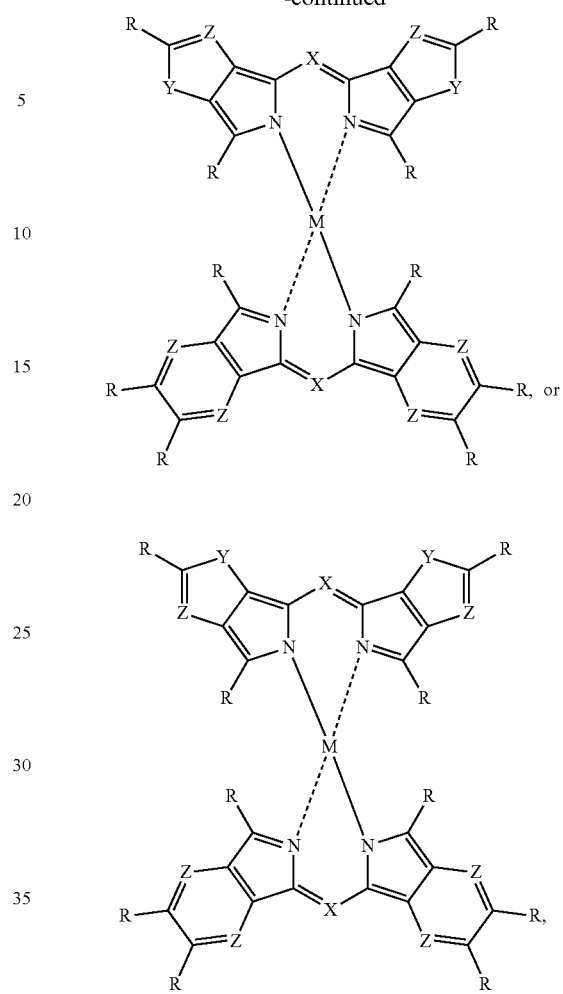

where each X is N or C—R and where each Y is independently C—R, O, N, alkyl substituted N, alkyl substituted Si, S, Se, or Te and where each Z is independently C—R or N.

Advantageously, the photoactive compounds can have molecular weights making them suitable for gas-phase deposition techniques, such as molecular weights from 200 amu to 1500 amu, for example. The photoactive compounds can exhibit thermal decomposition temperatures from 150° C. to 500° C. or greater than 500° C. and/or sublimation temperatures of 150° C. to 450° C. at pressures from 0.2 Torr to $10^{-7}$ Torr. These characteristics can aid or impart stability making the photoactive compounds suitable for use in gas-phase deposition processes.

The photoactive compounds can exhibit optical properties, as described above, such as where the photoactive compound exhibits absorption in the ultraviolet, visible, and/or infrared regions. In some cases, the compounds exhibit a bandgap of from 0.5 eV to 4.0 eV. For visibly transparent photoactive compounds, the bandgap may be from 0.5 eV to 1.9 eV or from 2.7 eV to 4.0 eV.

A variety of different photoactive compounds can be formulated and used according to the above description. Some specific example photoactive compounds include those having any of the following formulas:

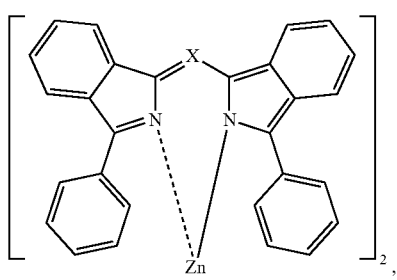
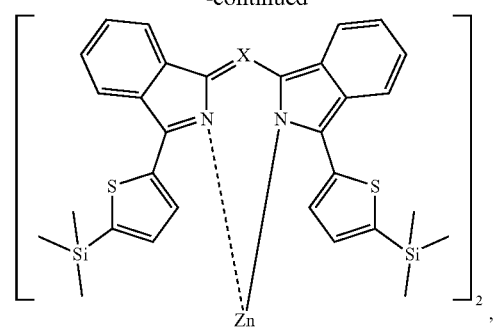
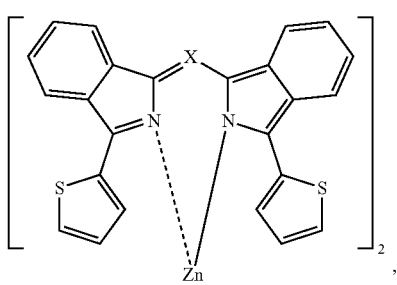
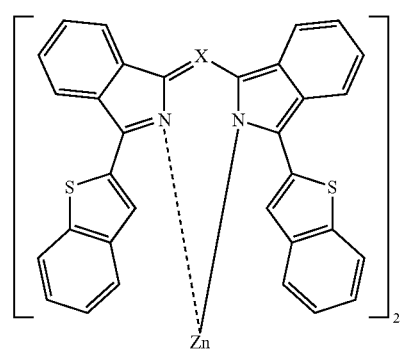
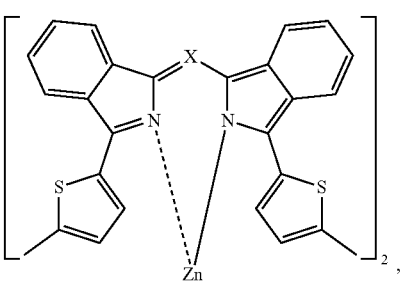
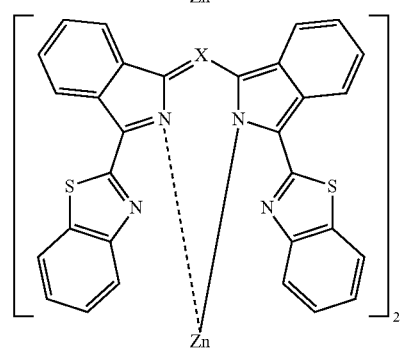
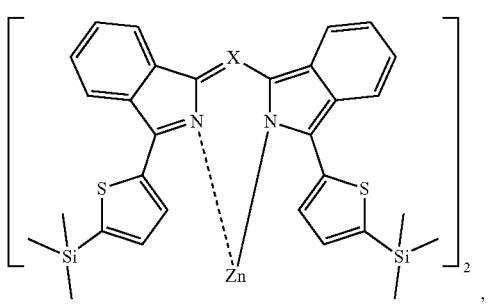
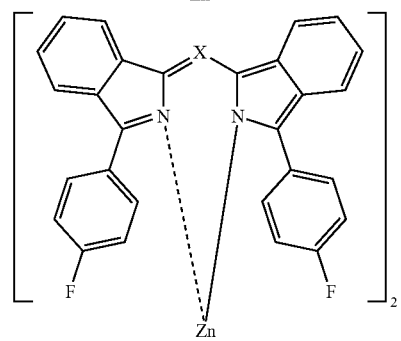
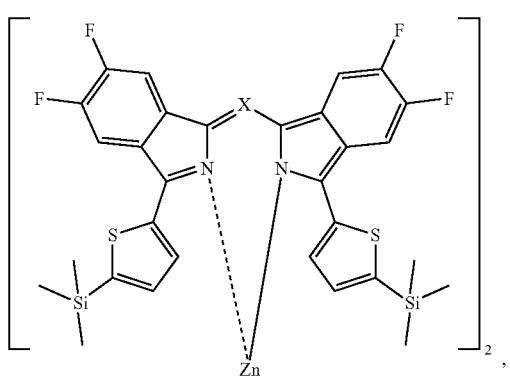
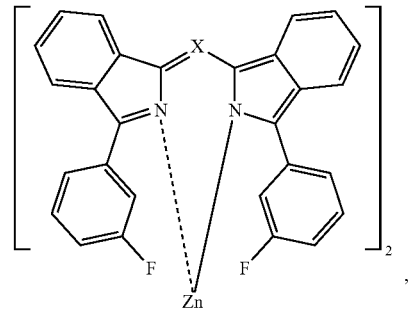

-continued
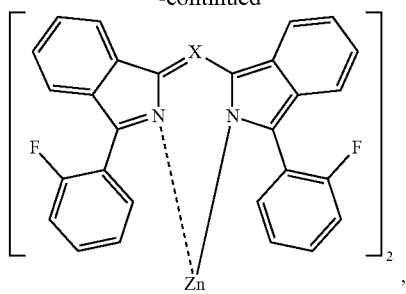
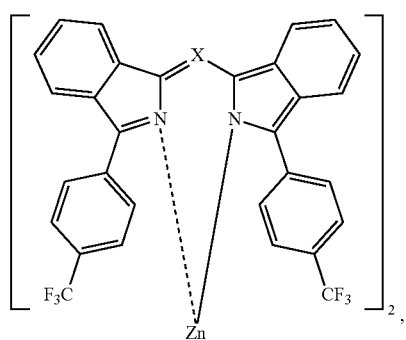
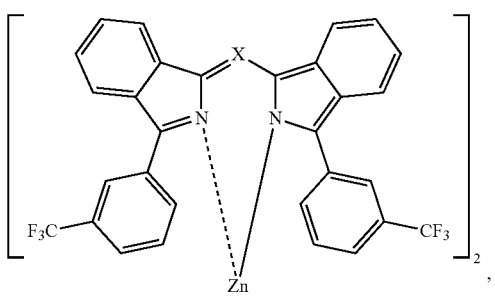
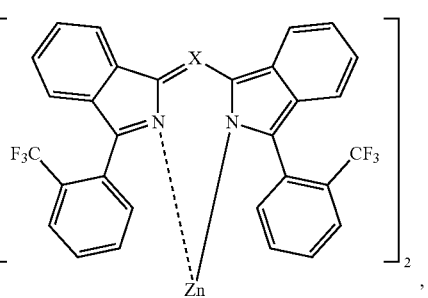
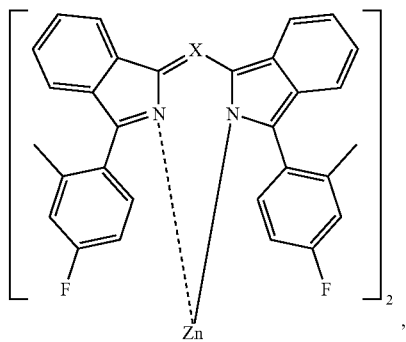
-continued
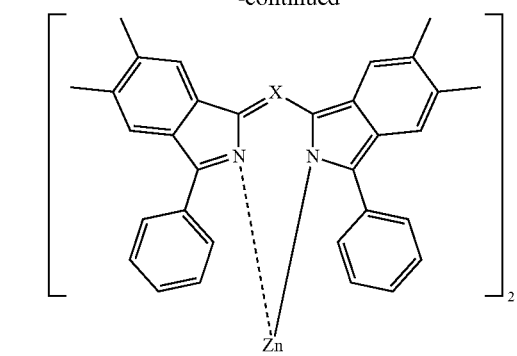
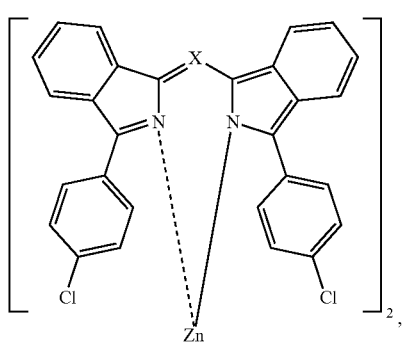
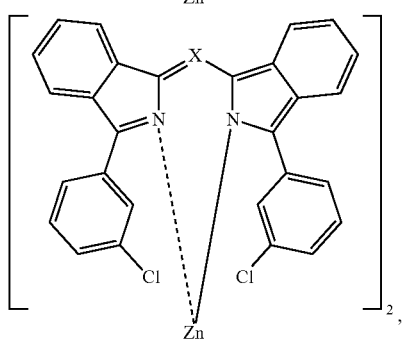
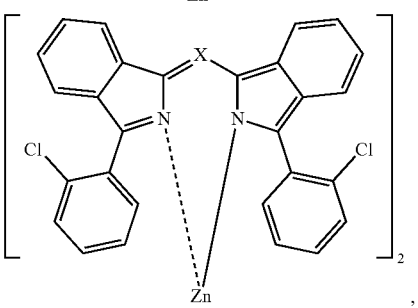
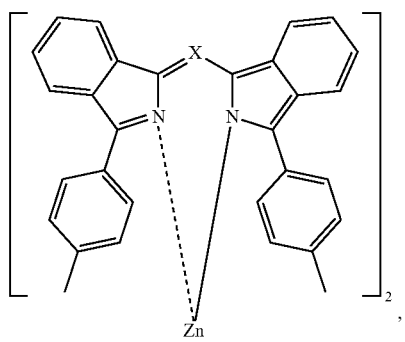

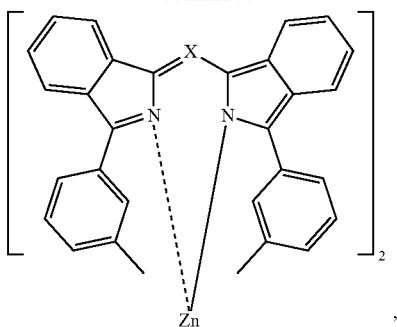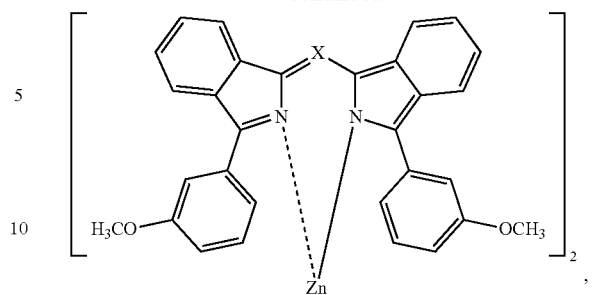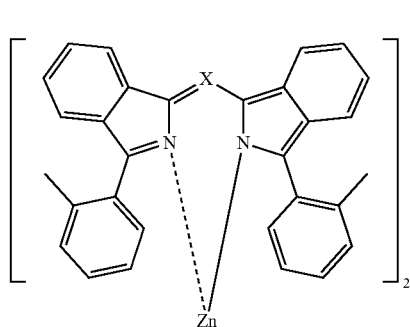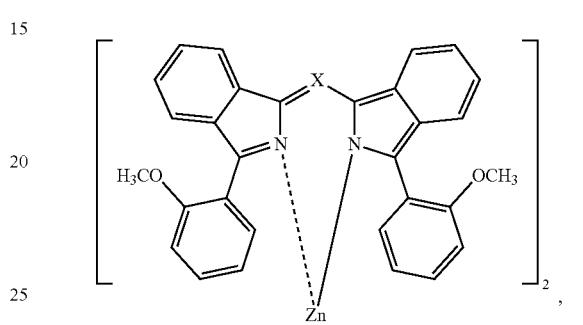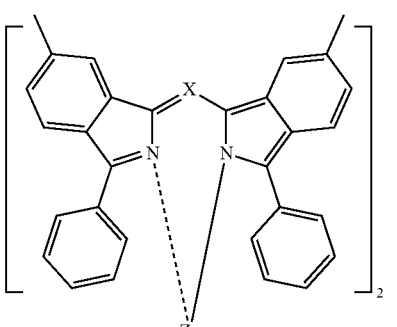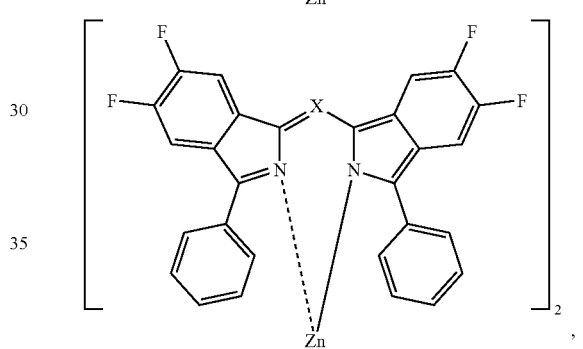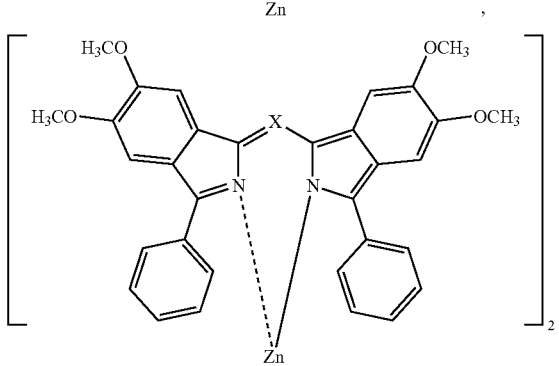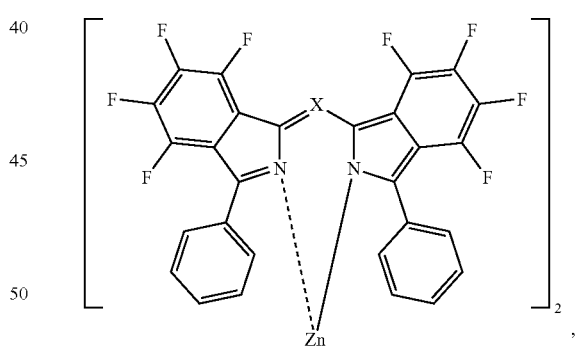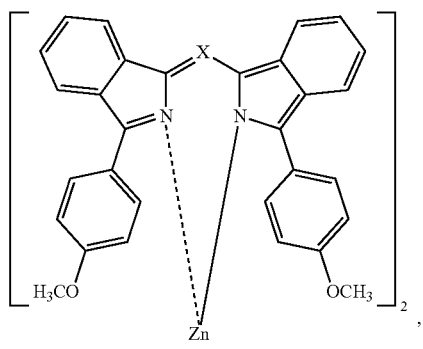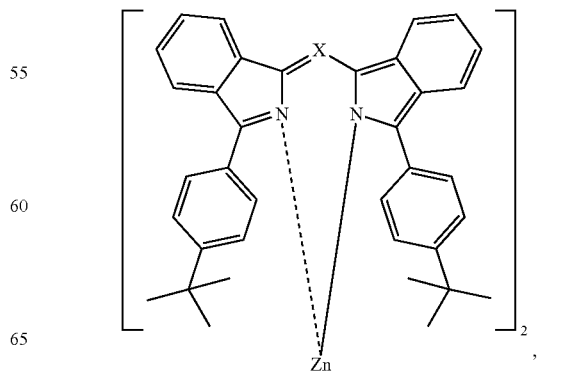

-continued
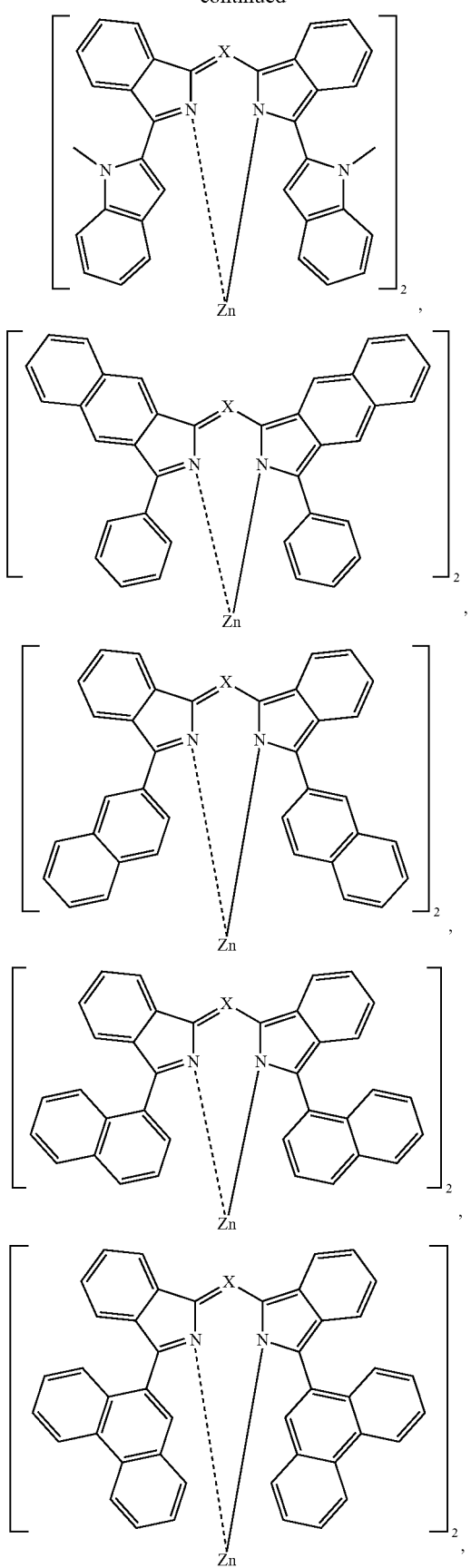
-continued
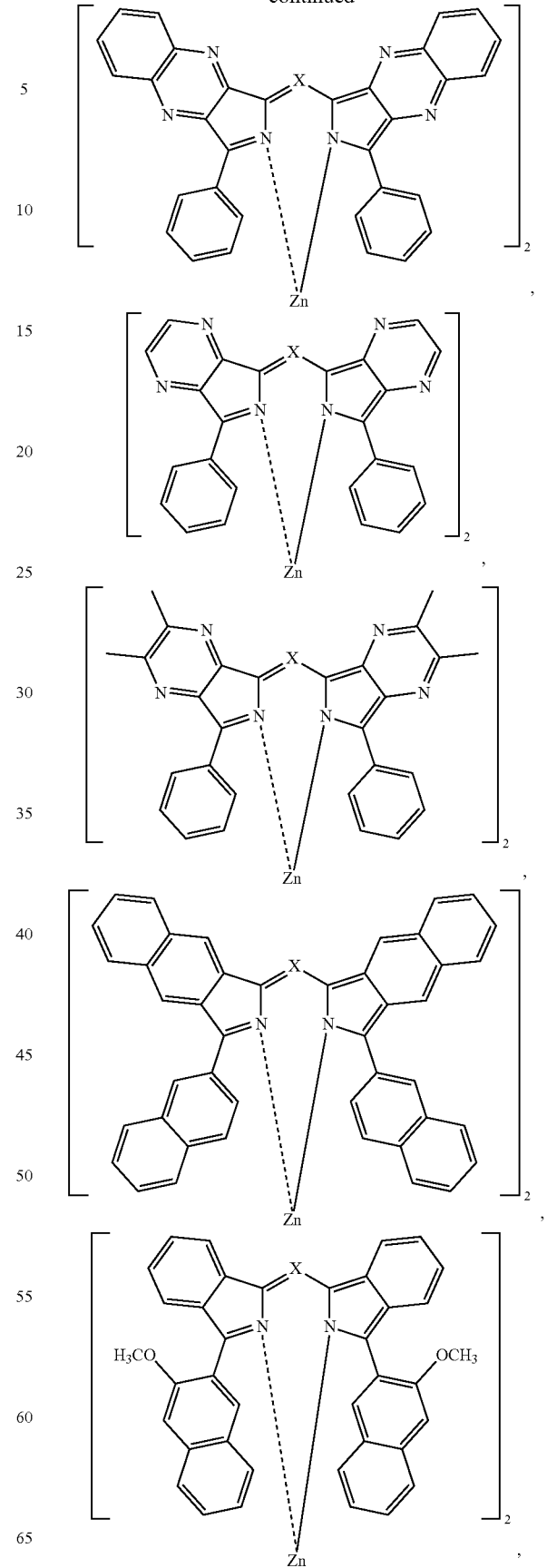

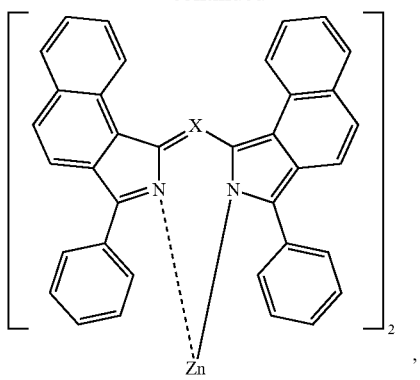
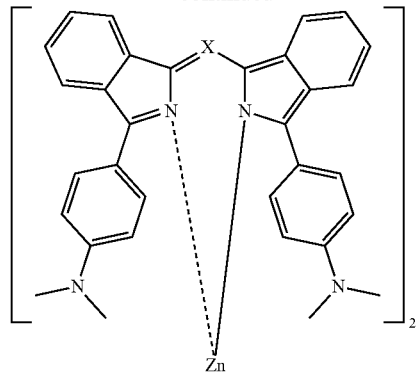
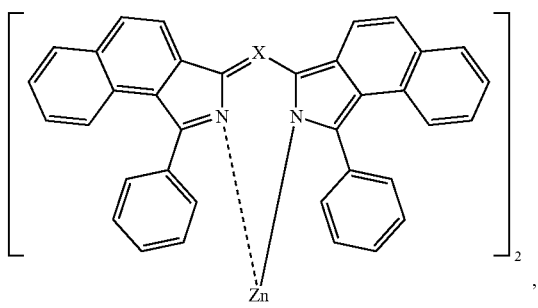
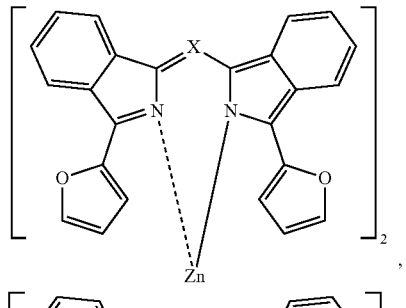
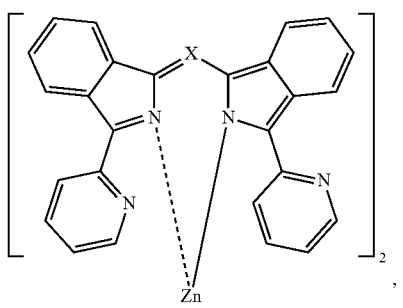
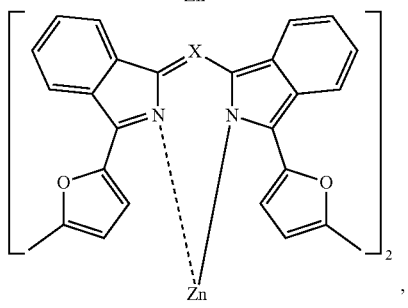
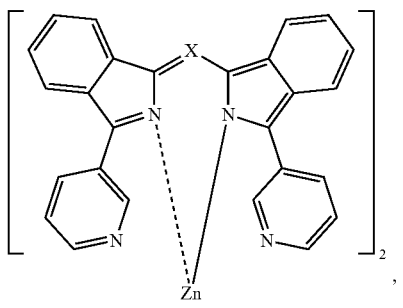
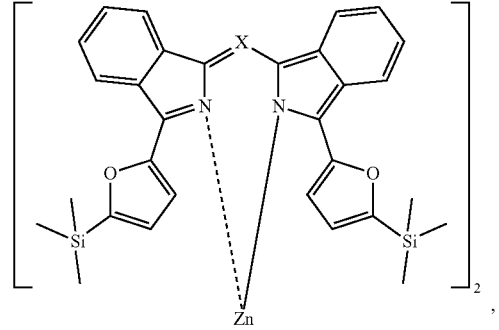
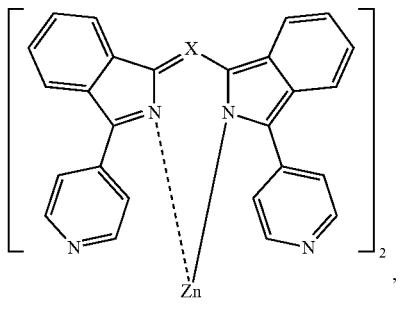
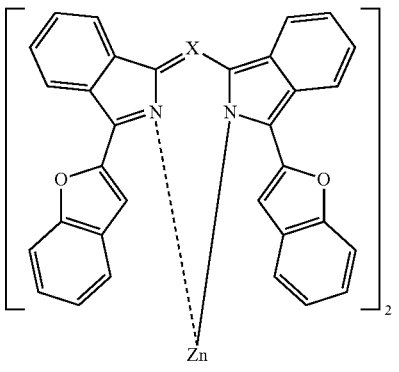

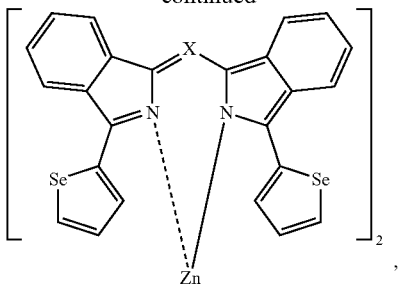
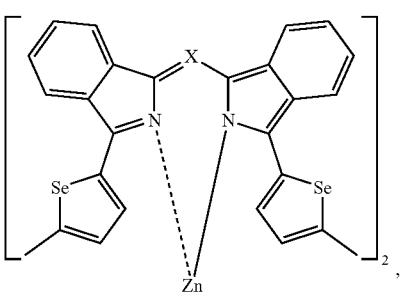
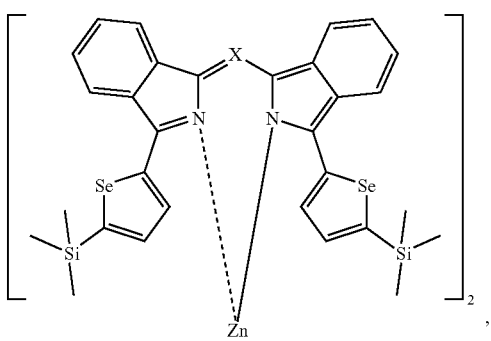
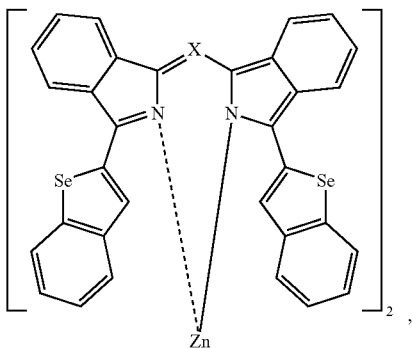
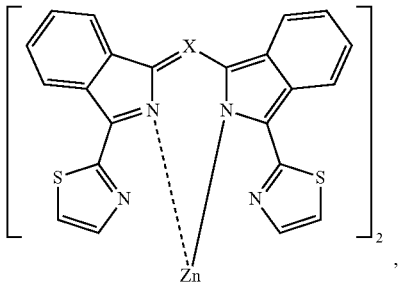
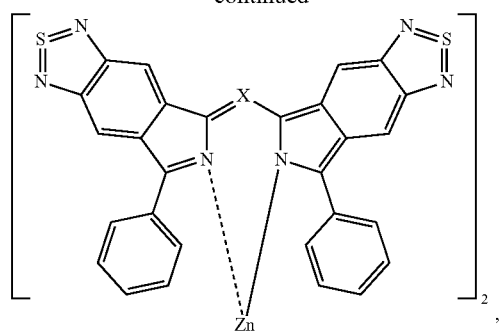
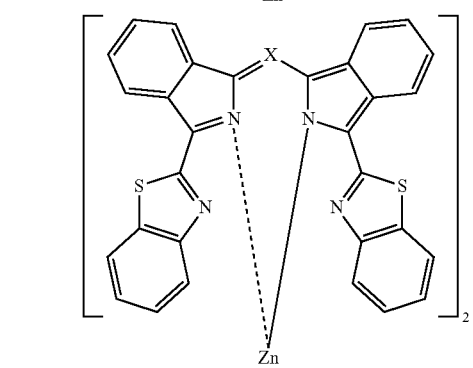
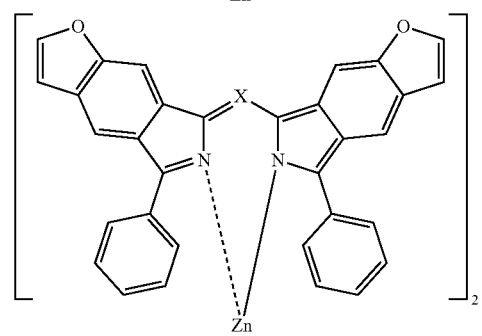
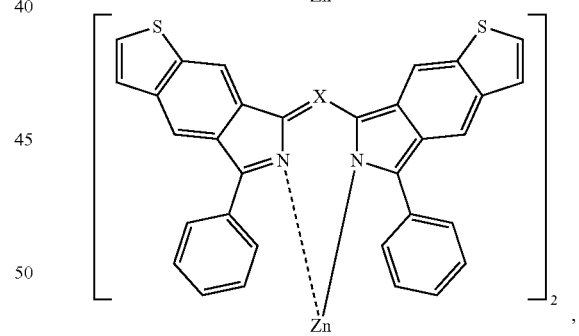
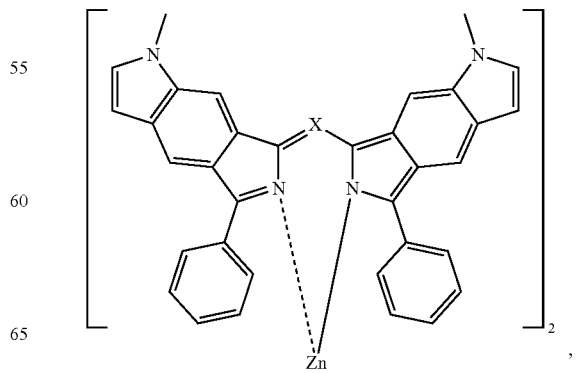

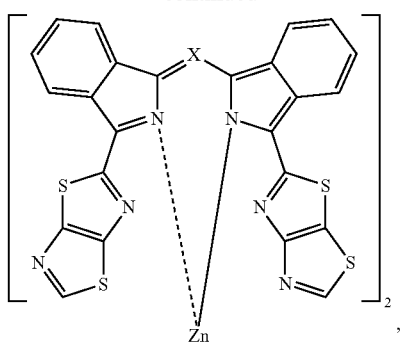
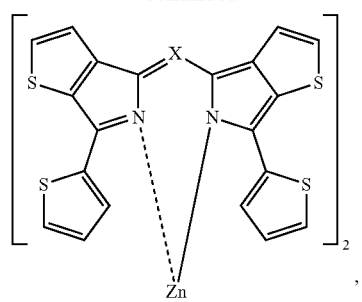
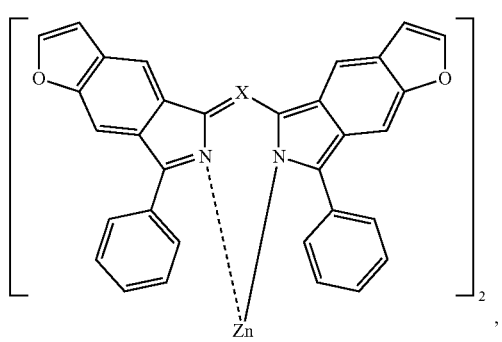
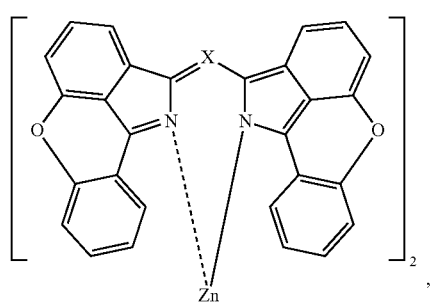
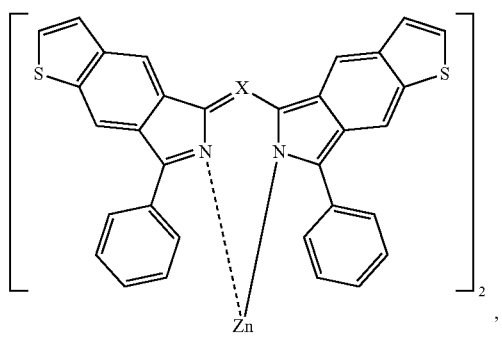
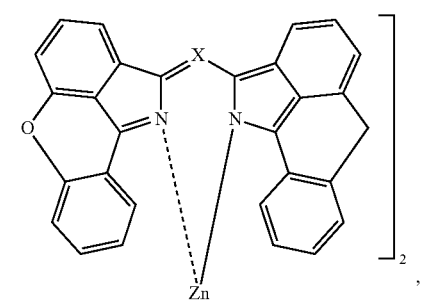
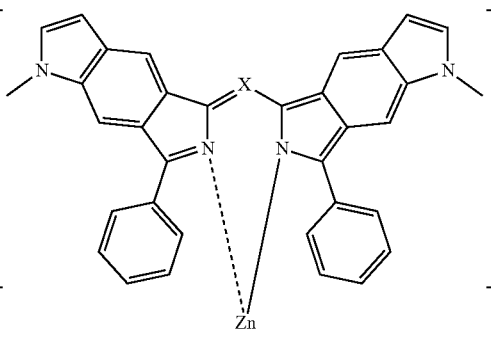
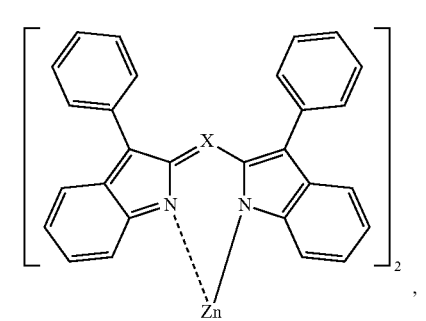
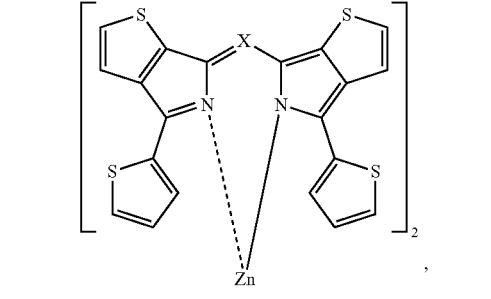
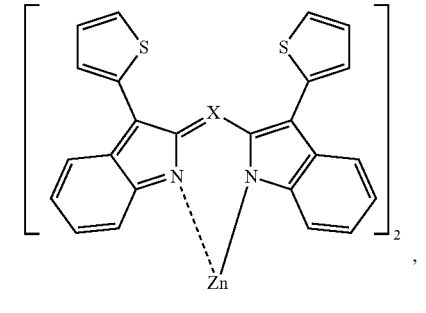

-continued
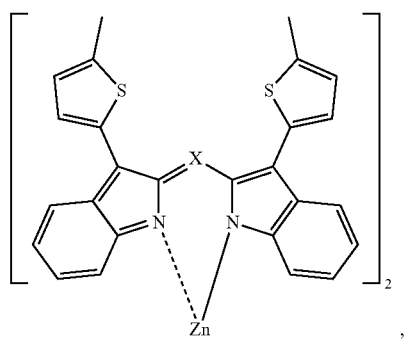
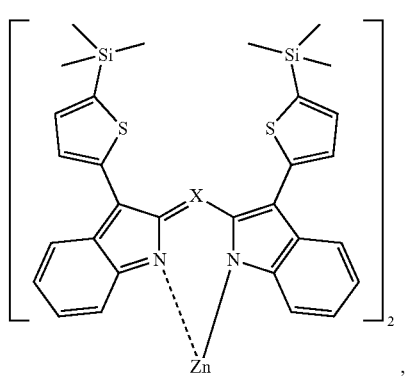
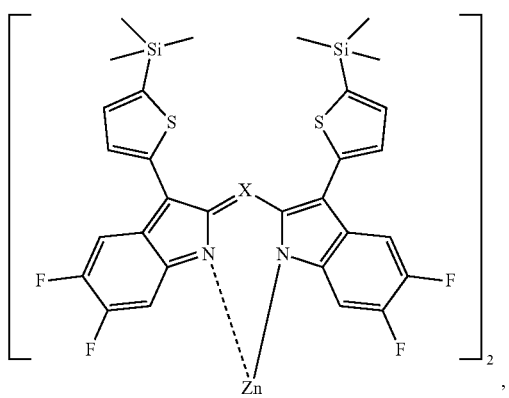
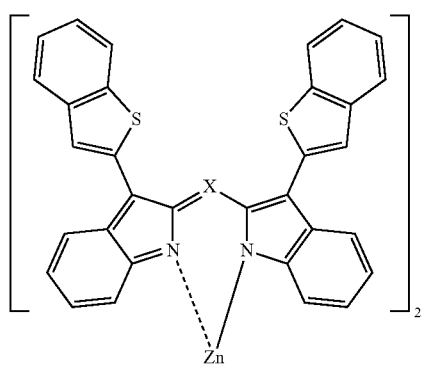
-continued
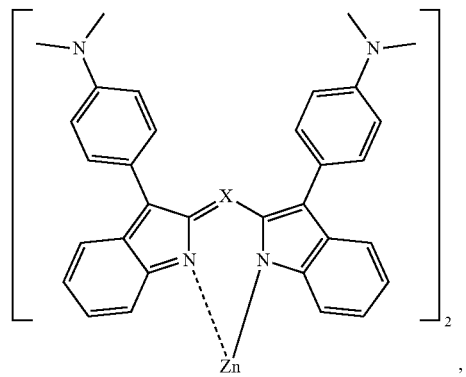
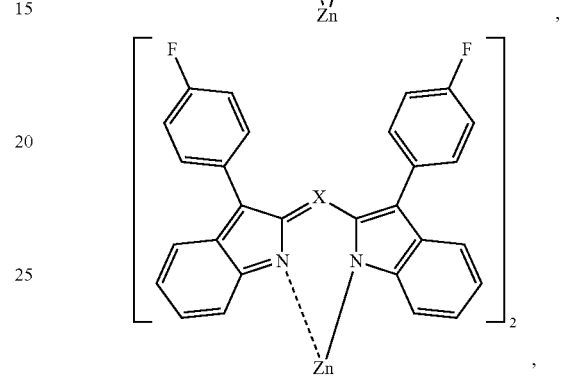
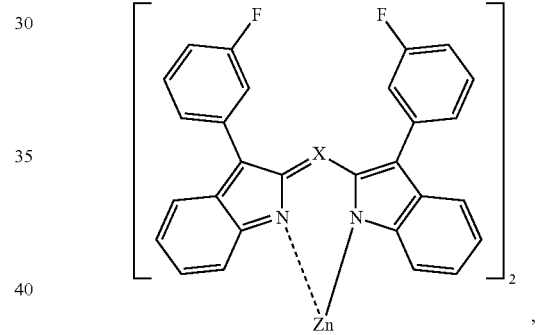
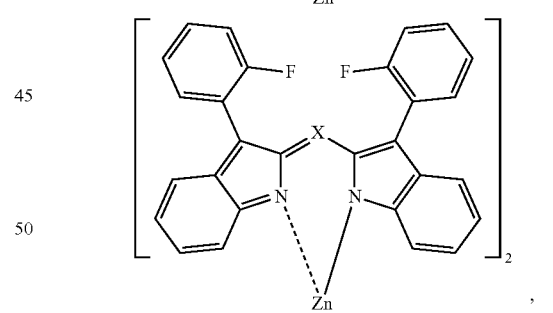
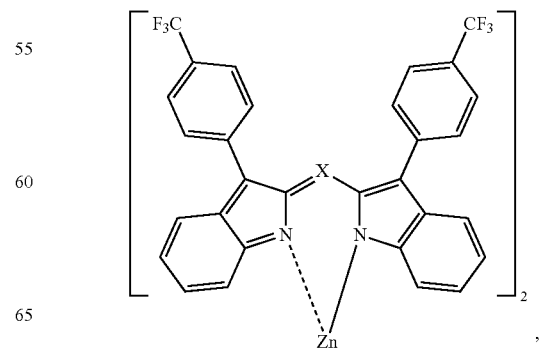

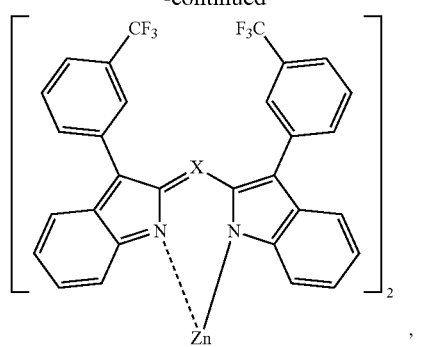,
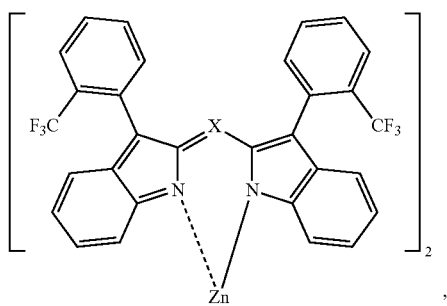,
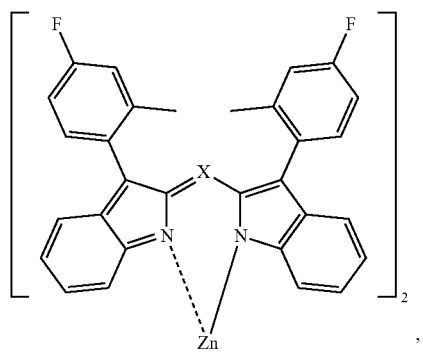,
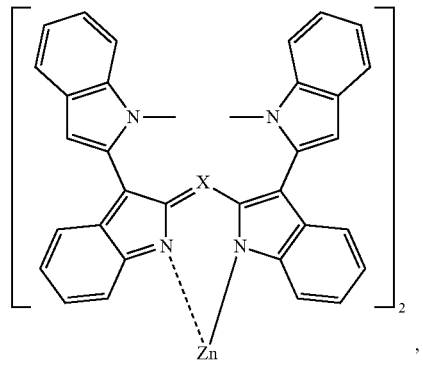,
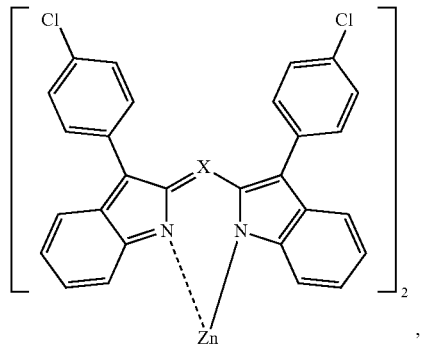,
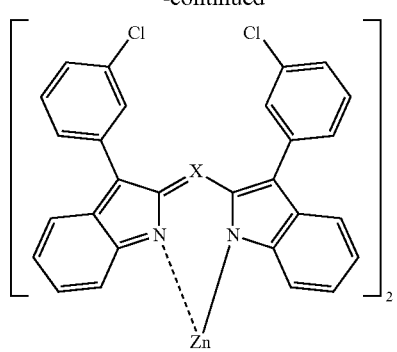,
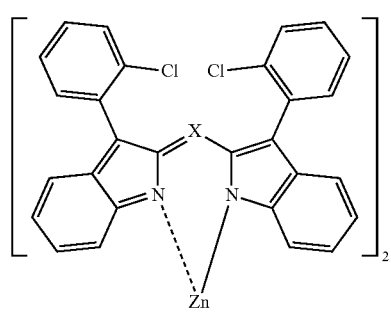,
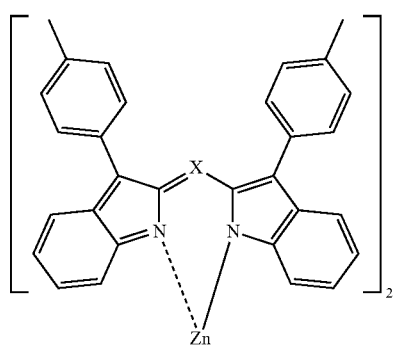,
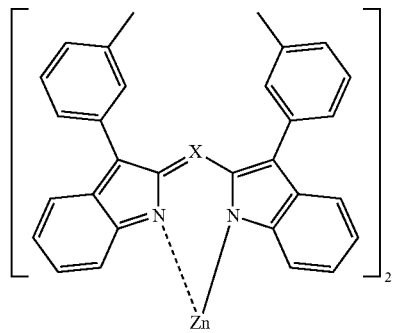,
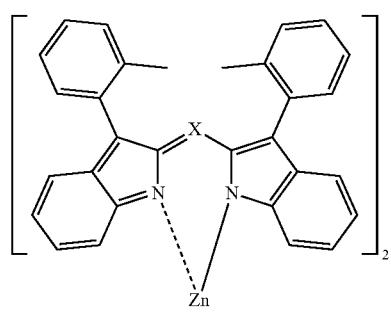,

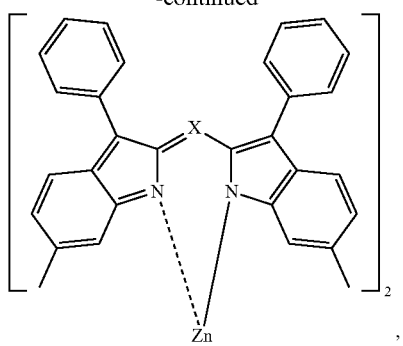
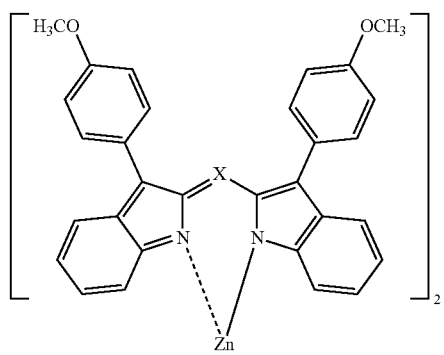
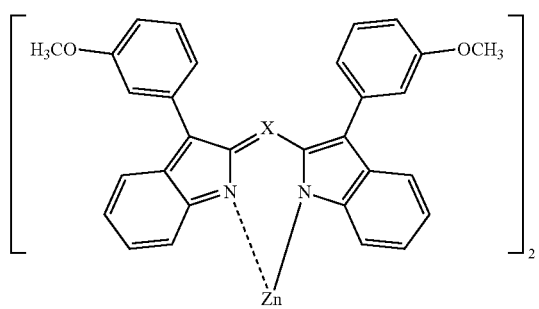
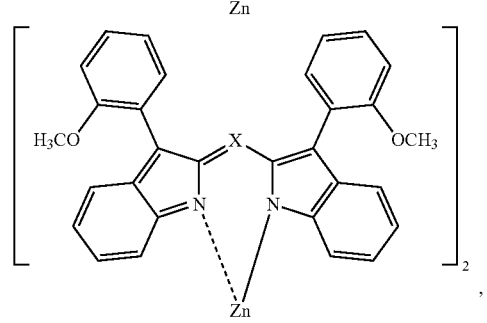
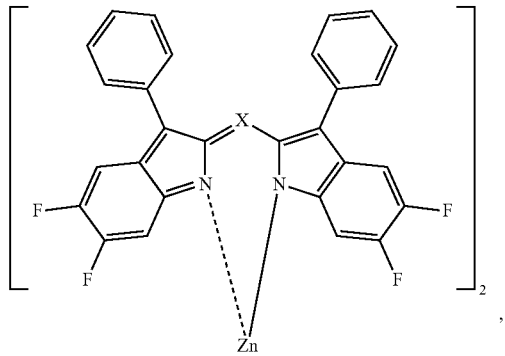
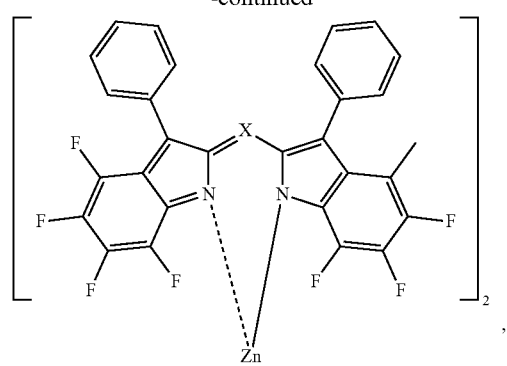
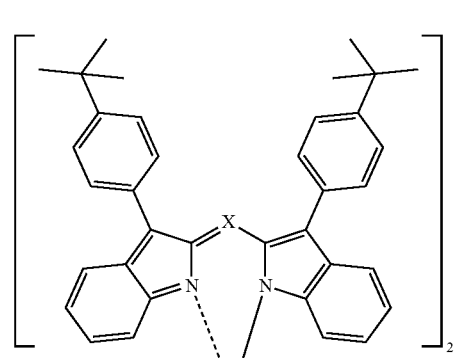
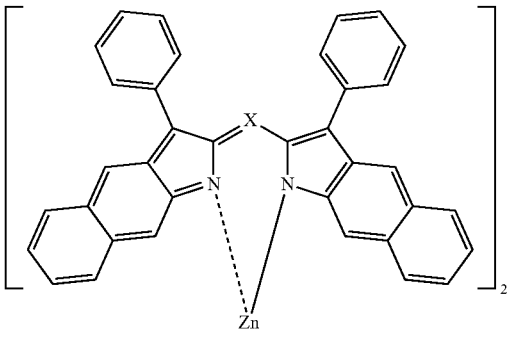
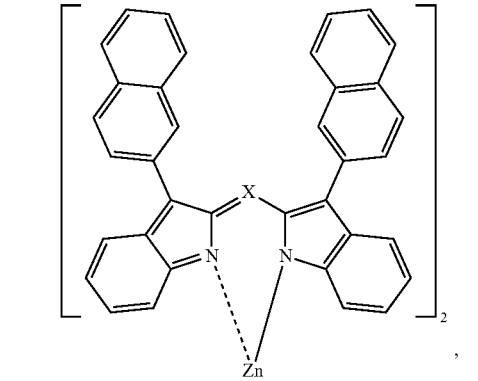

53
-continued
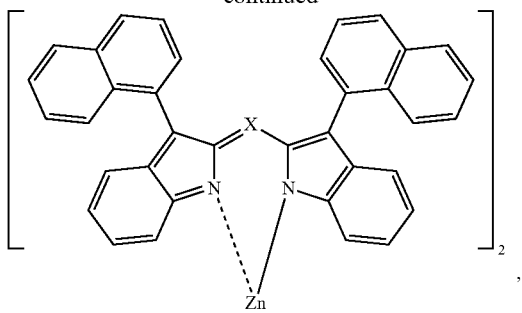
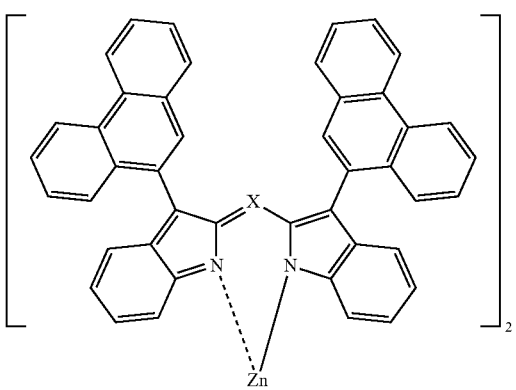
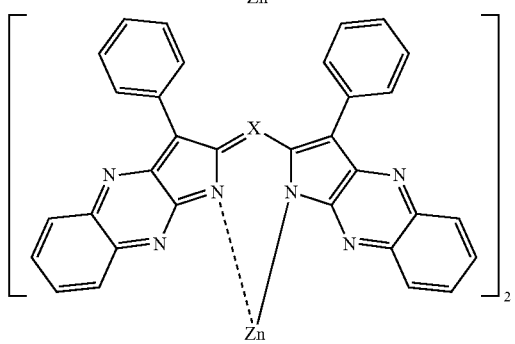
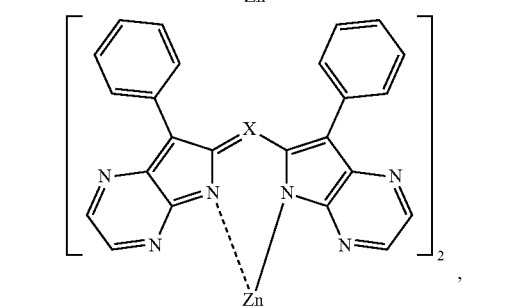
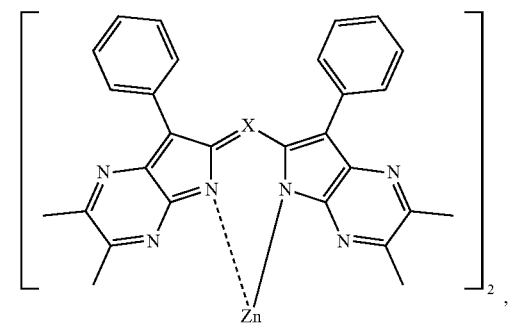
54
-continued
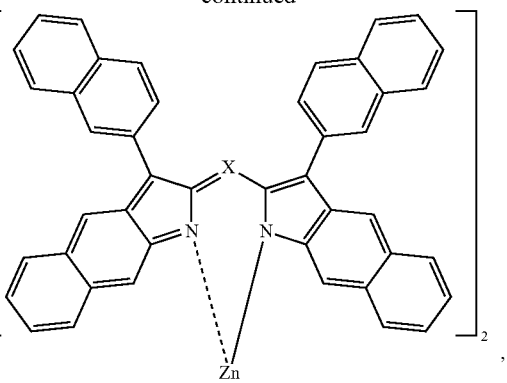
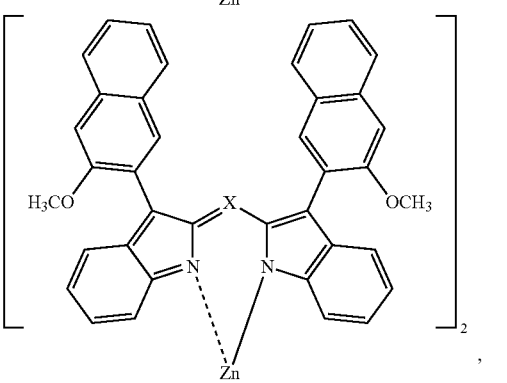
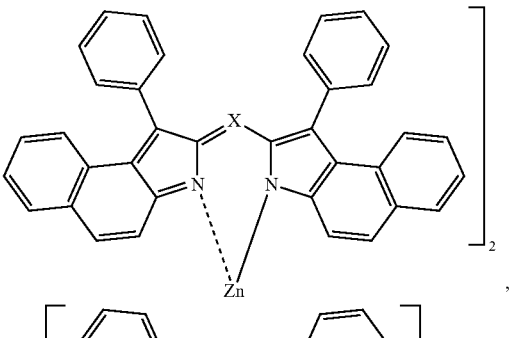
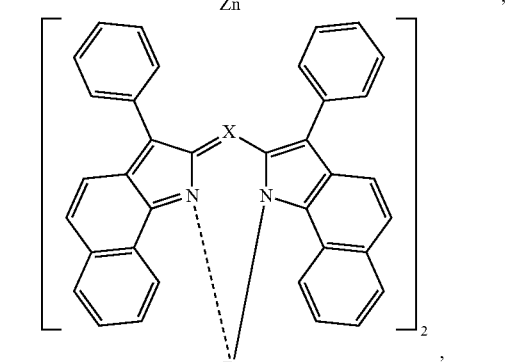
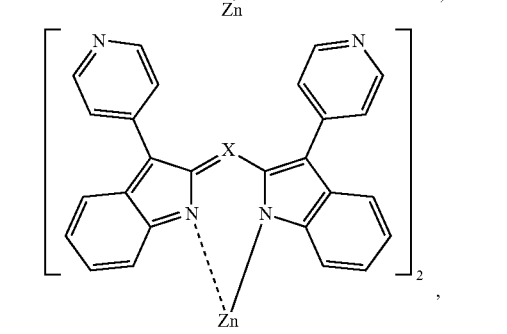

-continued
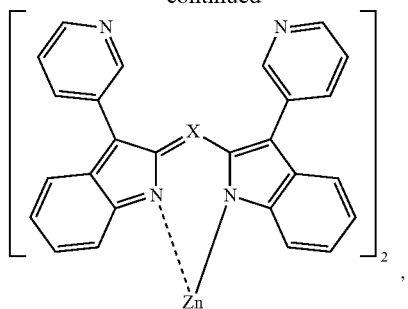
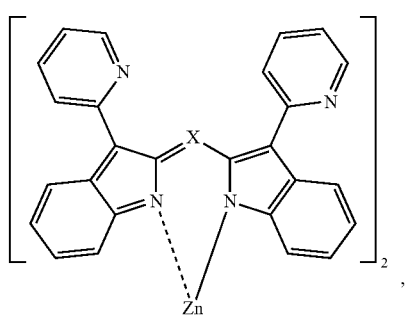
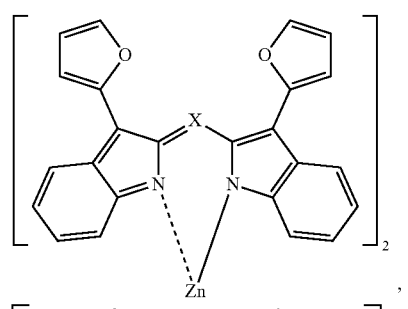
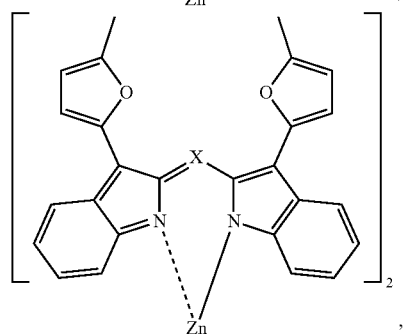
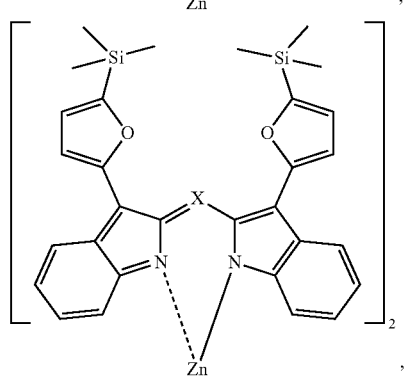
-continued
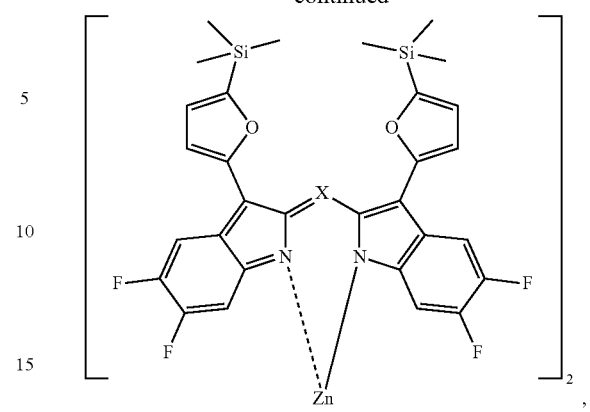
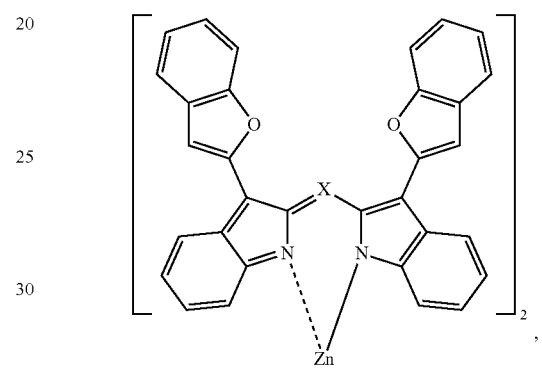
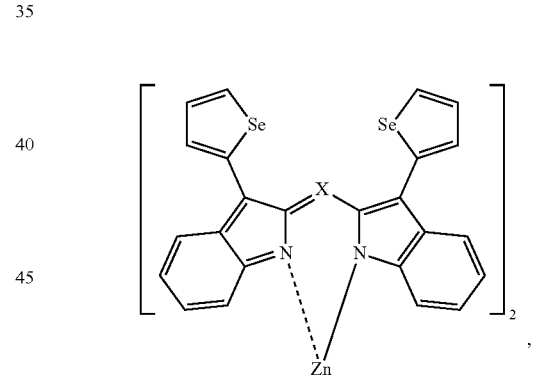
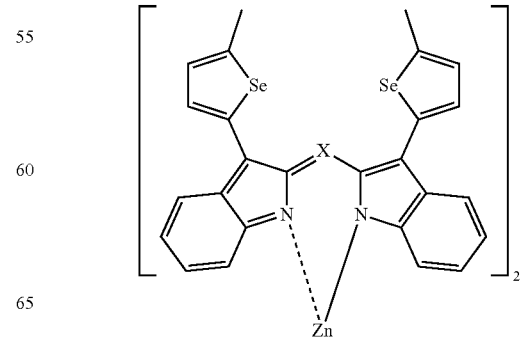

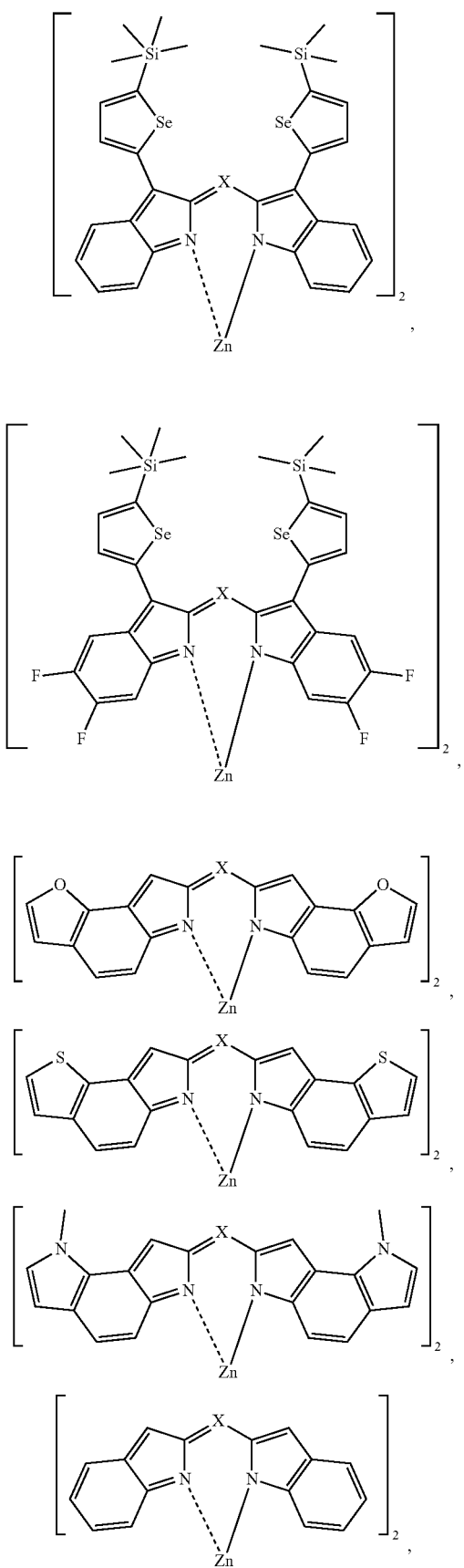
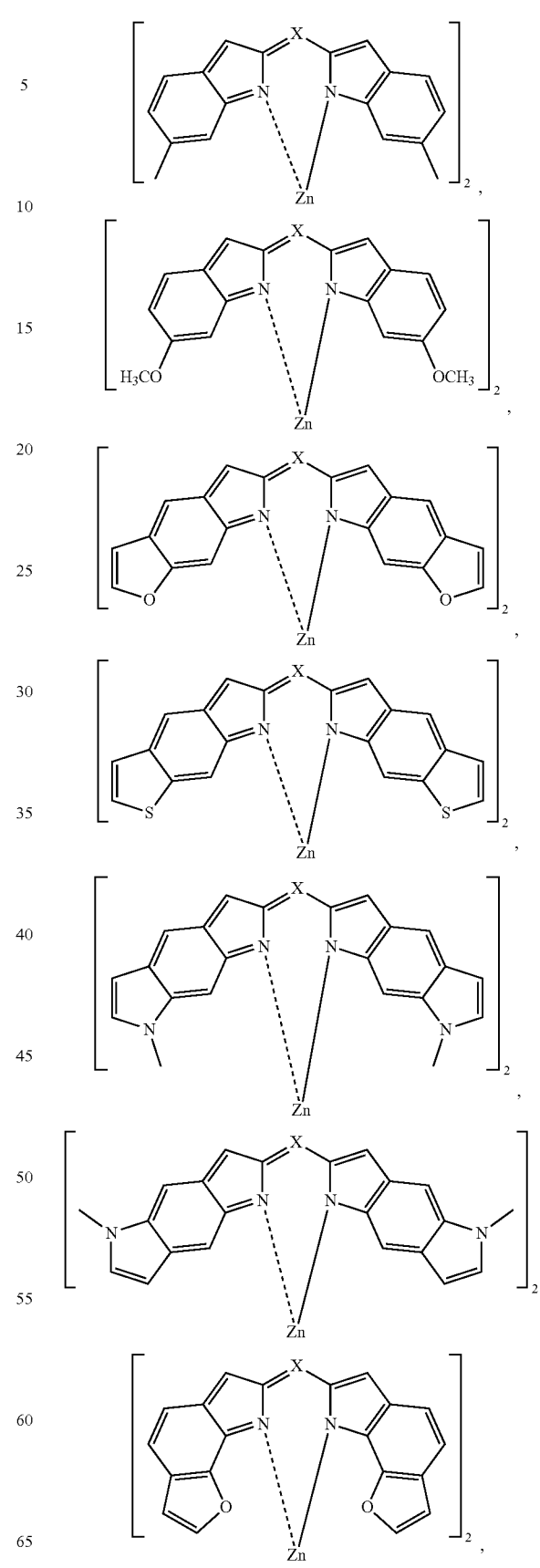

-continued
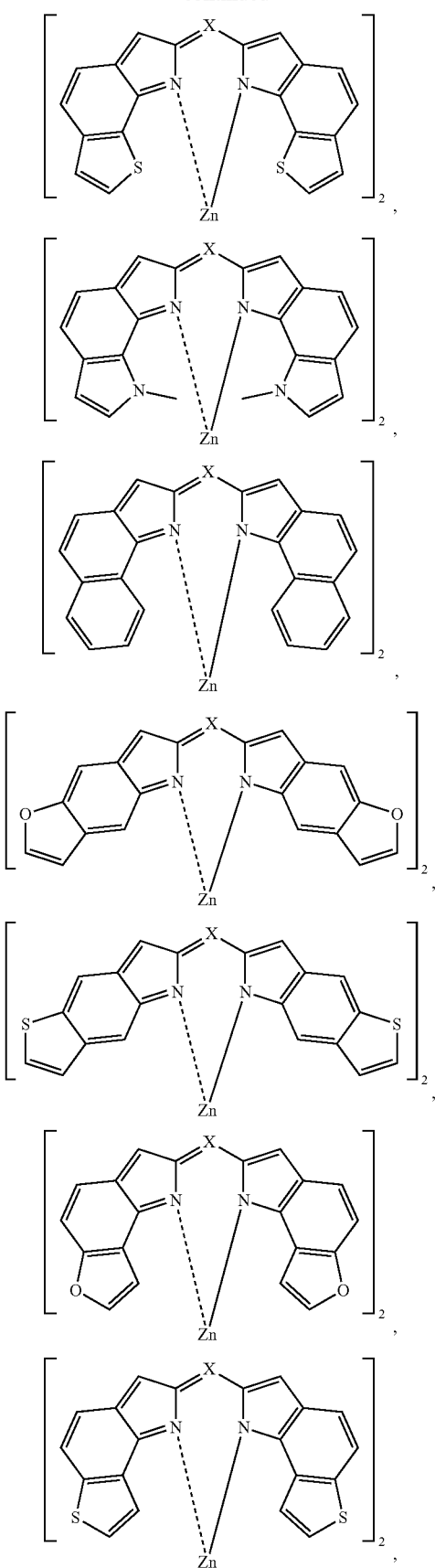
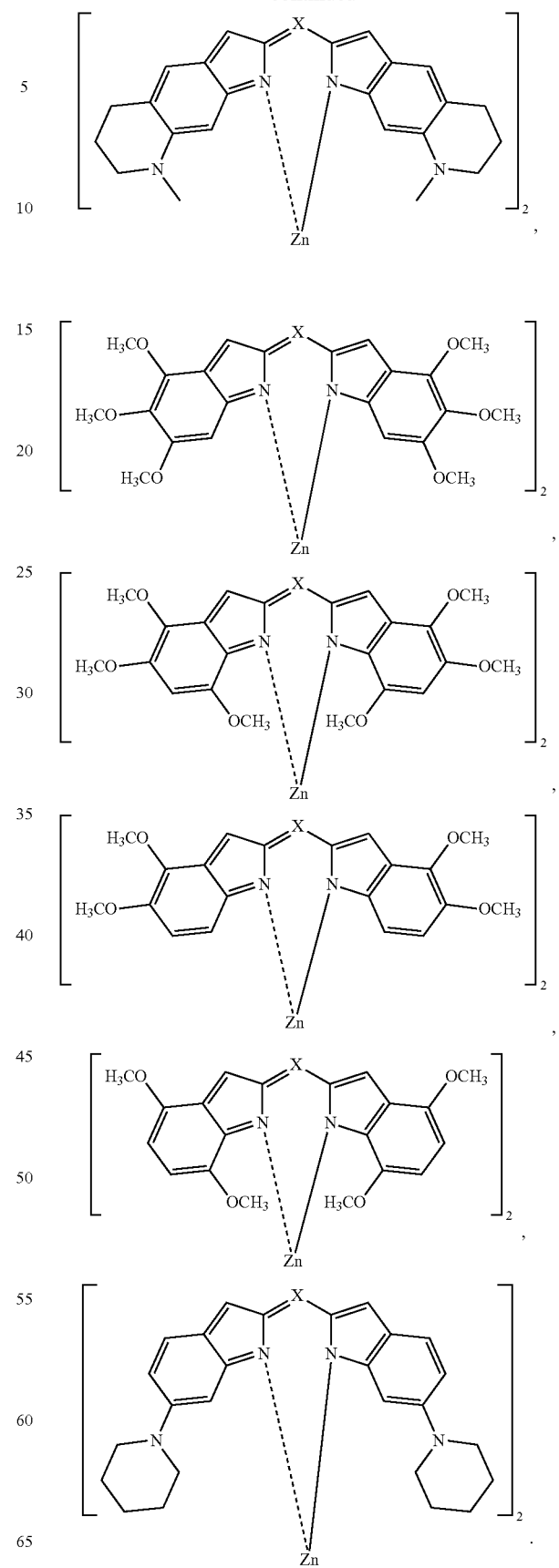

-continued
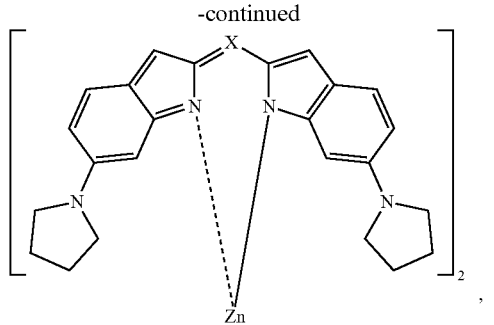
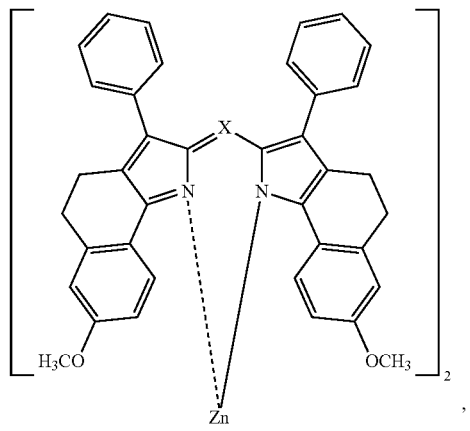
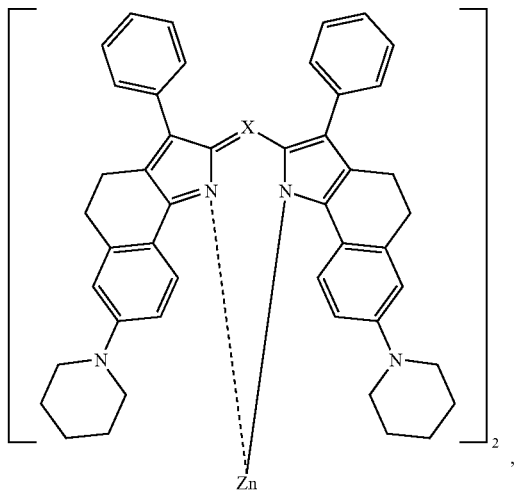
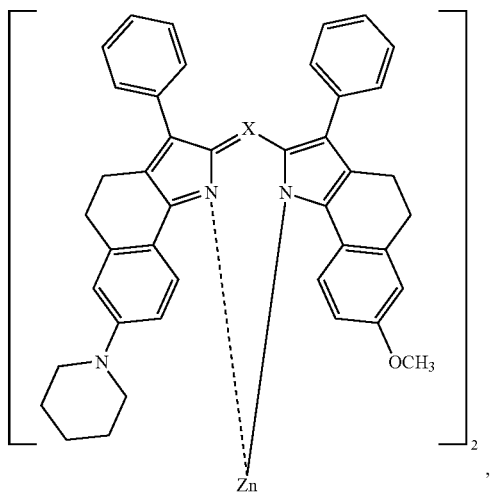
-continued
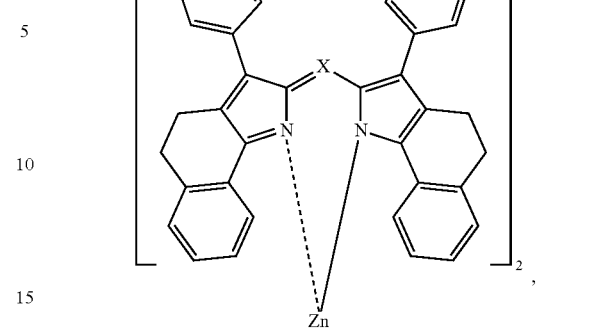
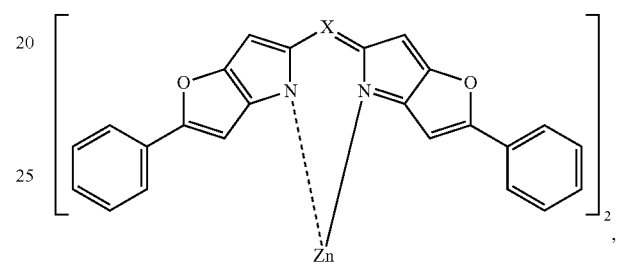
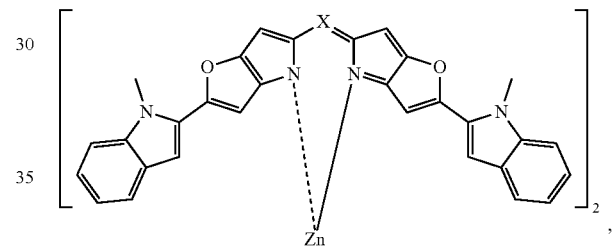
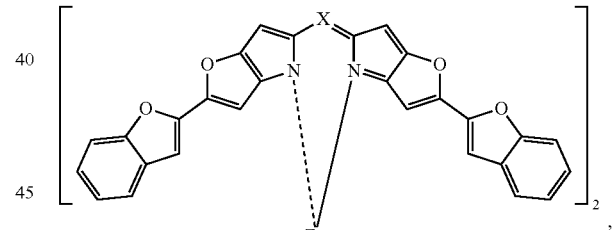
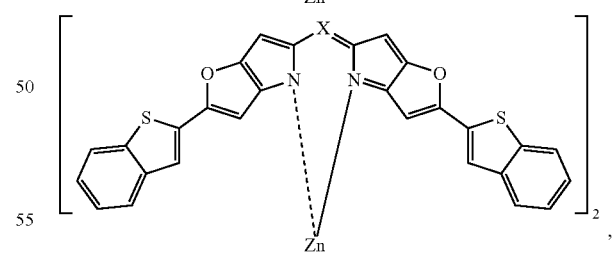
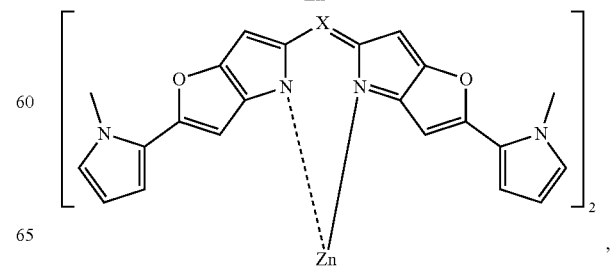

63
-continued
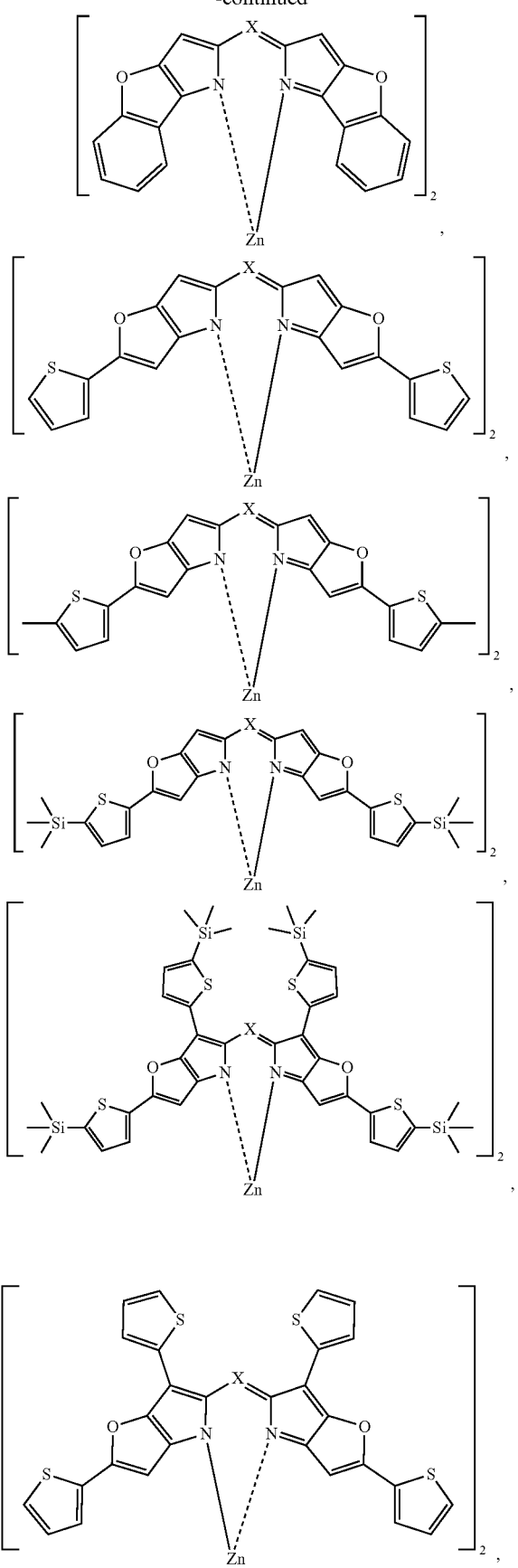
64
-continued
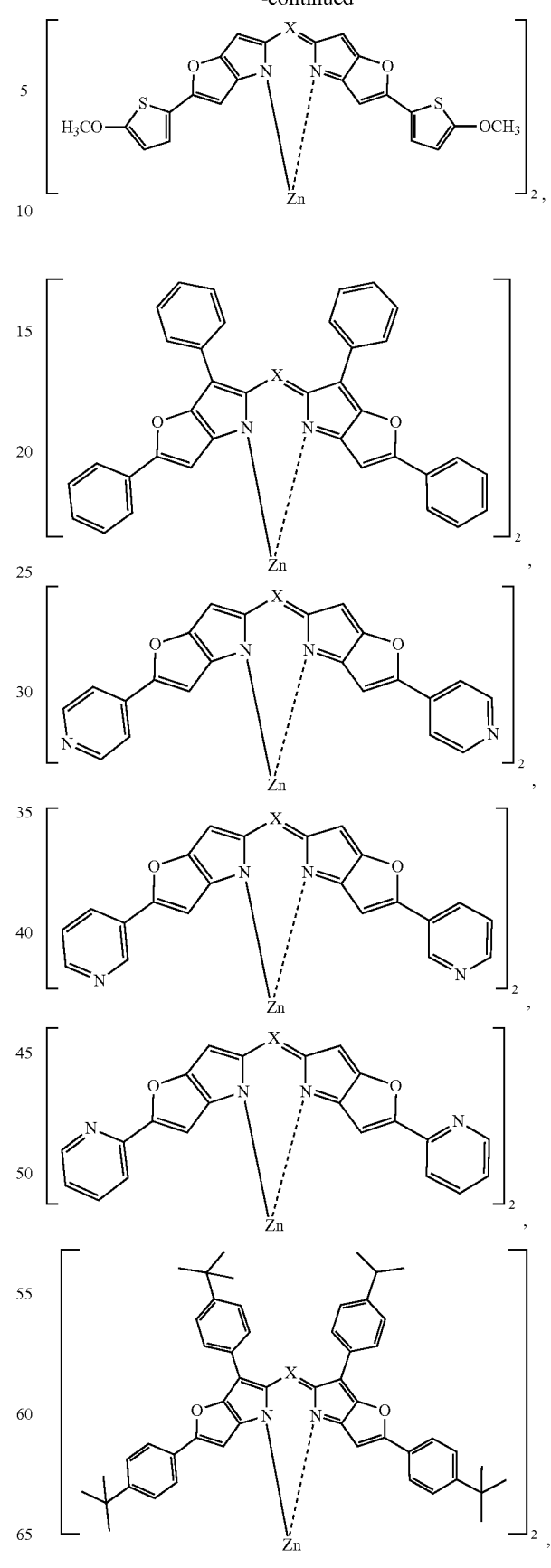

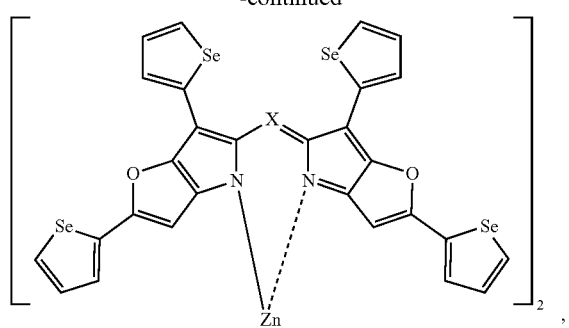
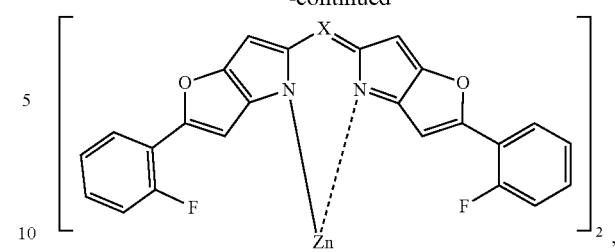
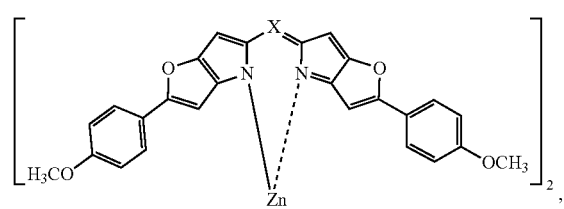
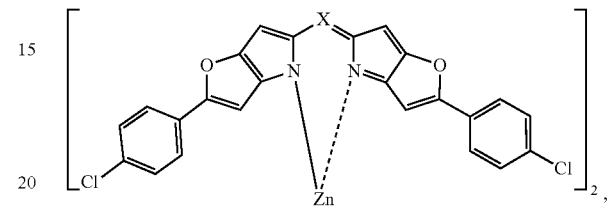
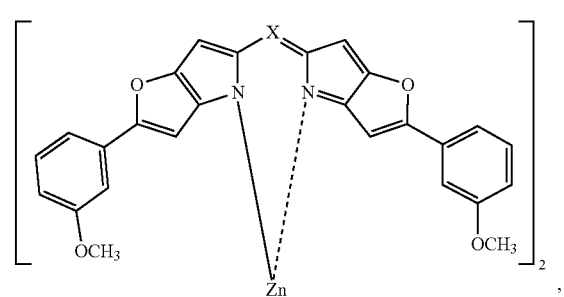
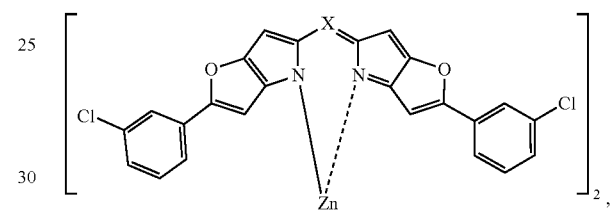
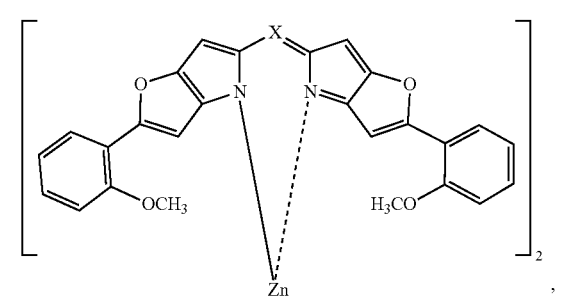
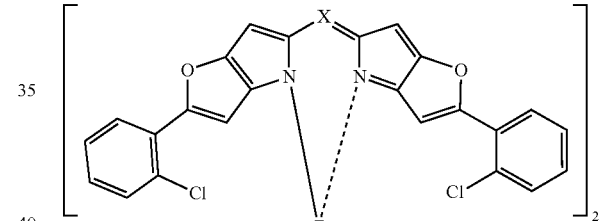
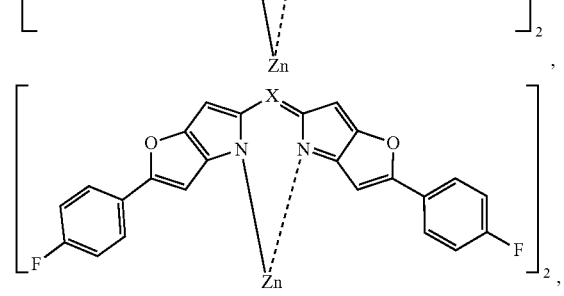
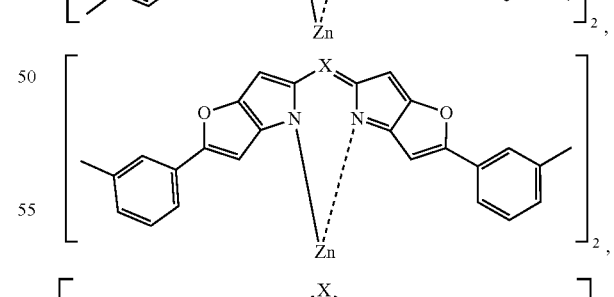
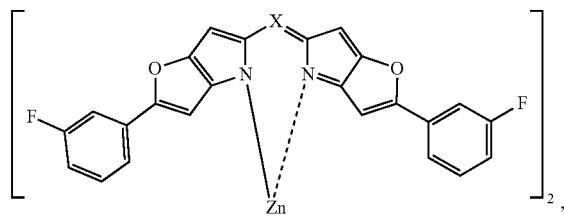
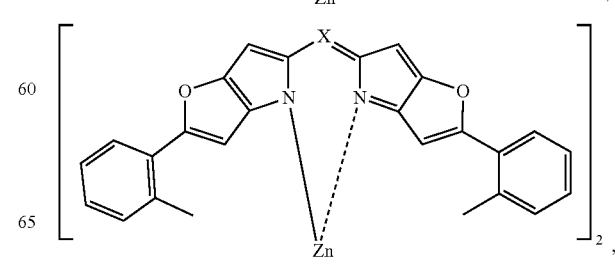

-continued
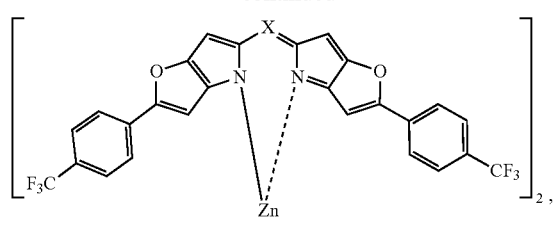
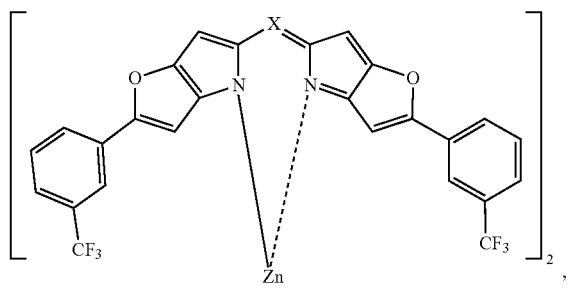
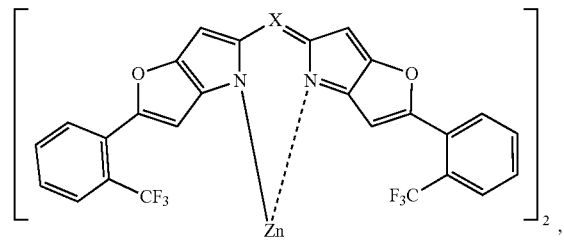
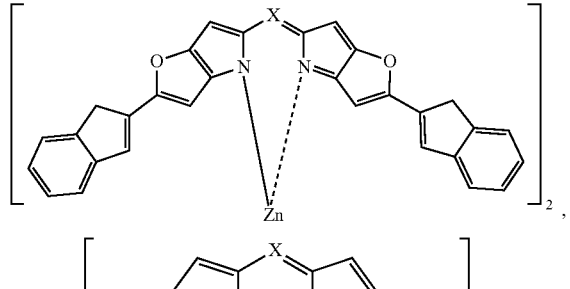
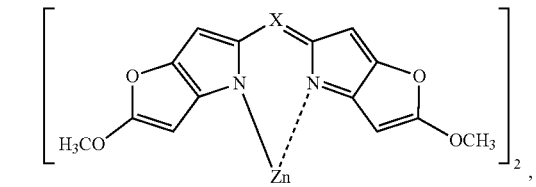
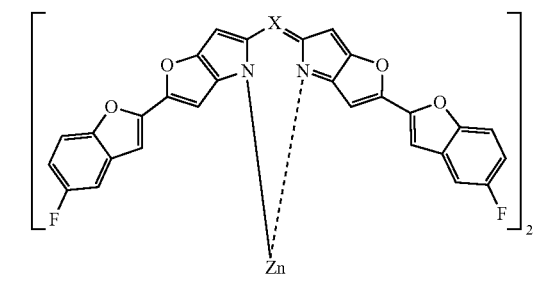
-continued
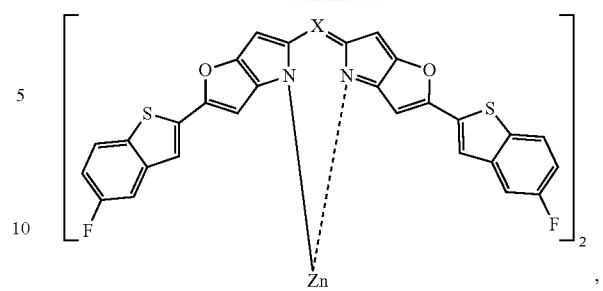
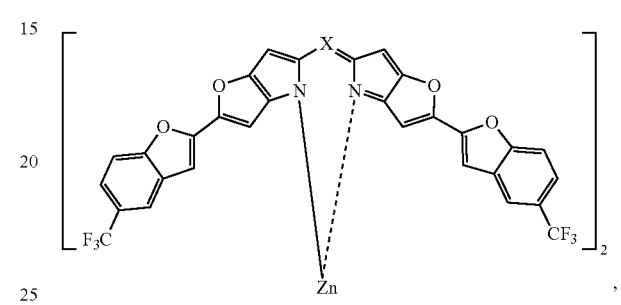
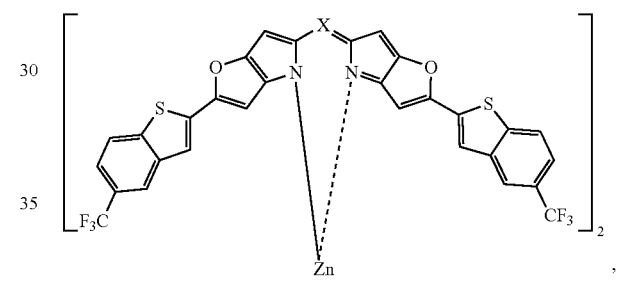
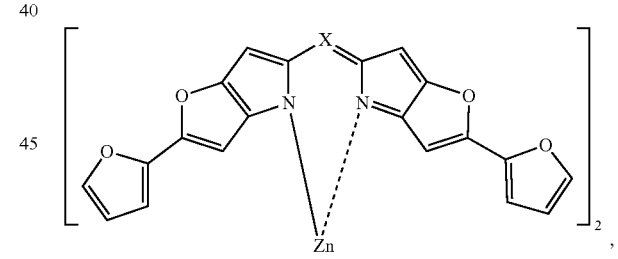
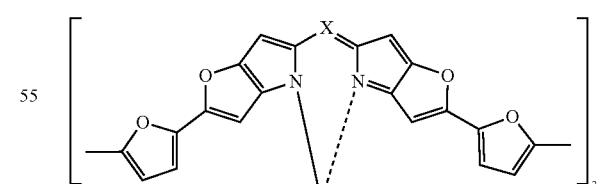
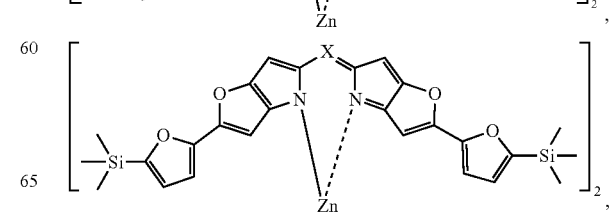

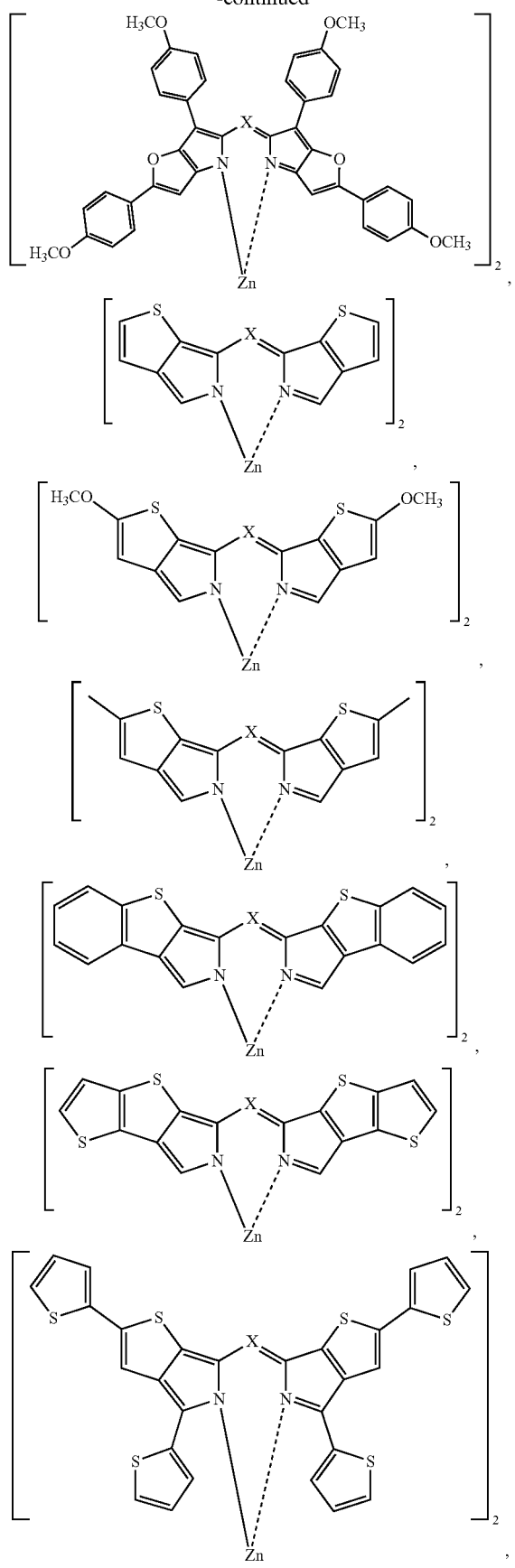
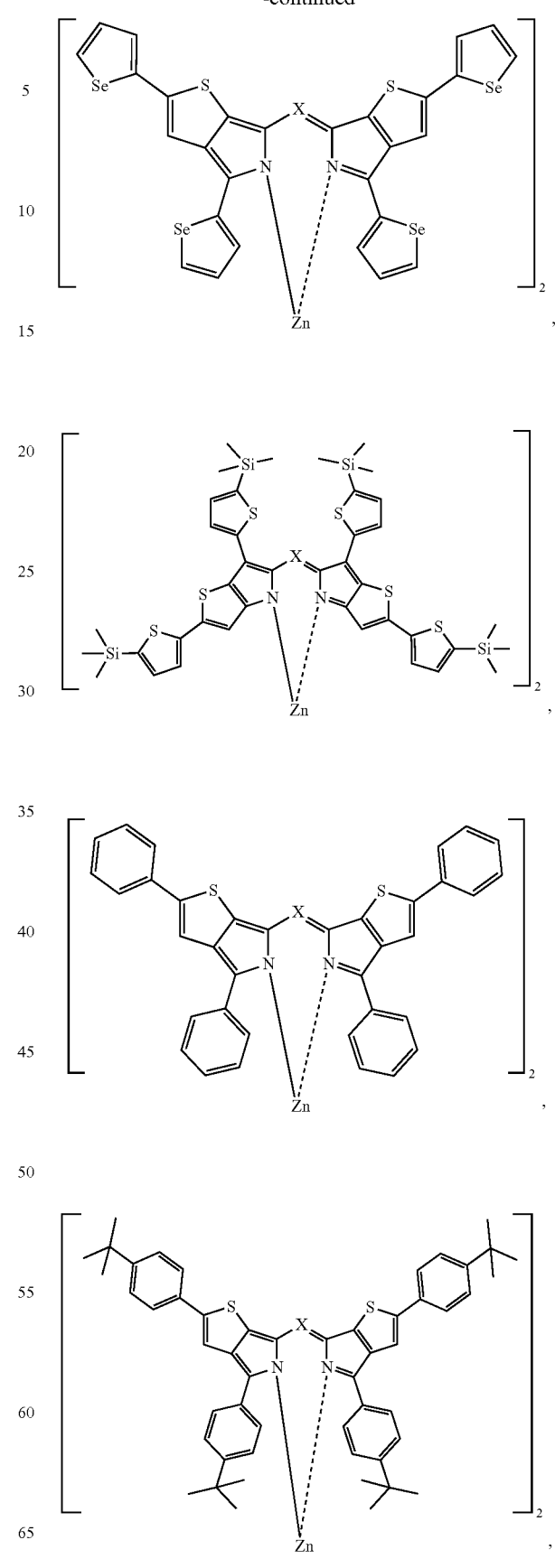

-continued
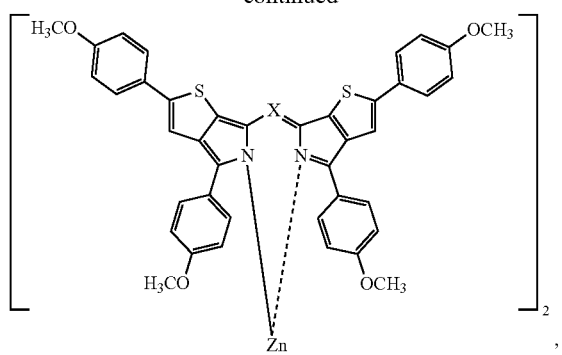
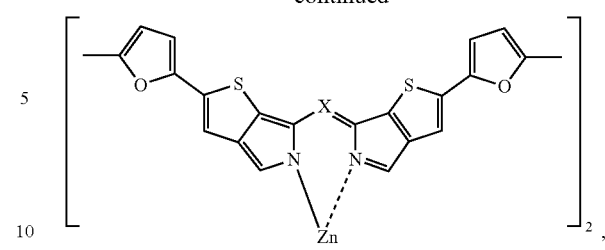
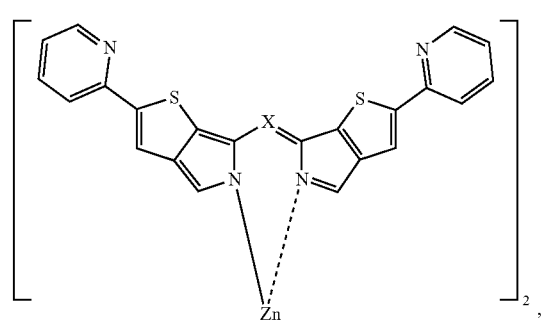
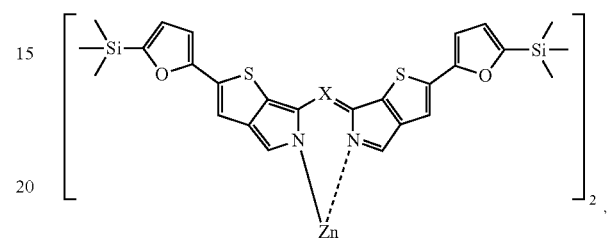
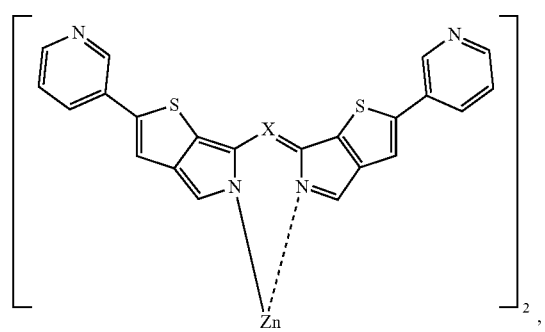
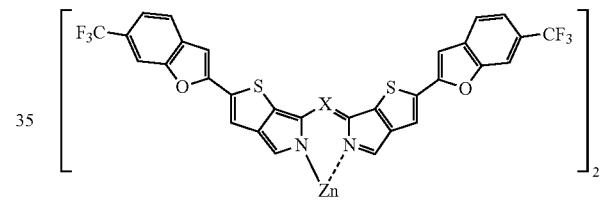
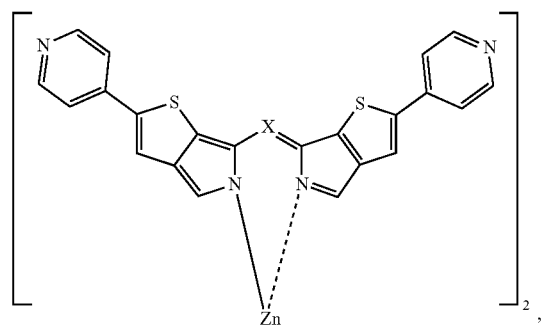
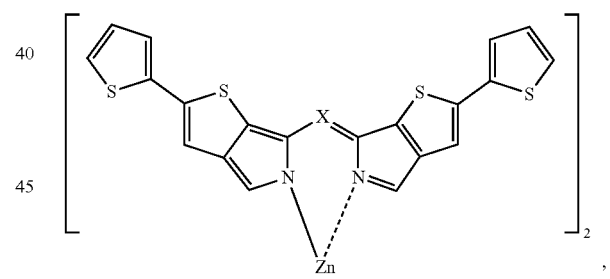
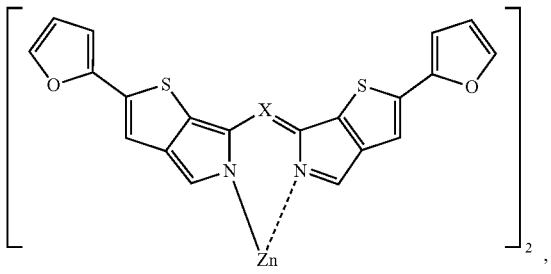
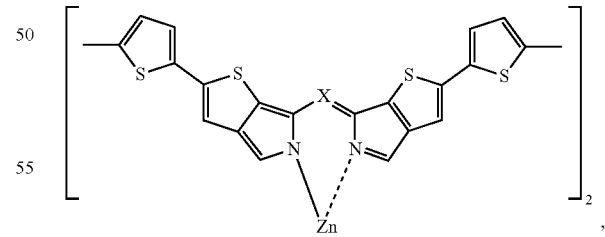
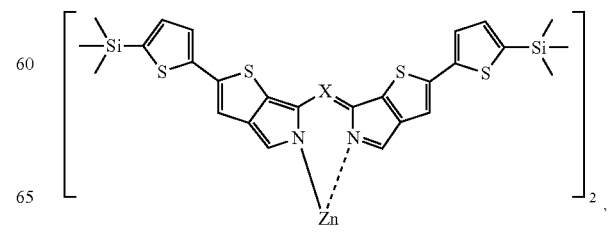

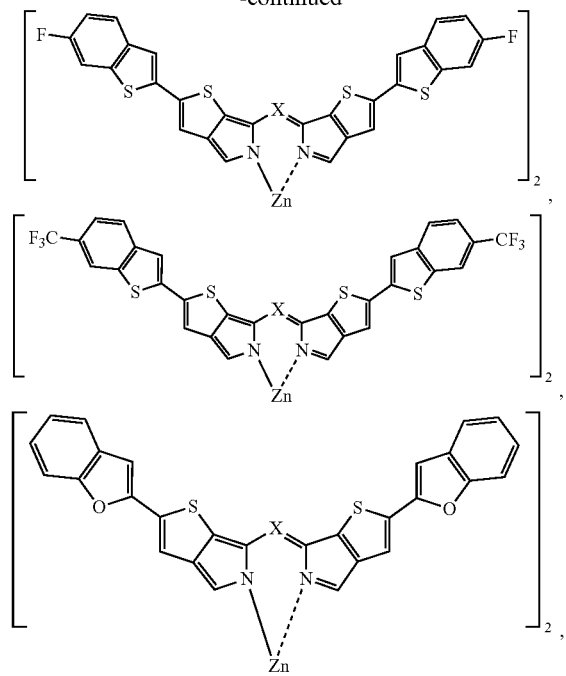

75
-continued
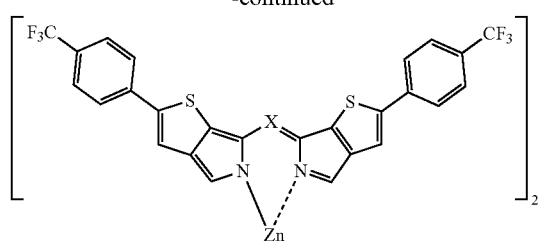
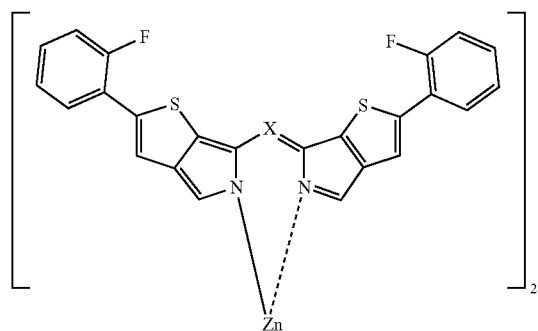
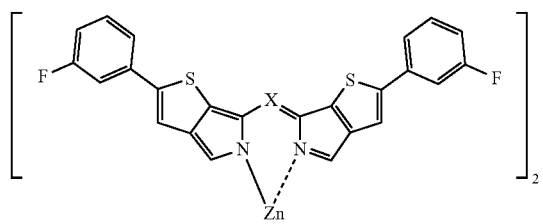
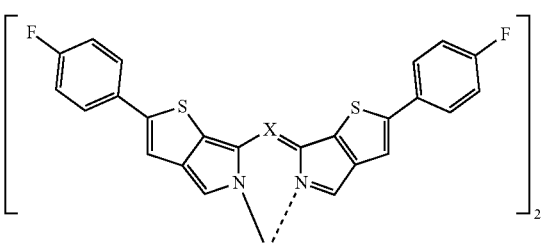
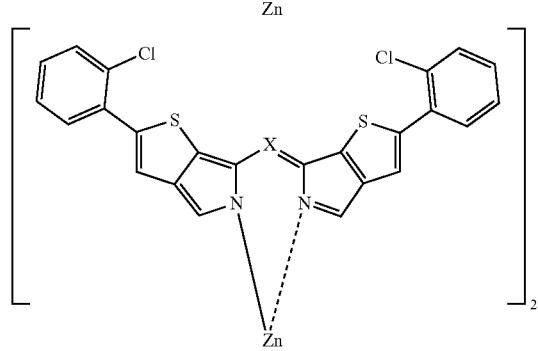
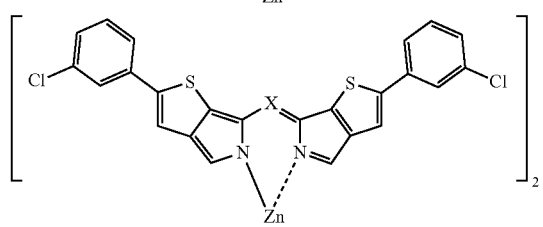
76
-continued
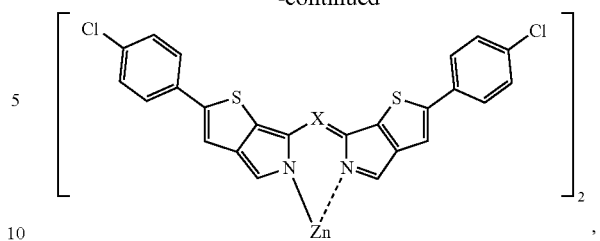
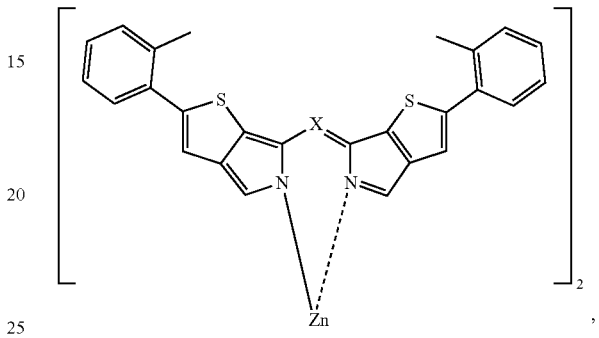
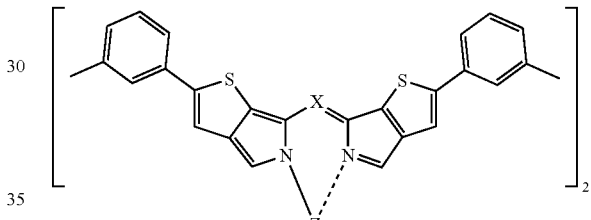
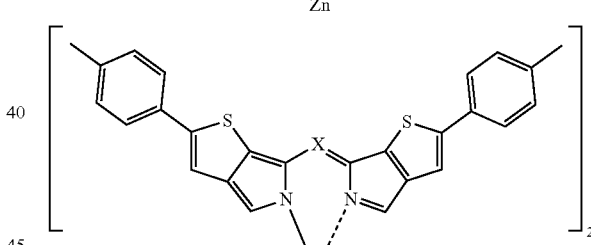
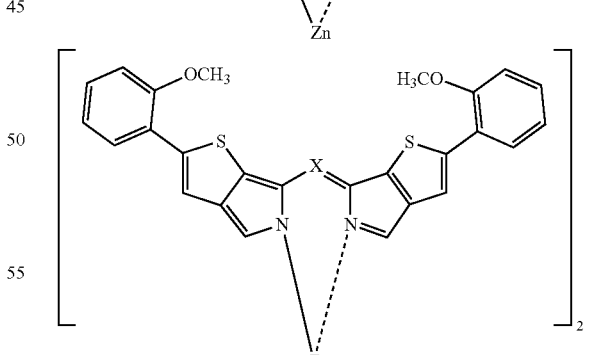
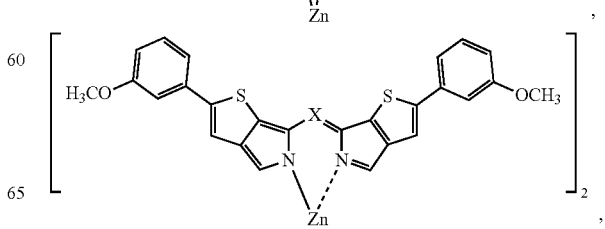

77
-continued
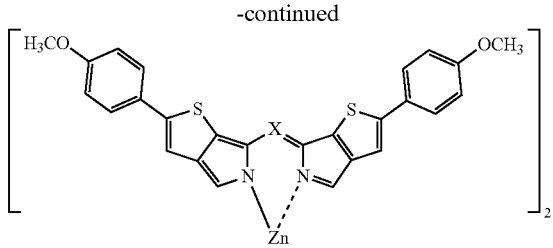
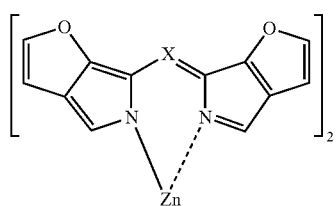
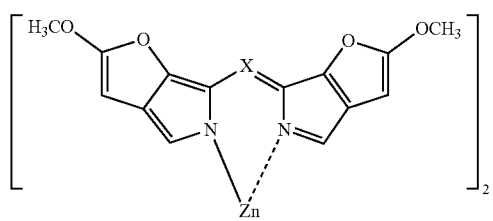
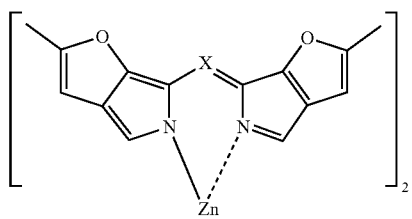
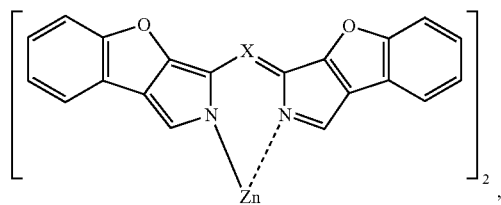
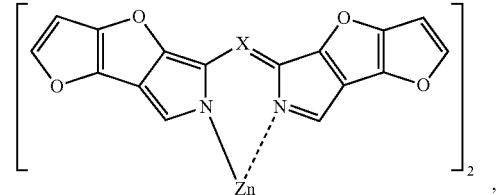
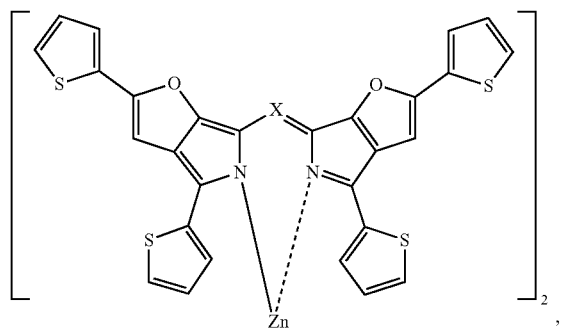
78
-continued
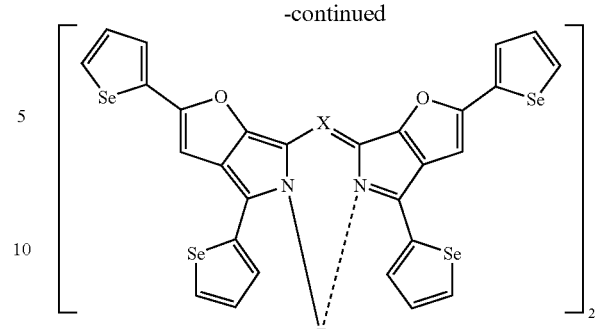
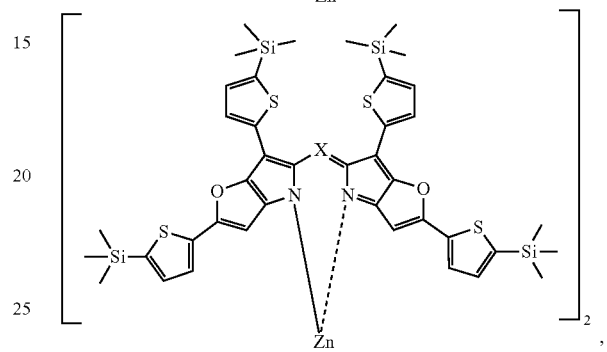
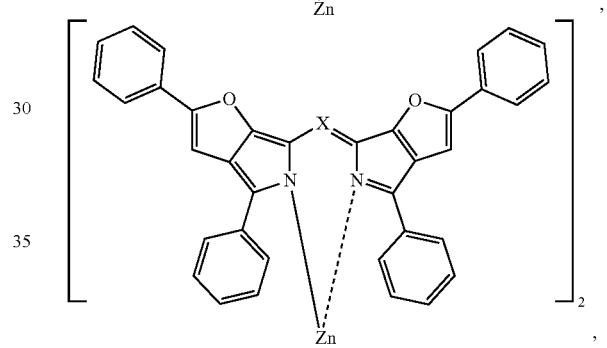
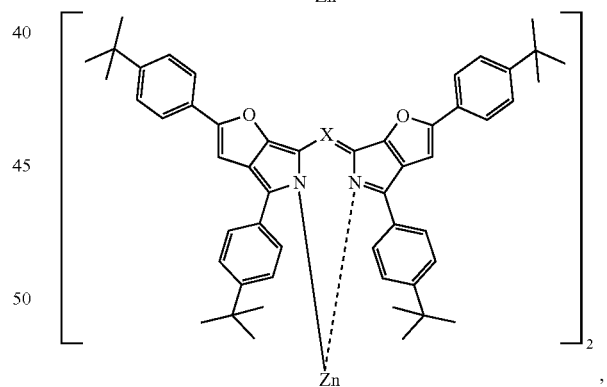
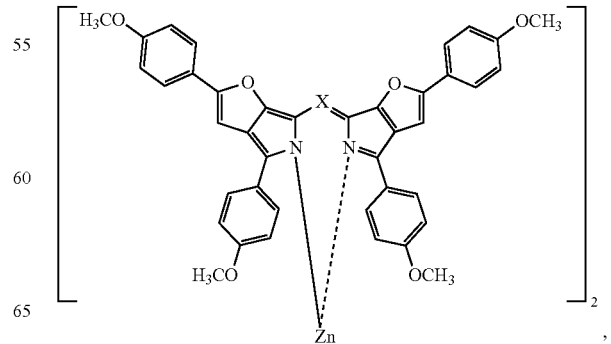

-continued
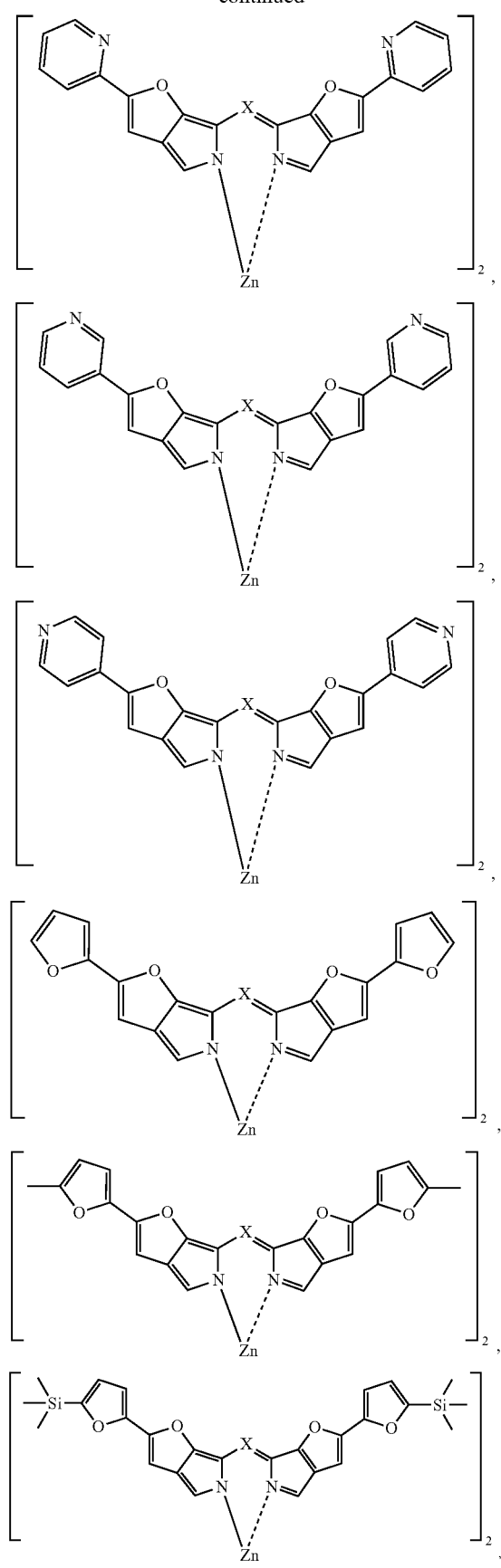
-continued
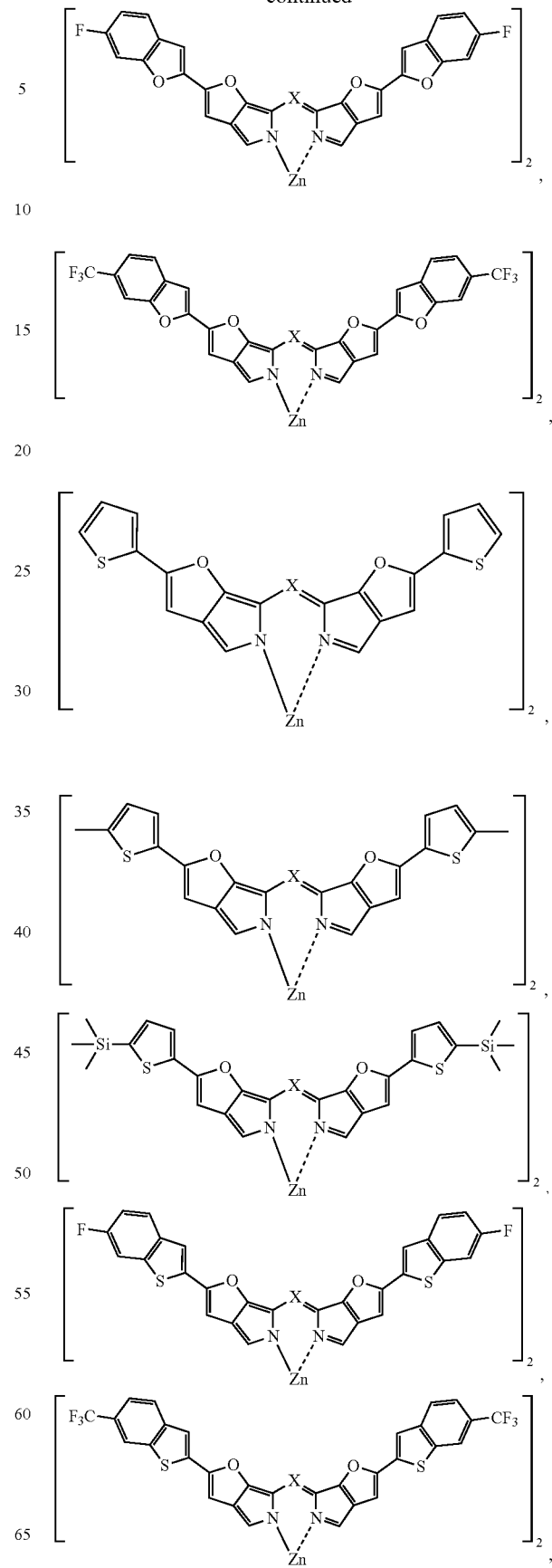

81
-continued
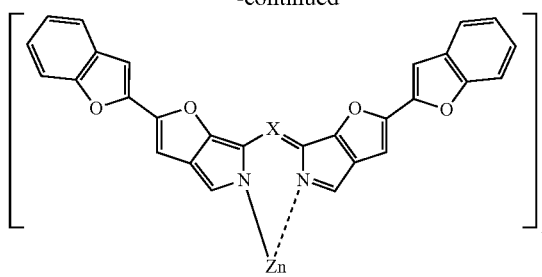
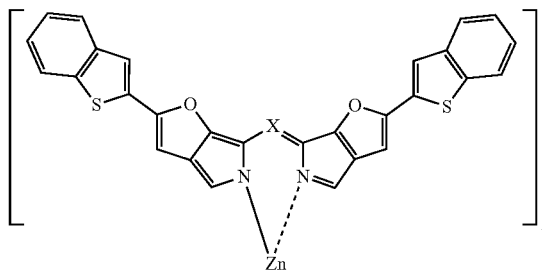
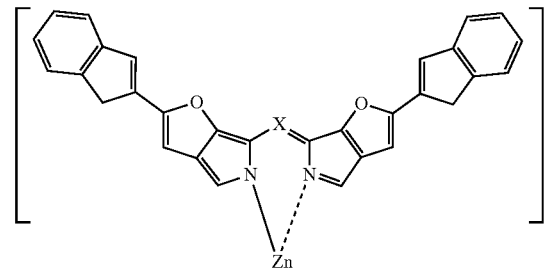
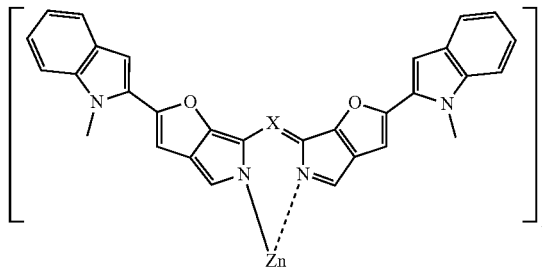
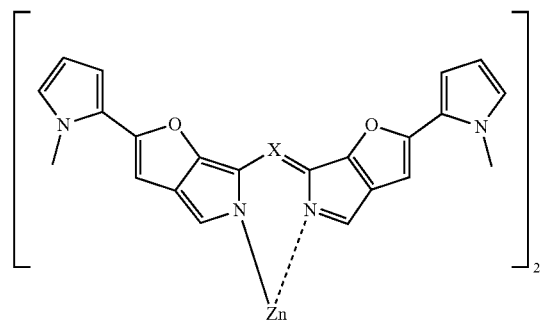
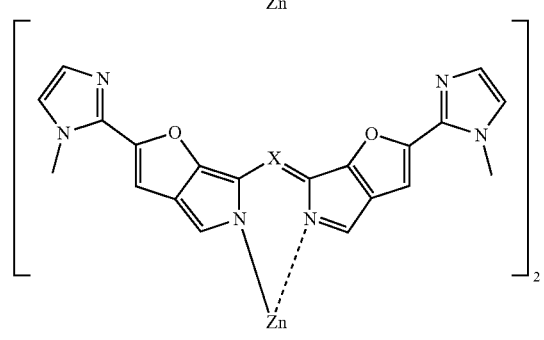
82
-continued
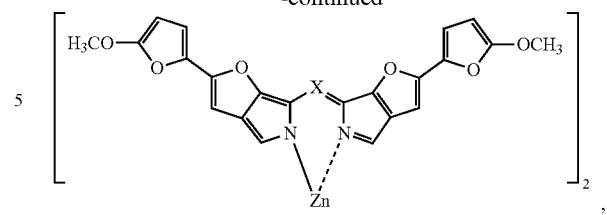
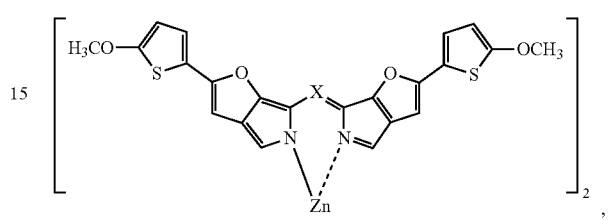
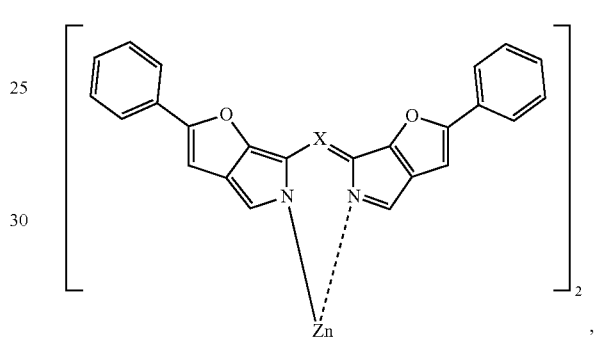
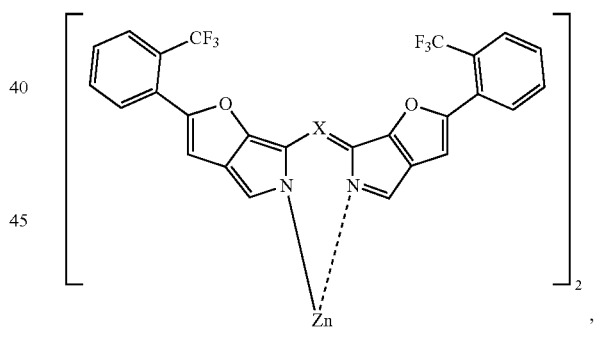
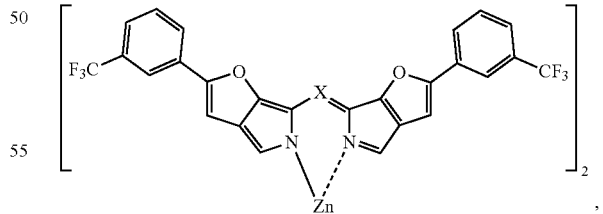
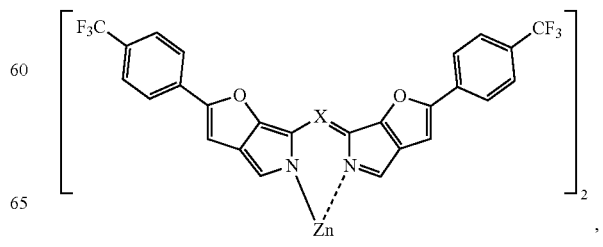

-continued
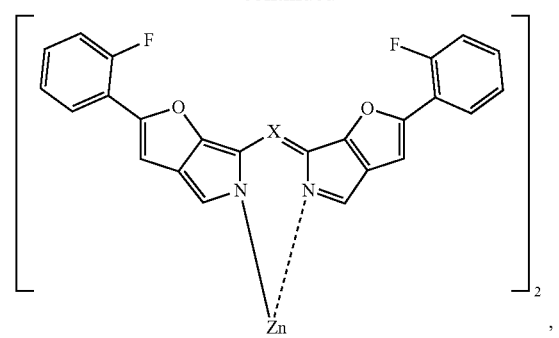
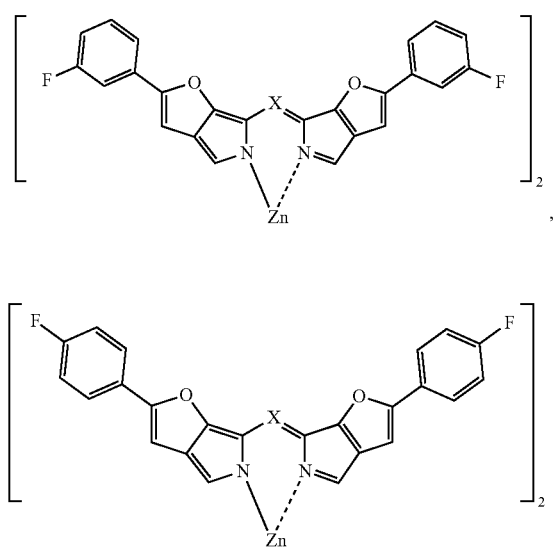
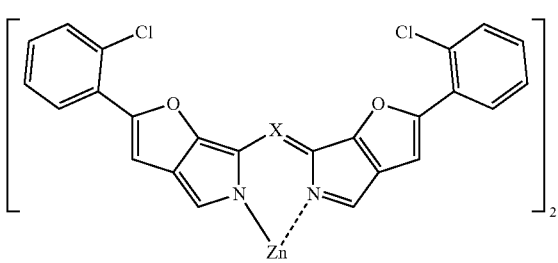
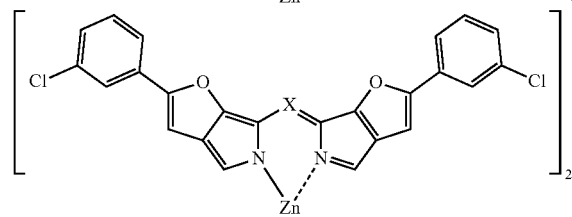
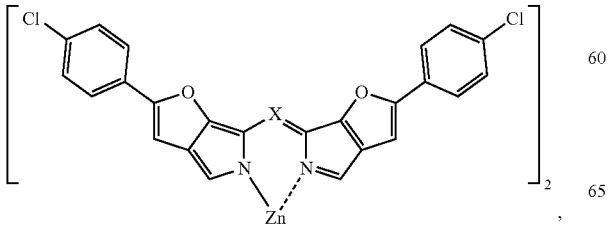
-continued
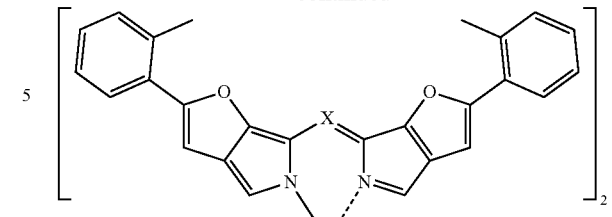
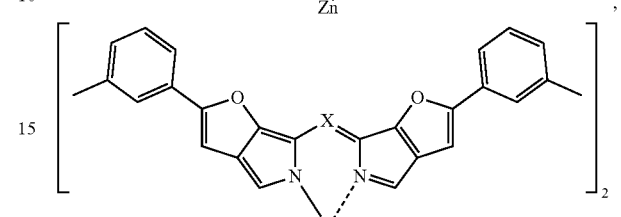
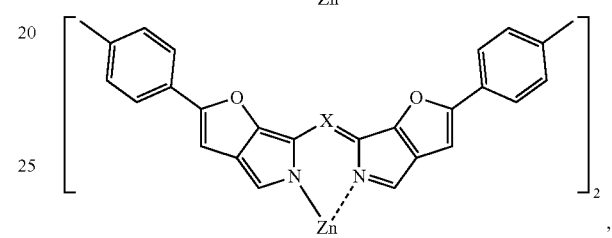
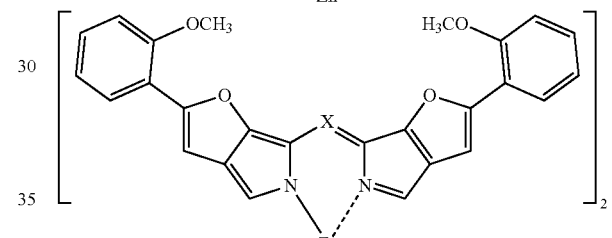
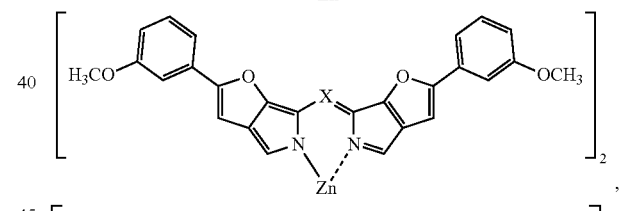
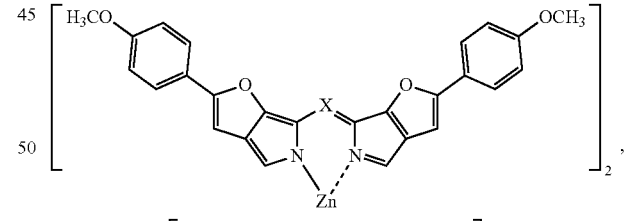
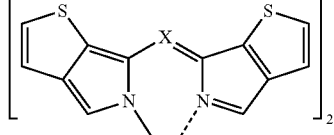
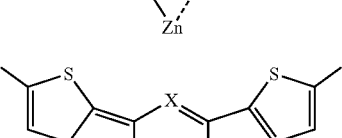
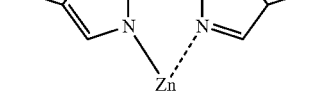

85
-continued
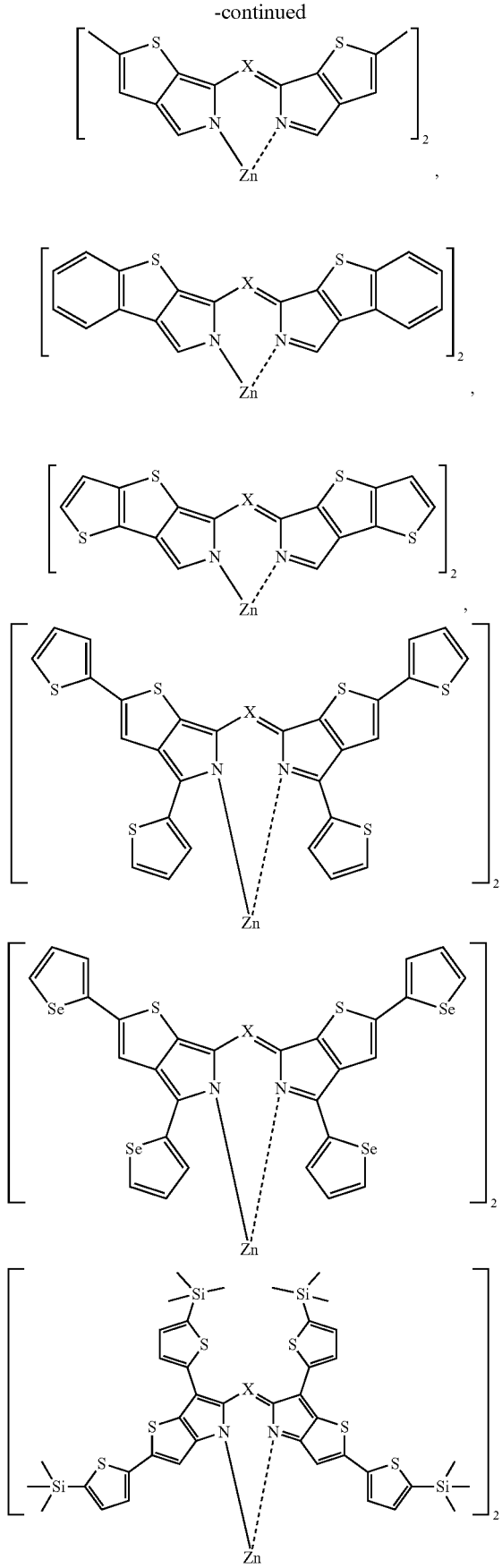
86
-continued
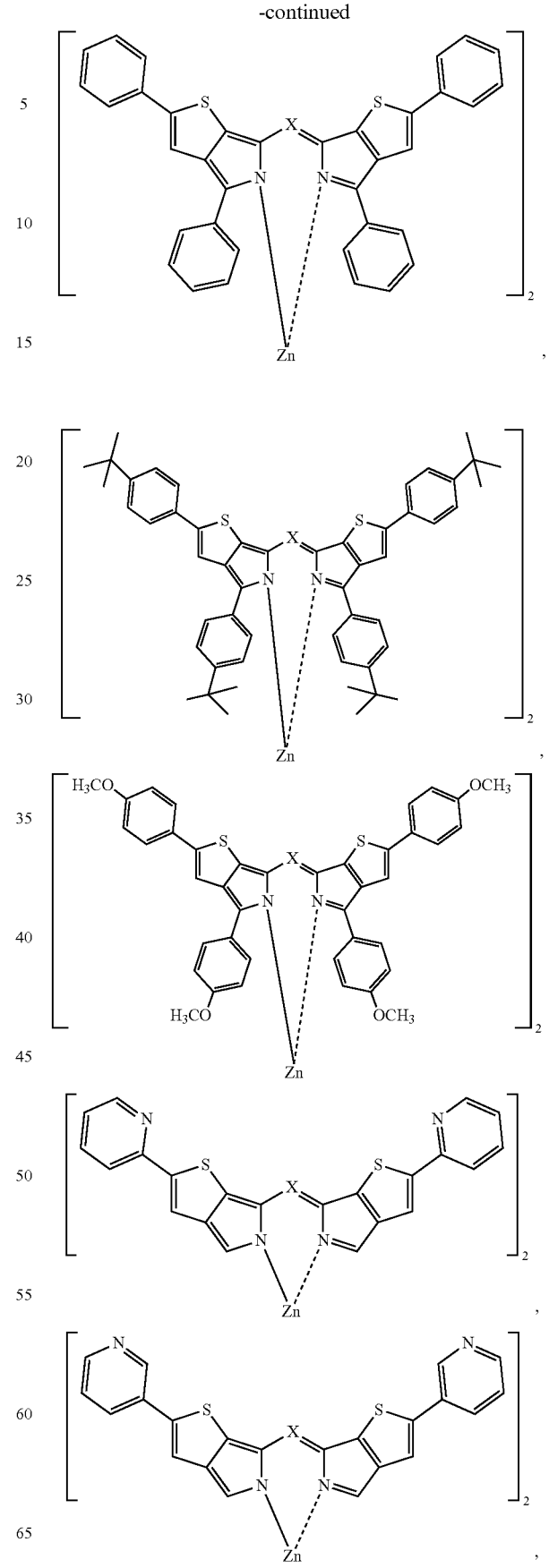

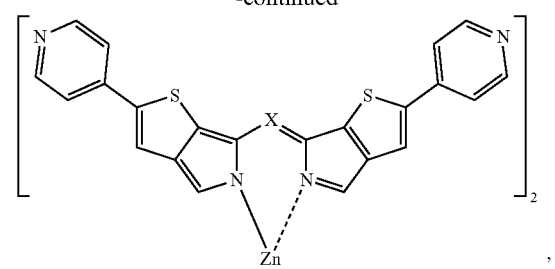
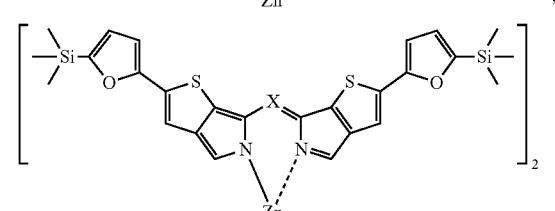
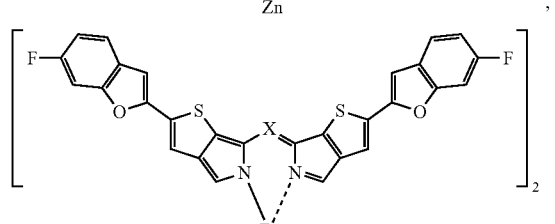
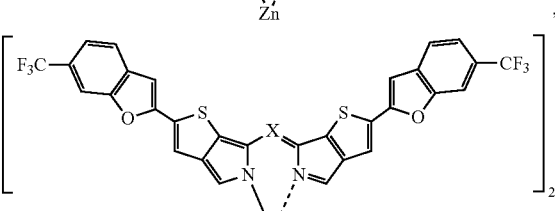
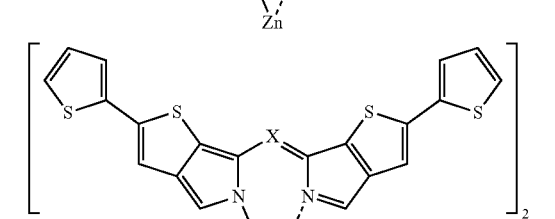
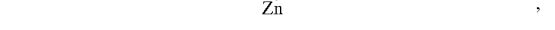
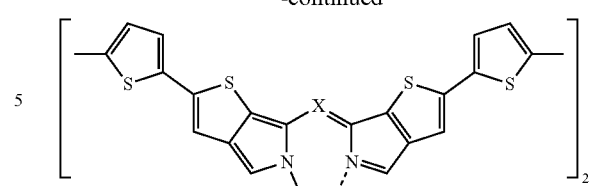
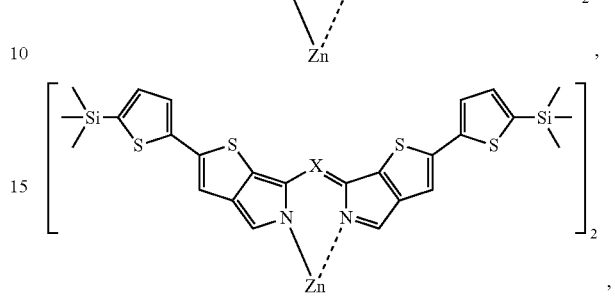
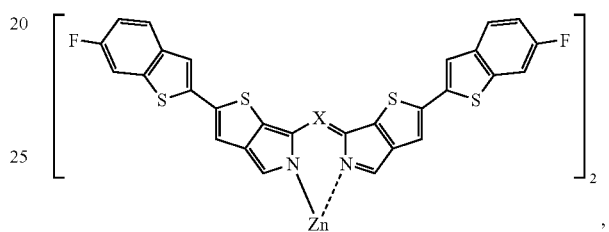
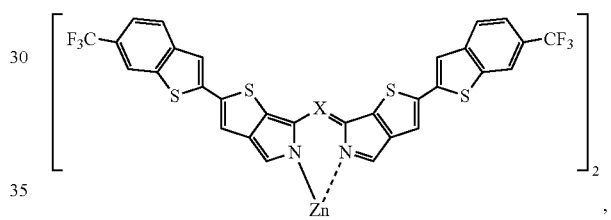
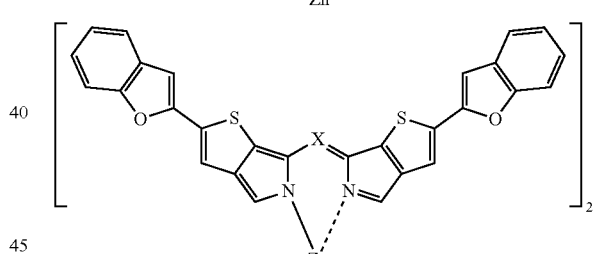
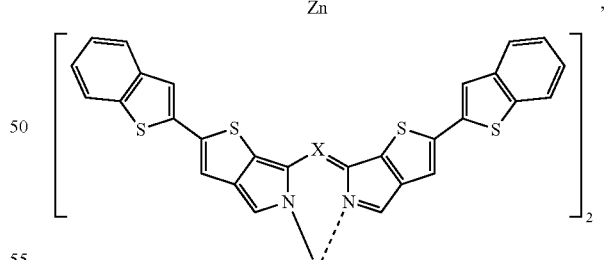
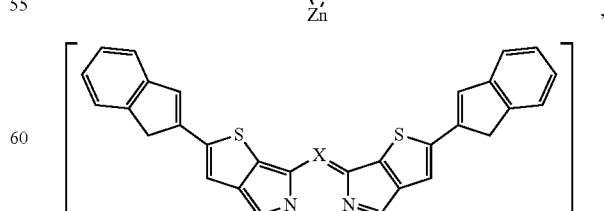
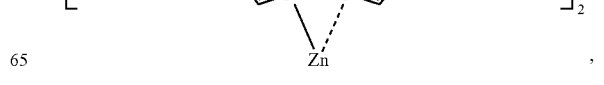

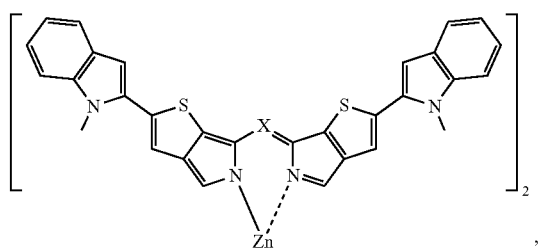,
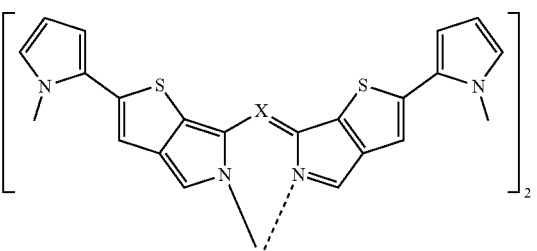,
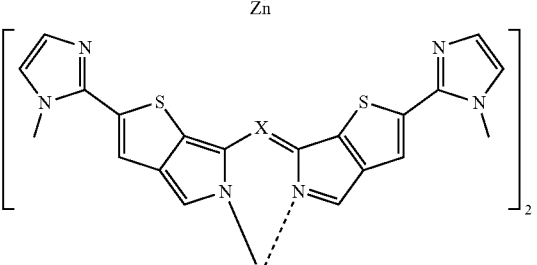,
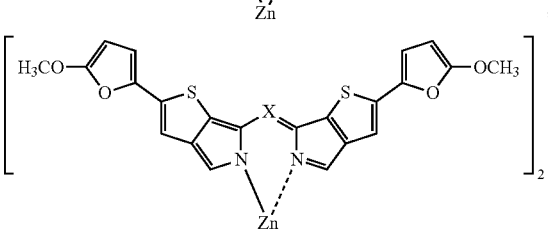,
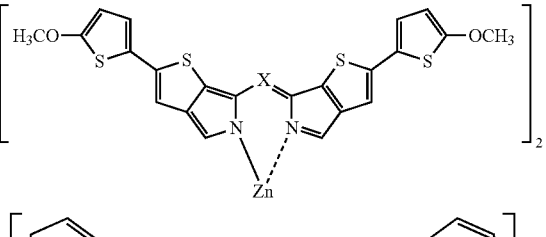,
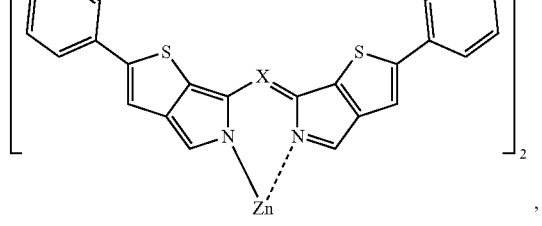,
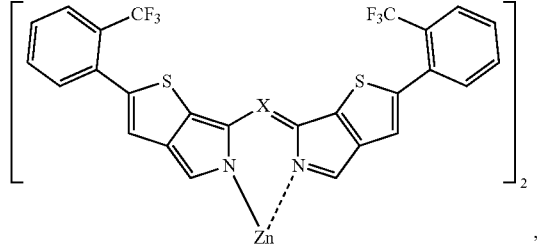,
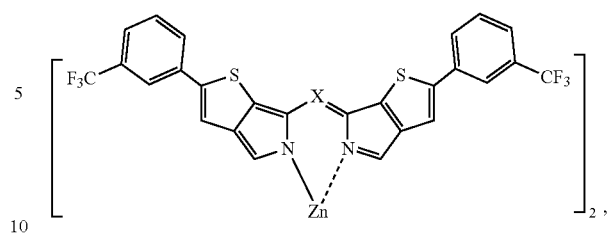,
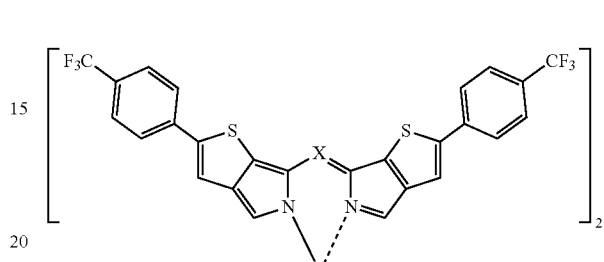,
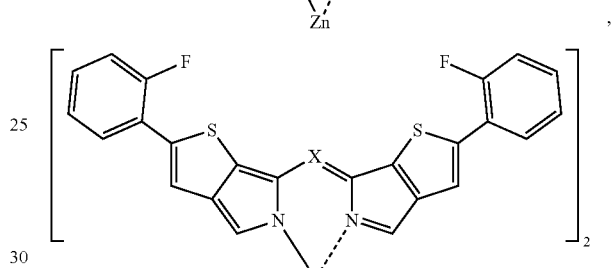,
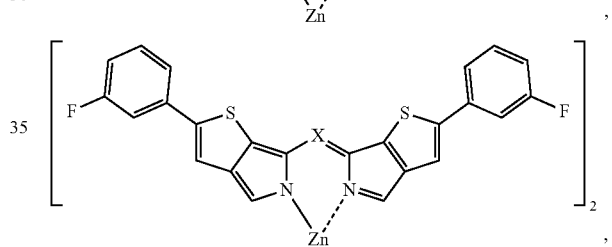,
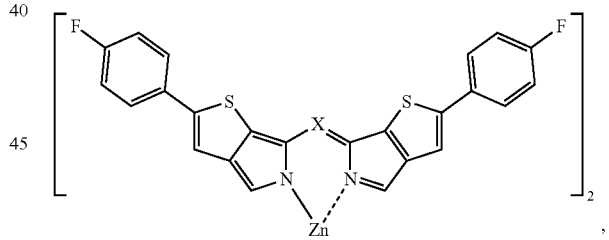,
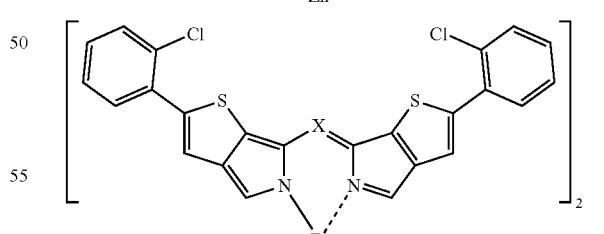,
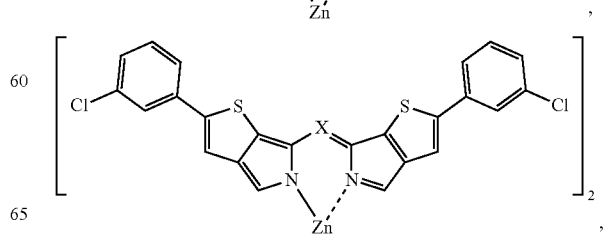,

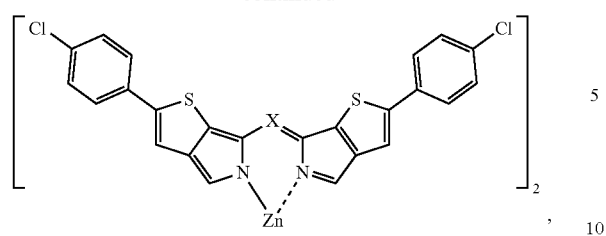
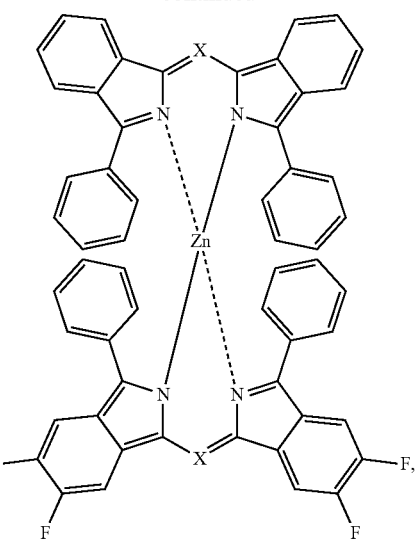
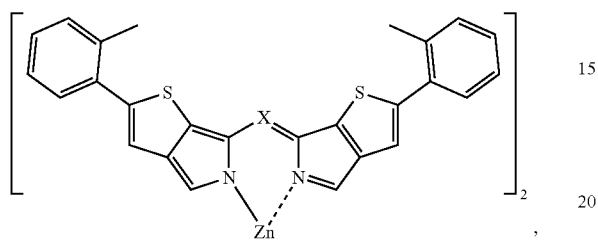
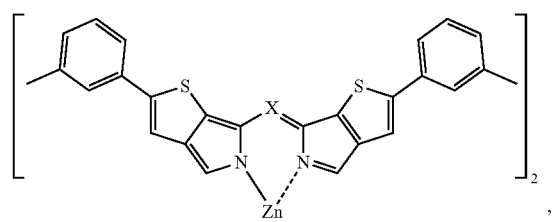
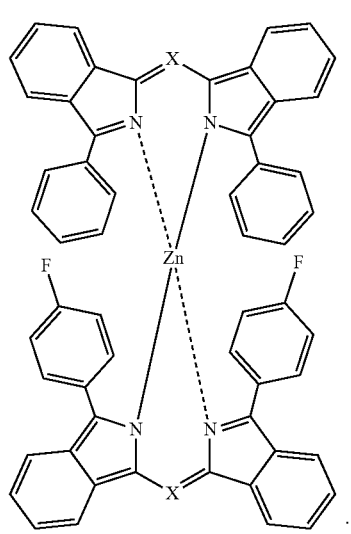
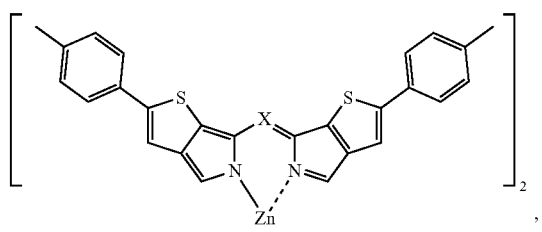
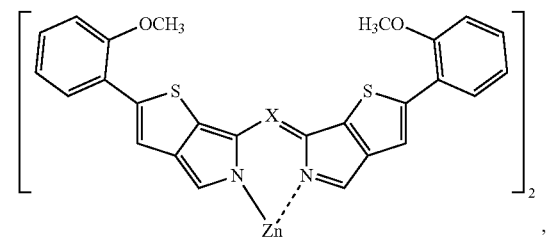
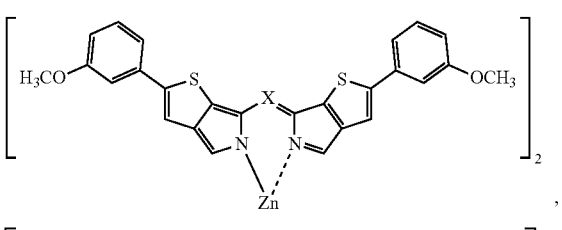
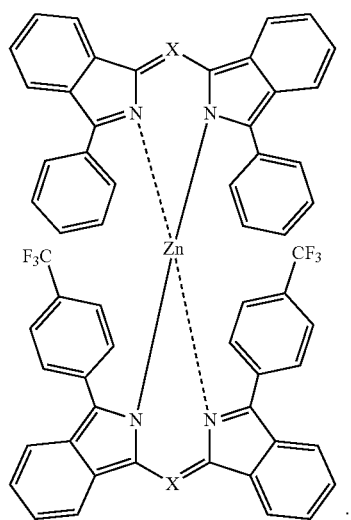
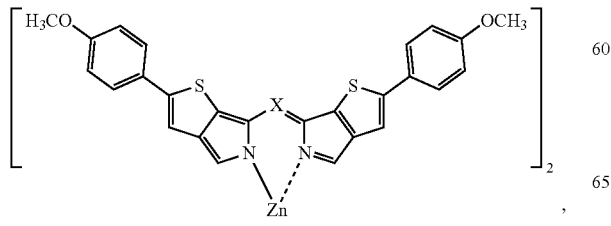

93
-continued
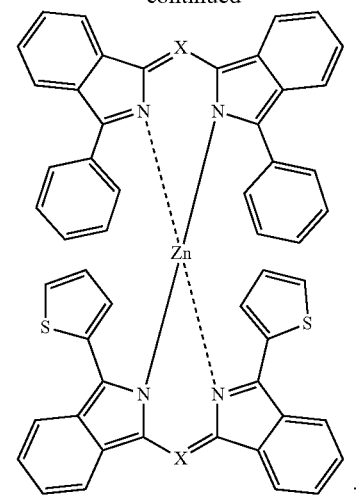
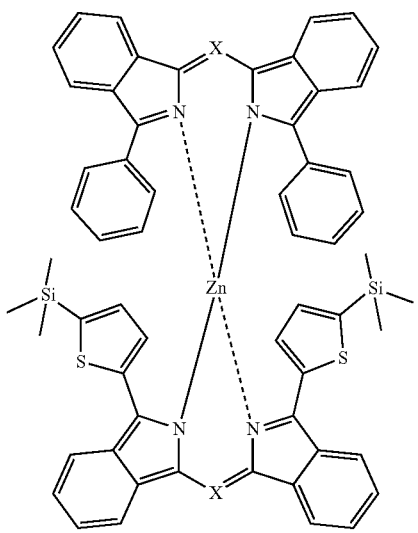
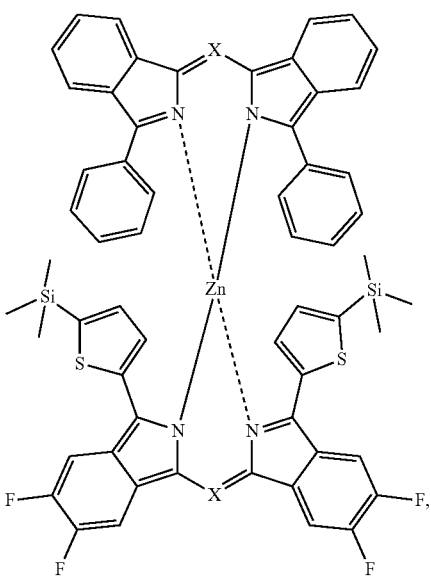
94
-continued
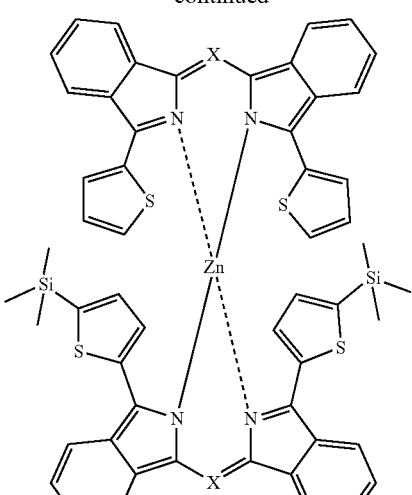
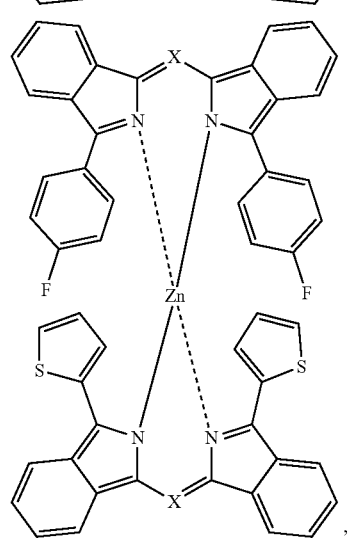
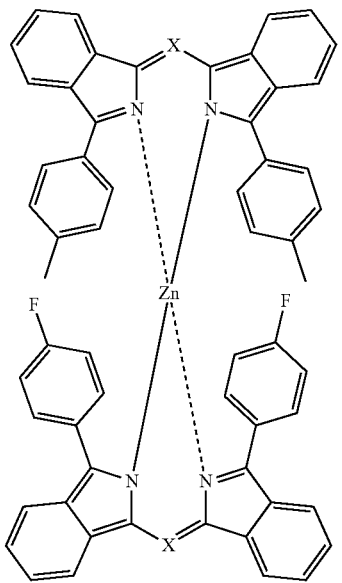

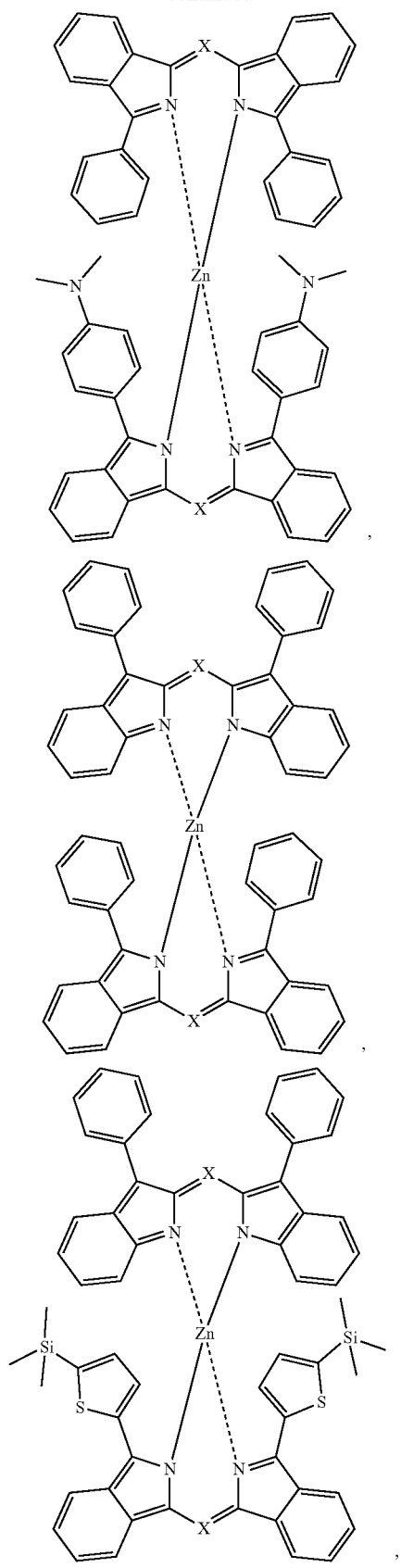
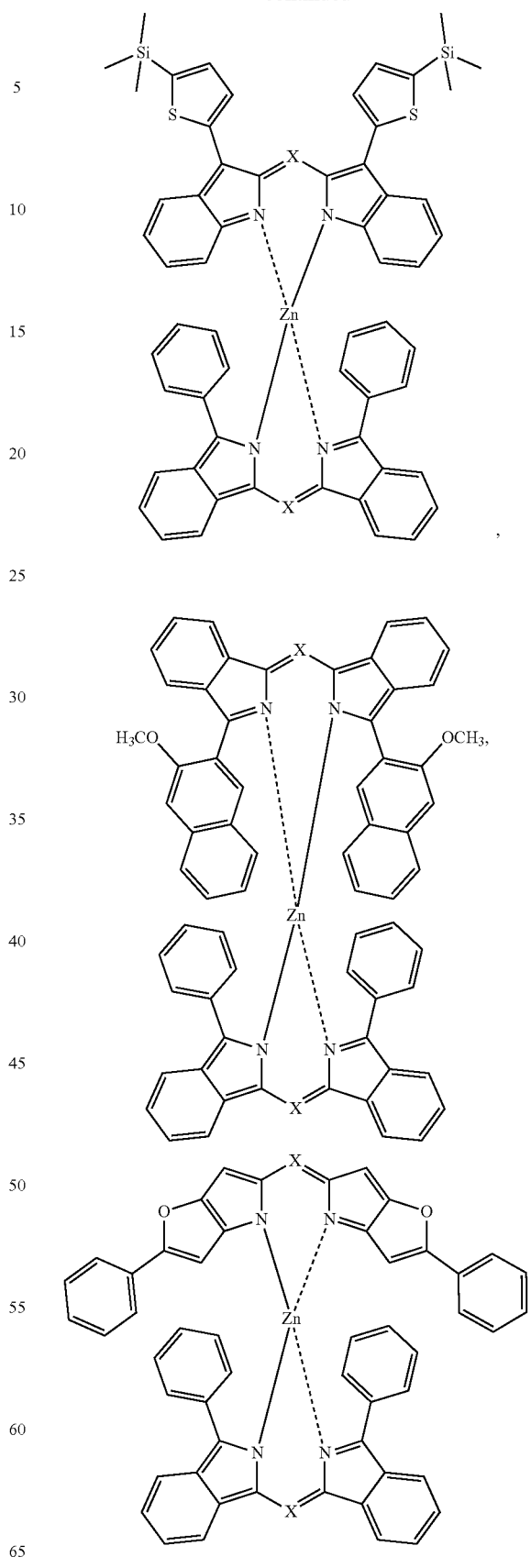

97
-continued
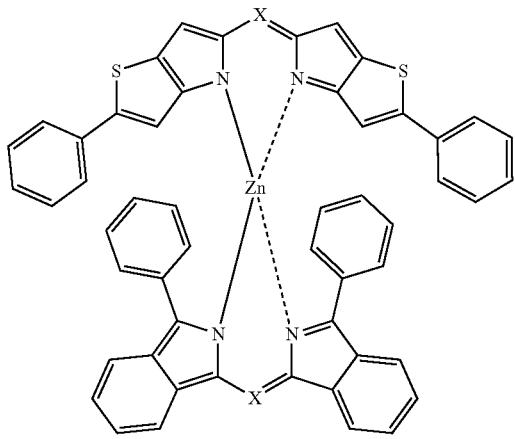
,
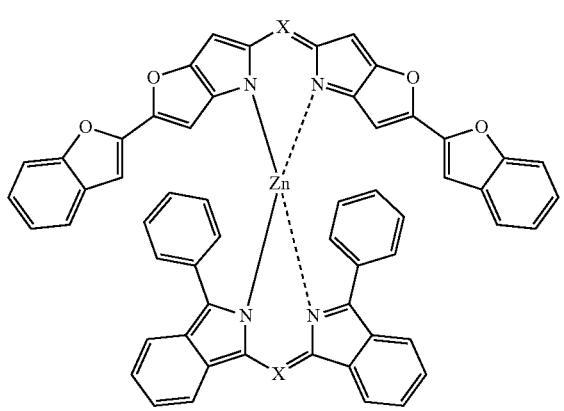
,
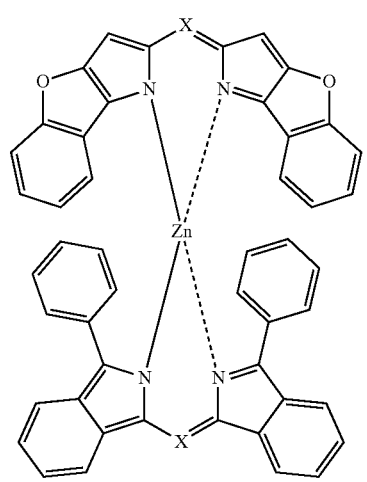
,
98
-continued
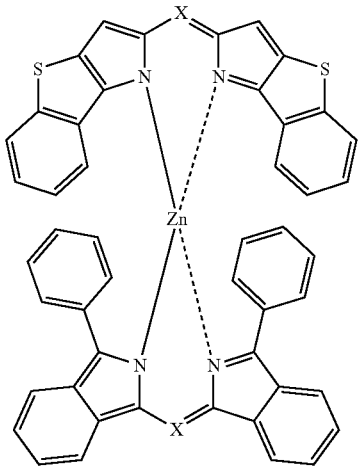
,
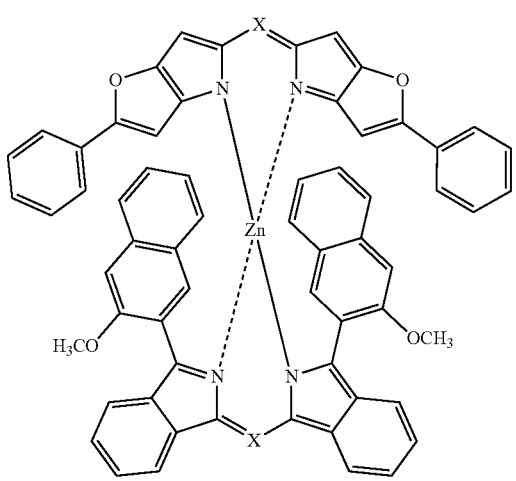
,
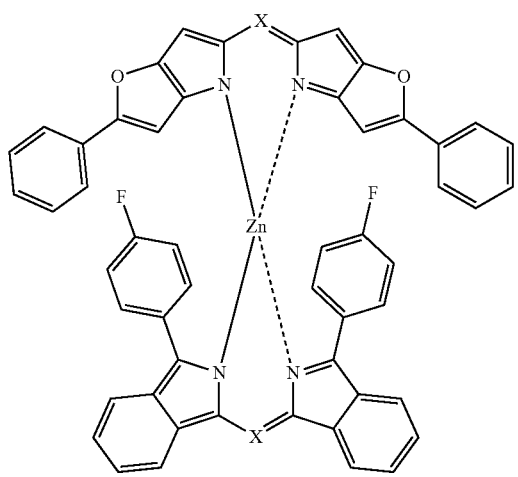
, 99
-continued
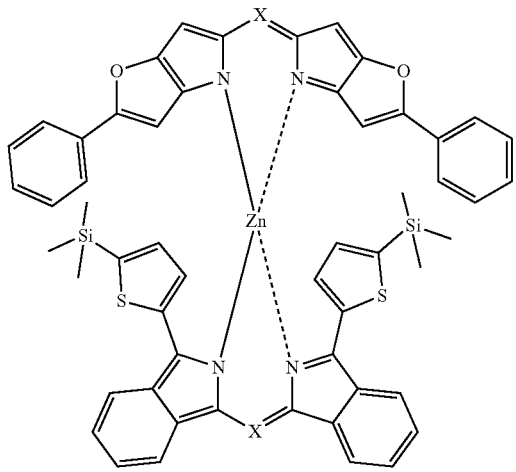
,
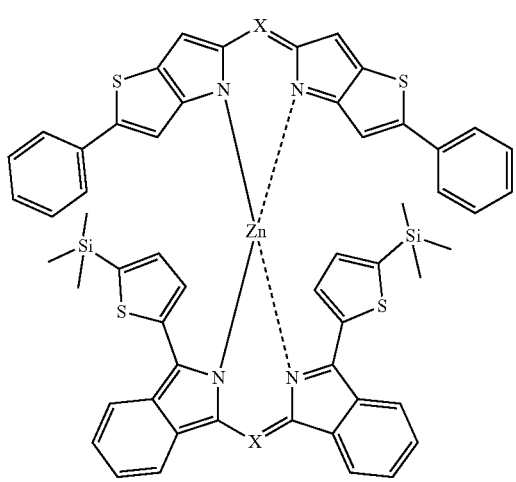
,
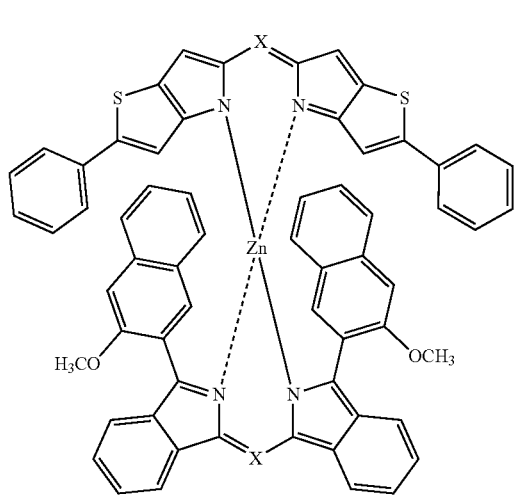
,
100
-continued
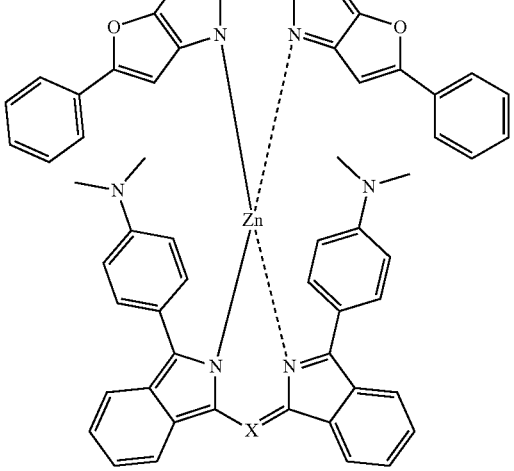
,
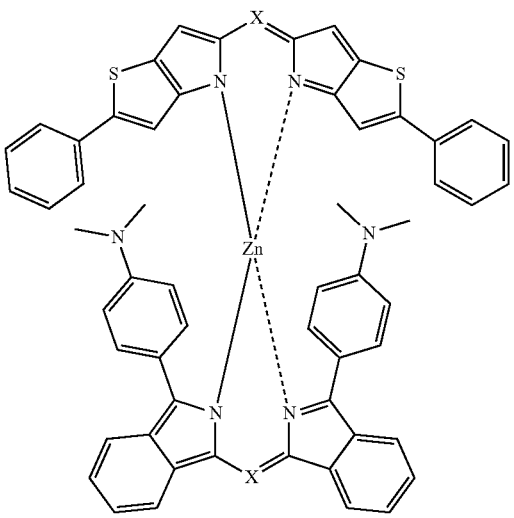
,
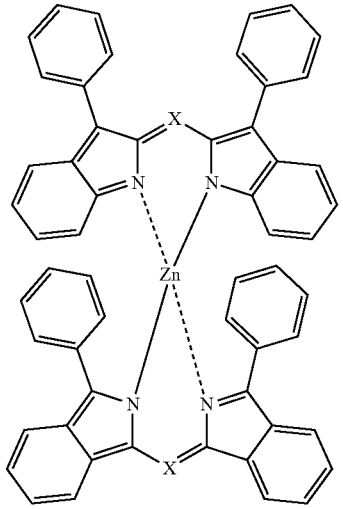
, 101
-continued
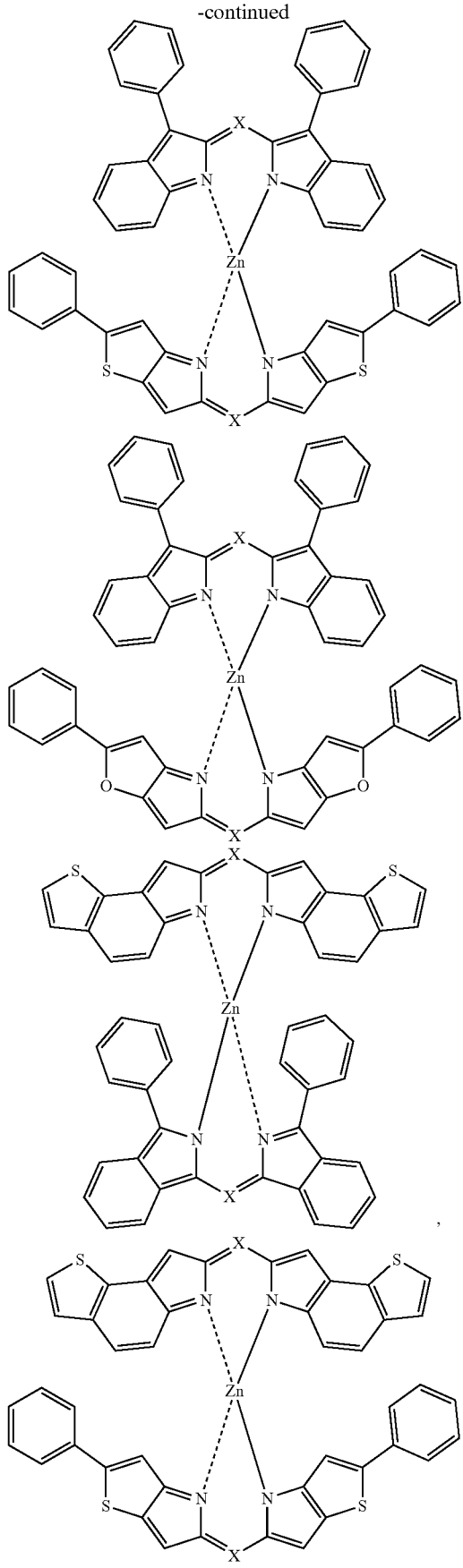
102
-continued
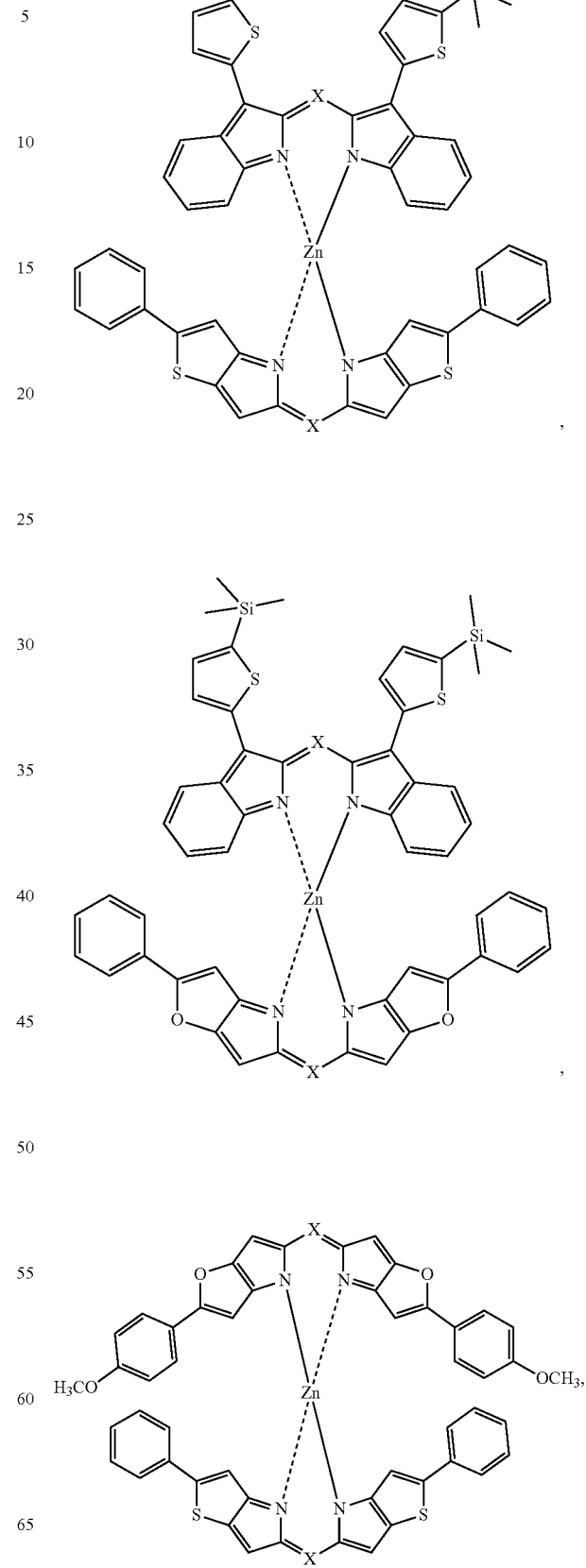

103
-continued
104
-continued
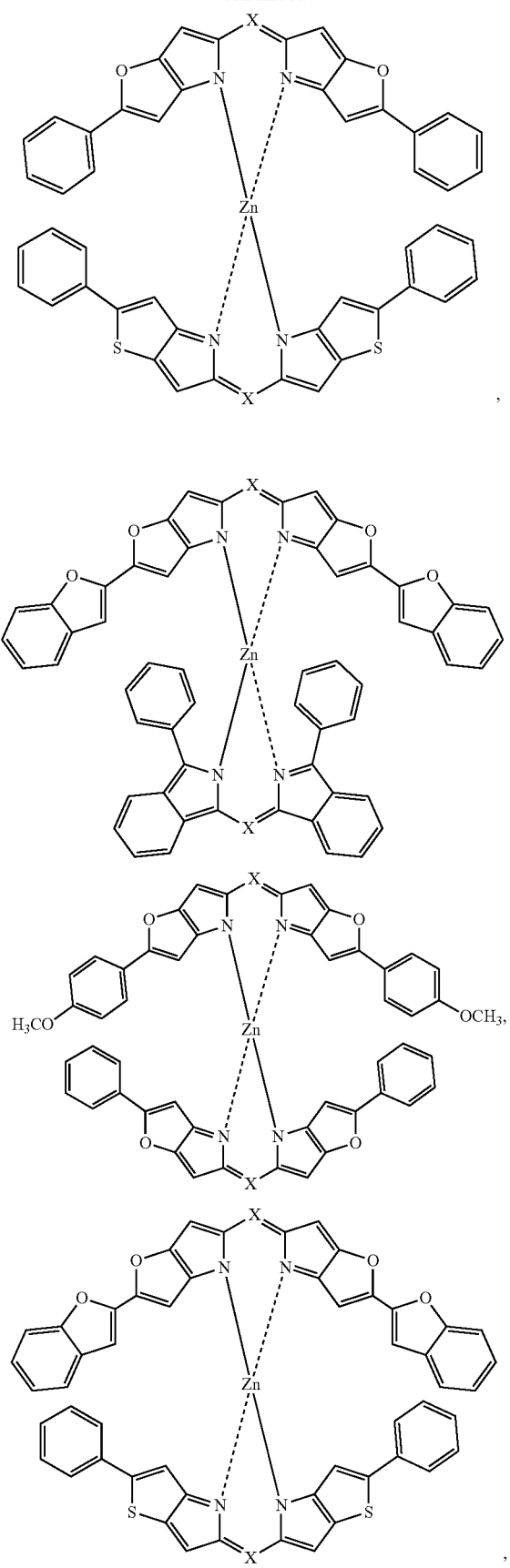
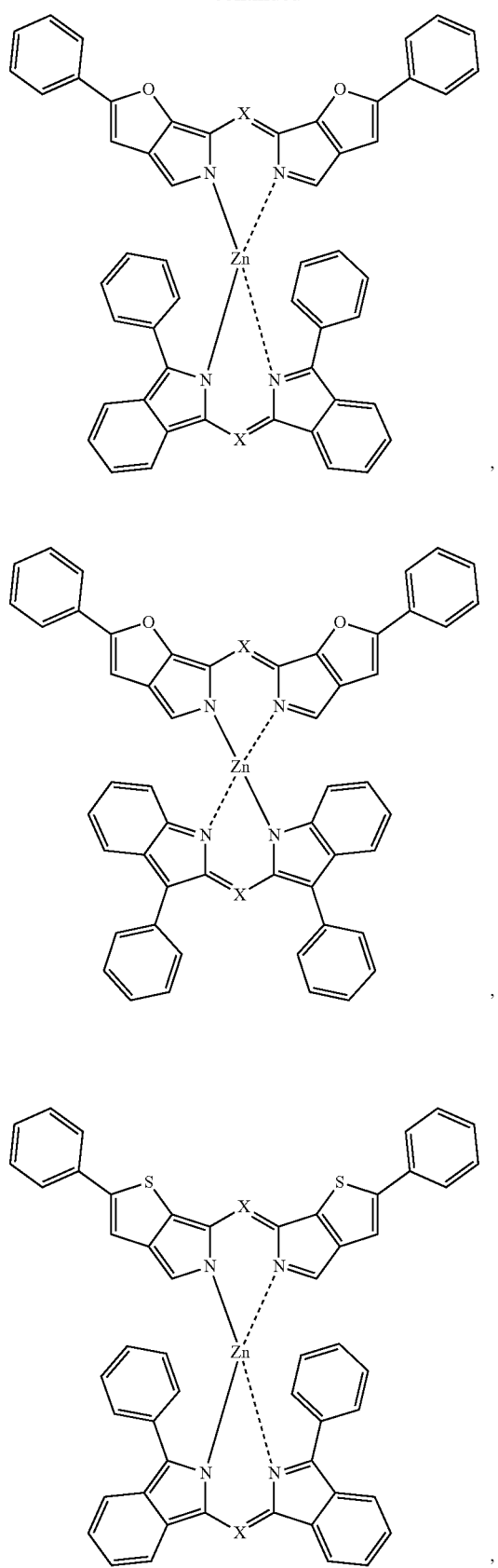

105
-continued
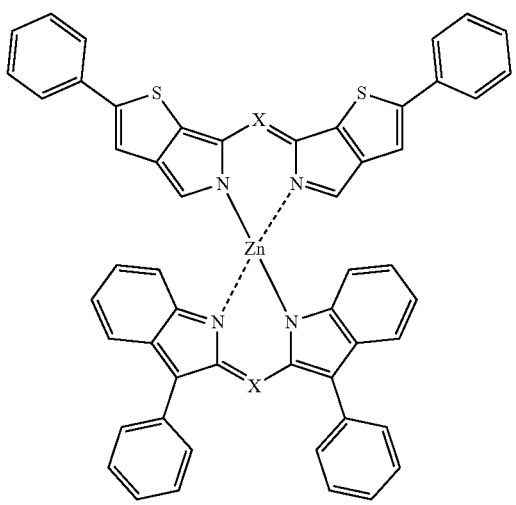
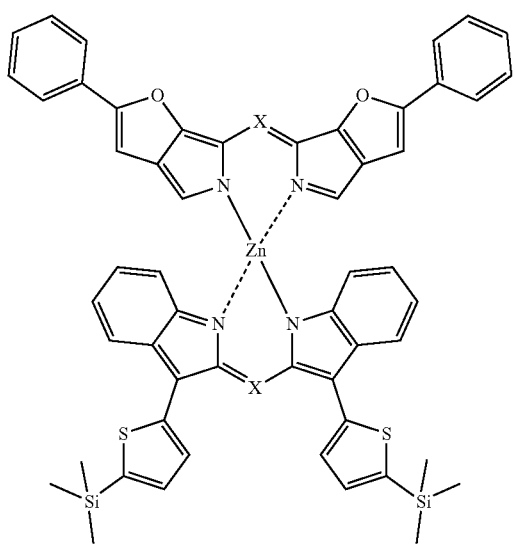
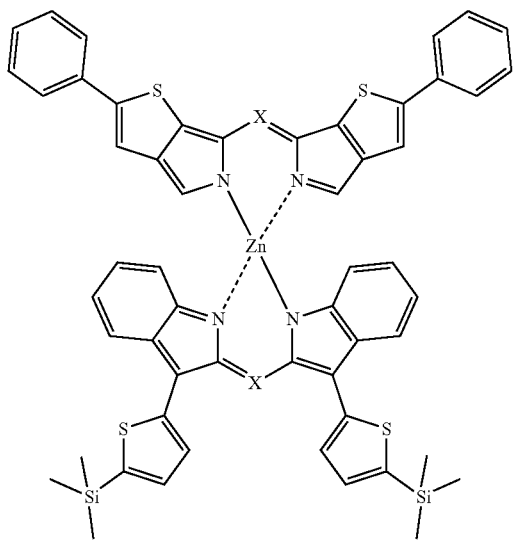
106
-continued
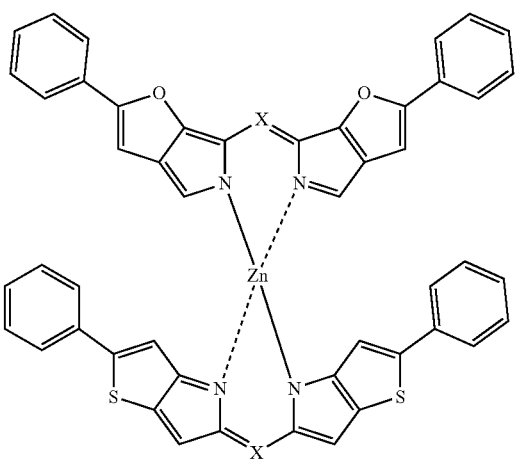
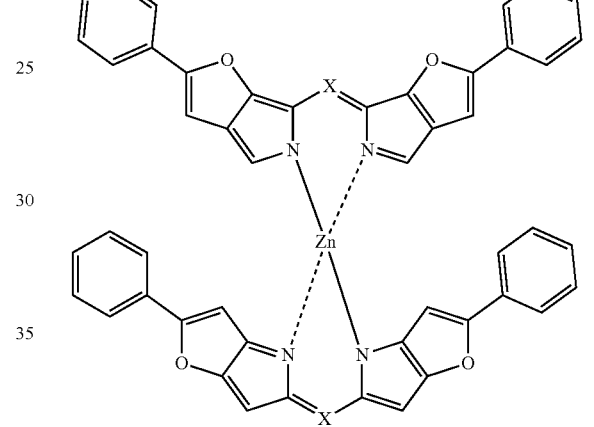
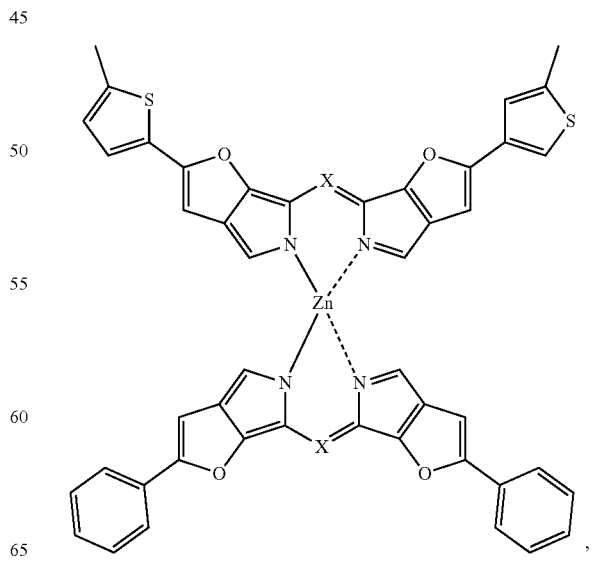

107
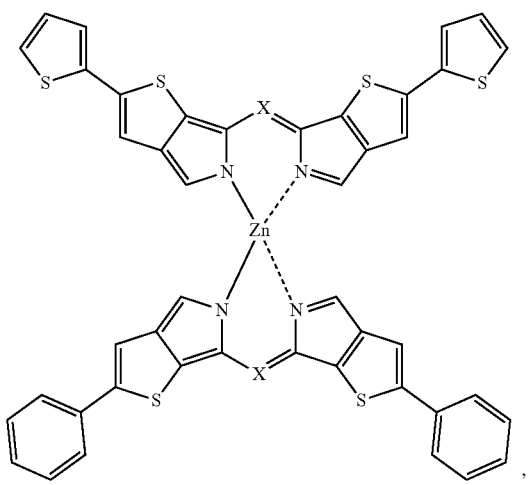
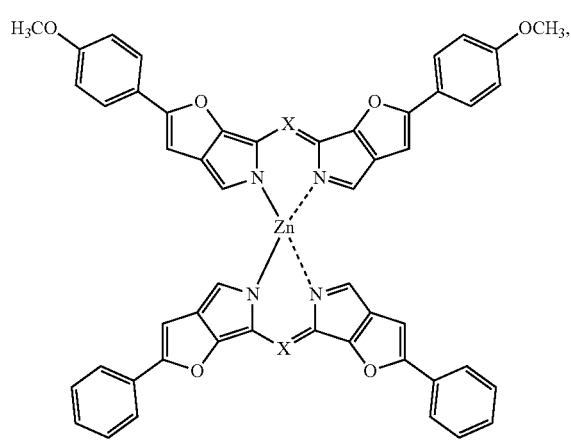
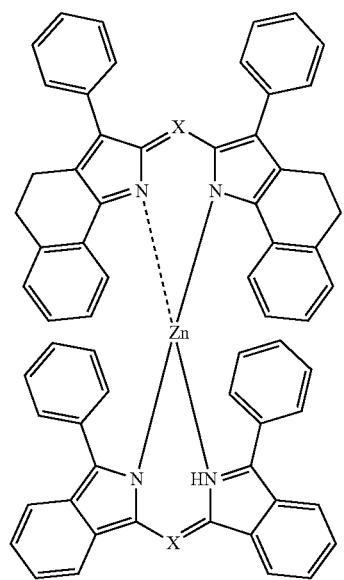
108
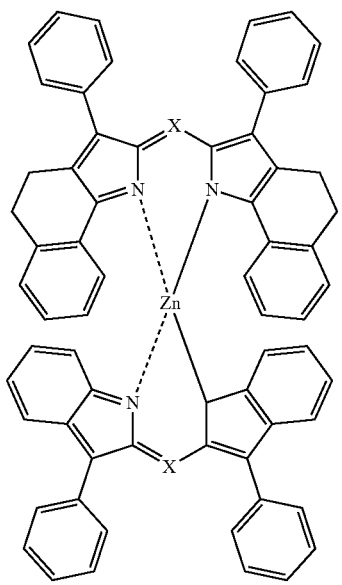
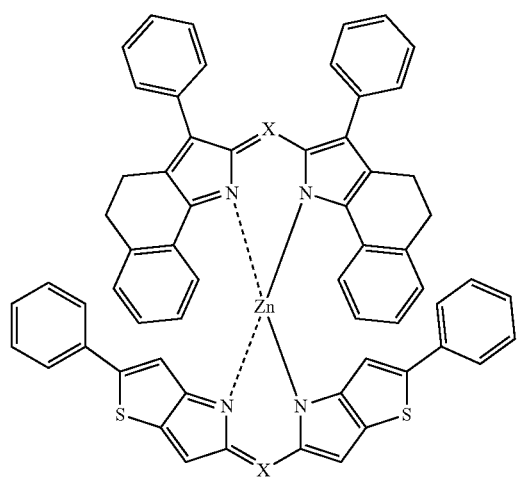
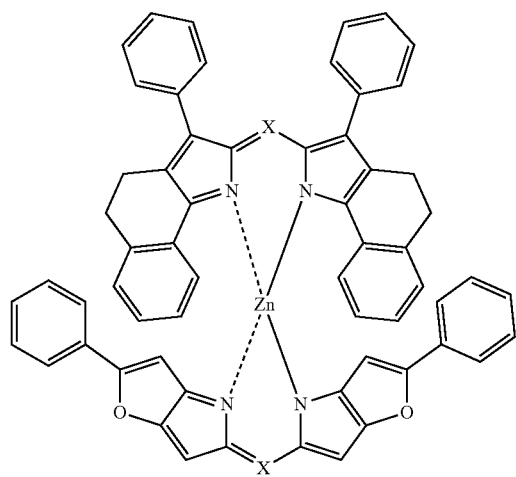

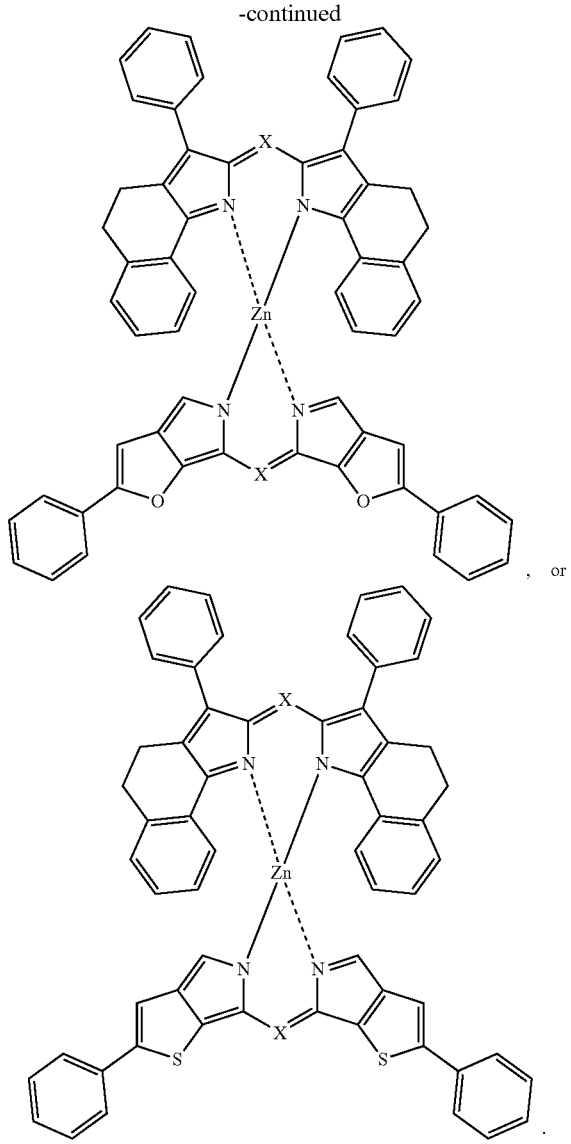

, or

.

In the above examples, X may optionally be N, X may optionally be CH, X may optionally be C—CF$_3$, or X may optionally be C—CN. It will be appreciated that a variety of other photoactive compounds are included beyond those specified above.

The disclosed photoactive compounds can be paired with a variety of other compounds to form a photovoltaic heterojunction. For example, when the photoactive compound is an electron acceptor compound, it can be paired with a counterpart electron donor material. As another example, when the photoactive compound is an electron donor compound, it can be paired with a counterpart electron acceptor material. A counterpart electron donor material may be a counterpart electron donor compound, for example, and may be different in some cases from the photoactive materials described herein. A counterpart electron acceptor material may be a counterpart electron donor compound, for example, and may be different in some cases from the photoactive materials described herein. In some cases, a photoactive layer may comprise one or multiple different electron donor compounds (i.e., blends of different photoactive compounds). In some cases, a photoactive layer may comprise one or multiple different electron acceptor compounds (i.e., blends of different photoactive compounds).

The photoactive compounds described herein can be paired with any of a variety of counterpart photoactive compounds. In some examples, the photoactive material of a device may contain a photoactive compound that is an electron acceptor compound described herein and the electron donor compound comprises a boron-dipyrromethene (BODIPY) compound, a phthalocyanine compound, a naphthalocyanine compound, a metal dithiolate (MDT) compound, a dithiophene squaraine compound, an indacenodithieno[3,2-b]thiophene (ITIC) compound, a core disrupted indacenodithieno[3,2-b]thiophene (ITIC) compound, or a S,N-heteropentacene compound. Combinations thereof may also be used. Examples of useful BODIPY compounds include, but are not limited to, those described in U.S. patent application Ser. No. 16/010,371, filed on Jun. 15, 2018, which is hereby incorporated by reference. Examples of useful phthalocyanine and naphthalocyanine compounds include, but are not limited to, those described in U.S. patent application Ser. No. 16/010,365, filed on Jun. 15, 2018, which is hereby incorporated by reference. Examples of useful MDT compounds include, but are not limited to, those described in U.S. patent application Ser. No. 16/010,369, filed on Jun. 15, 2018, which is hereby incorporated by reference. Examples of useful dithiophene squaraine compounds include, but are not limited to, those described in U.S. patent application Ser. No. 16/010,374, filed on Jun. 15, 2018, which is hereby incorporated by reference. Examples of useful core disrupted and/or planar ITIC compounds containing indandione groups include, but are not limited to, those described in PCT Application No. PCT/US2021/058125, filed on Nov. 4, 2021, which is hereby incorporated by reference. Examples of useful heteropentacene/heteroaromatic compounds include, but are not limited to, those described in U.S. Provisional Application No. 63/140,758, filed on Jan. 22, 2021, U.S. Provisional Application No. 63/141,390, filed on Jan. 25, 2021, U.S. Provisional Application No. 63/275,311, filed on Nov. 3, 2021, and U.S. patent application Ser. Nos. 17/519,360, 17/519,361, and 17/519,364, filed on Nov. 4, 2021, which are hereby incorporated by reference. Additional useful heteropentacene/heteroaromatic compounds include, but are not limited to, those described in a U.S. Patent application entitled "HETEROAROMATIC PHOTOACTIVE COMPOUNDS FOR TRANSPARENT PHOTOVOLTAIC DEVICES," filed on the same date as the instant application and having U.S. patent application Ser. No. 17/581,763, which is hereby incorporated by reference. In some examples, a photoactive layer contains a BODIPY compound, a phthalocyanine compound, a naphthalocyanine compound, a MDT compound, a dithiophene squaraine compound, an ITIC compound, a core-disrupted ITIC compound, a heteropentacene or heteroaromatic compound, or a combination thereof.

Aspects of the invention may be further understood by reference to the following non-limiting examples.

Example 1—Synthesis Examples of Metal Coordinated Photoactive Compounds

FIGS. 8-14 provide an overview of various example synthetic schemes providing synthetic routes for various photoactive metal coordinated compounds.

Figure 8:
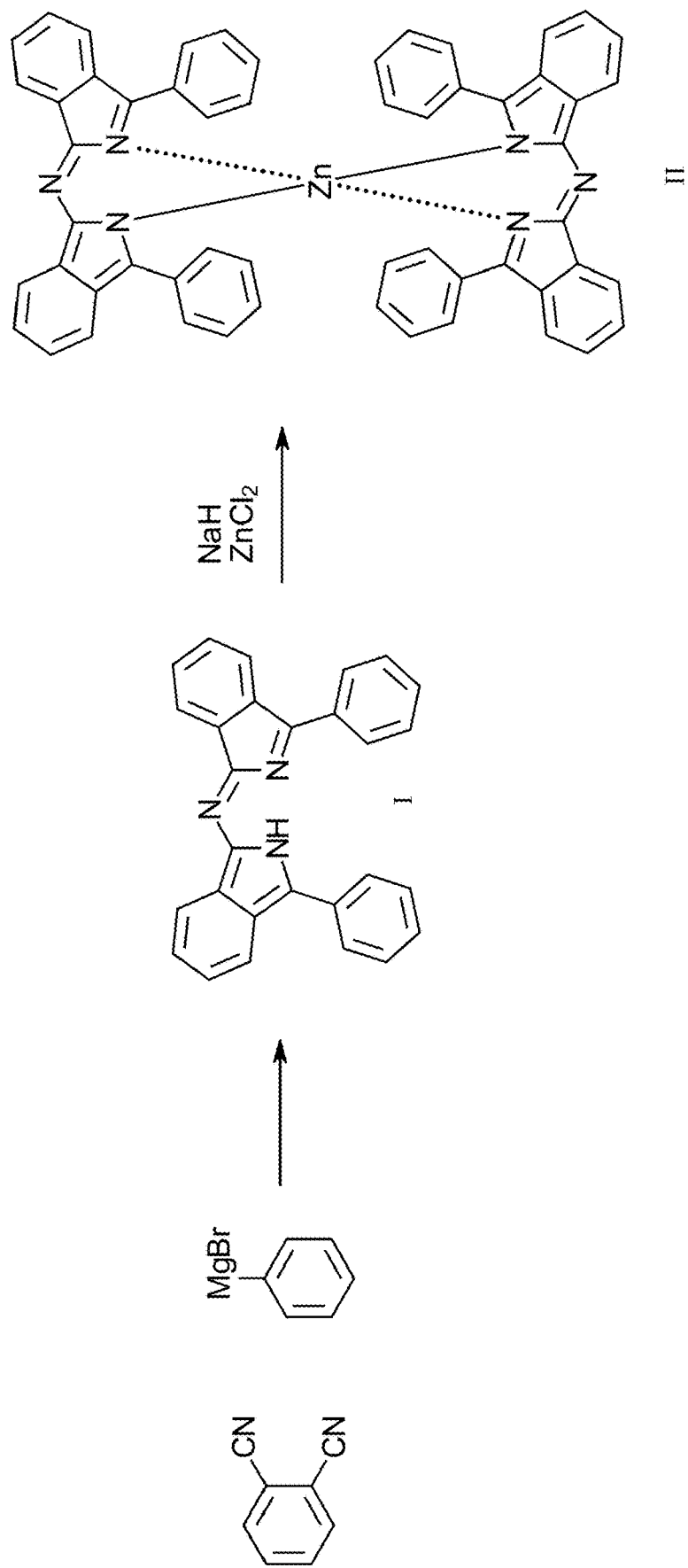
FIG. 8 provides a synthetic scheme for preparation of a first example metal coordinated compound.

FIG. 8 provides a synthetic scheme for preparation of an example metal coordinated compound:

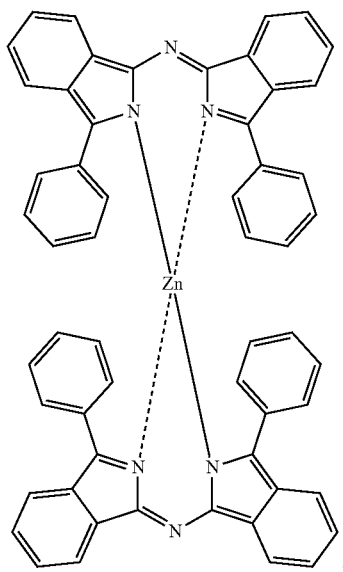

II

Compound I: An oven dried 3-neck 2 L round bottom flask, equipped with temperature probe, addition funnel and Schlenk line, 50 g of phthalonitrile (50 g, 0.39 mol) and dry toluene (~1.2 L) were added and purged with nitrogen. Addition funnel was charged with phenyl magnesium bromide (324 ml of 3 M solution in diethyl ether, 0.98 mmol) using cannula and it was added to the reaction mixture dropwise over 45 minutes. The reaction mixture was continued to stir for additional 2.5 h and then quenched by slowly adding 20% aqueous ammonium chloride (250 ml) keeping reaction temperature under 50° C. using ice bath. Additional 100 ml of water was added, and the mixture was steam distilled on heating mantle (temperature 110-115° C.). After 5 h additional 1 L water was added and mixture was continued to steam distill overnight. The mixture was again steam distilled with additional 1 L water over 3 hrs. The product, a blue colored hard solid chunk, was filtered using hot water and grinded using mortar/pestle. The solid was transferred into a one neck round bottom and stirred with 1 L MeOH/water (2/1) at 60° C. on water bath for 30 mins and filtered. The solid was suspended in IPA (1 L), stirred for 30 min and filtered. The solid obtained still has some baseline impurity and was again suspended in IPA (1 L) and stirred for 24 hrs and filtered. Brown colored solid was dried under high vacuum at 45° C. overnight to obtain compound I (50.16 g, 64.6%).

Figure 15A:
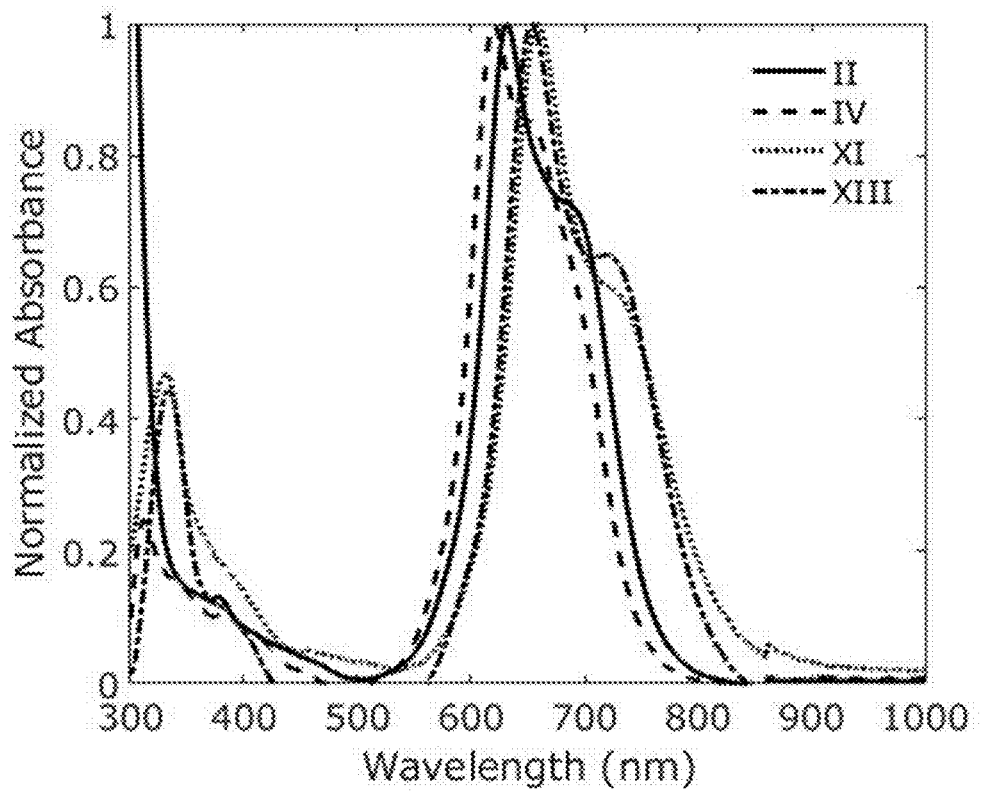
FIG. 15A and FIG. 15B provides solution absorption spectra of example metal coordinated compounds in dichloromethane solvent.
Figure 16:
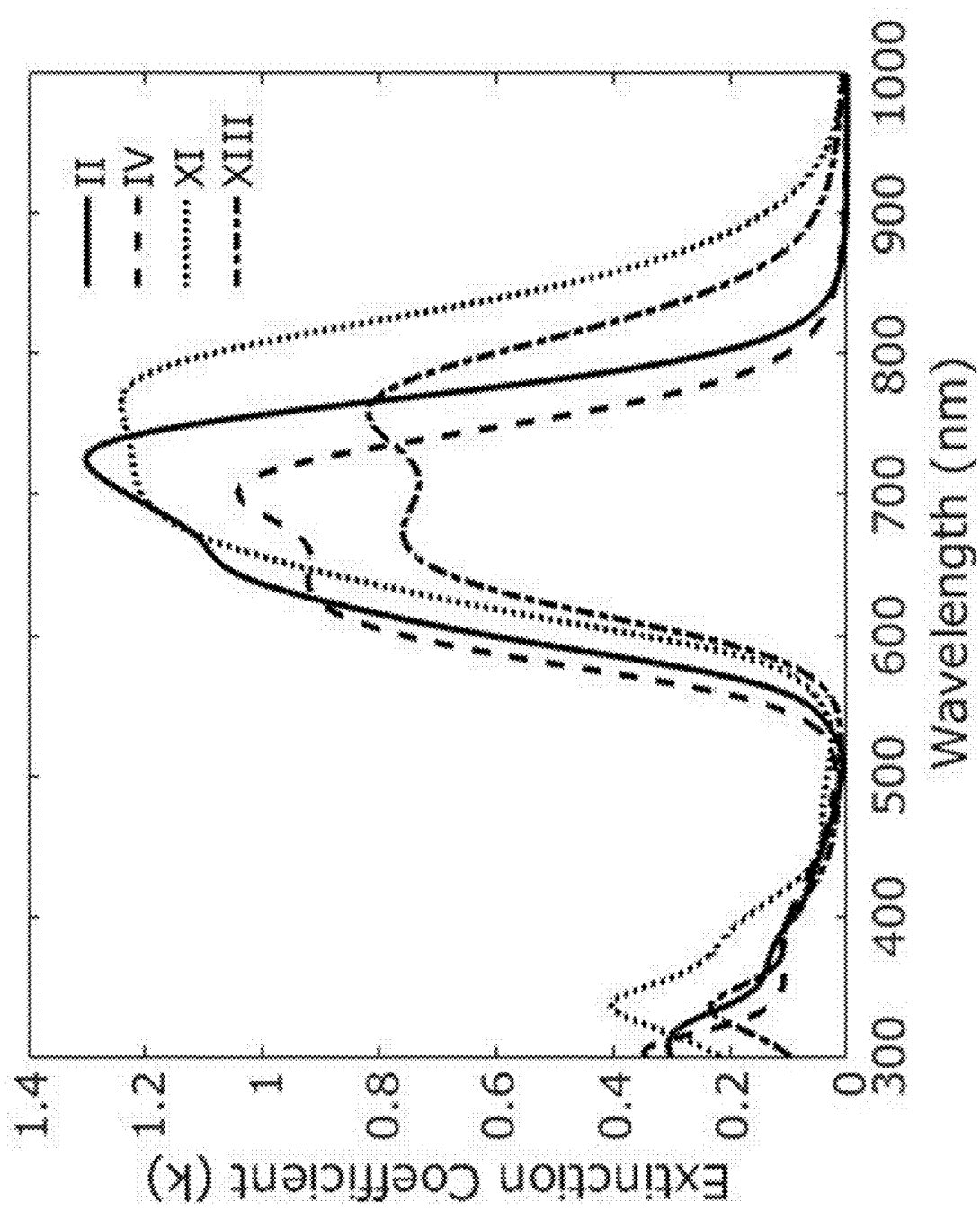
FIG. 16 provides solid phase film absorption spectra of example metal coordinated compounds.

Compound II: To a dry 500 ml three-neck flask equipped with a thermocouple and condenser compound I (1.5 g, 1.65 mmol) was added followed by addition of sodium hydride (30 mg, 2.1 mmol) and anhydrous THF (20 ml) under nitrogen atmosphere. The reaction mixture was stirred at 55° C. for 4 hours. The reaction mixture was then cooled to room temperature followed by addition of anhydrous dichloromethane (100 ml) and zinc chloride (0.136 g, 1 mmol) dissolved in methanol (4 ml), added dropwise over 15 minutes. The reaction was stirred at room temperature for 12 h. Solution is filtered at room temperature to remove undissolved salts and then concentrated under vacuum. The crude product was washed with methanol and acetone to yield compound II (1.3 g, 86% yield). Compound II was sublimed in 50% yield. Solution (dichloromethane) and film absorption spectra of compound II is provided in FIG. 15A and FIG. 16, respectively.

Figure 9:
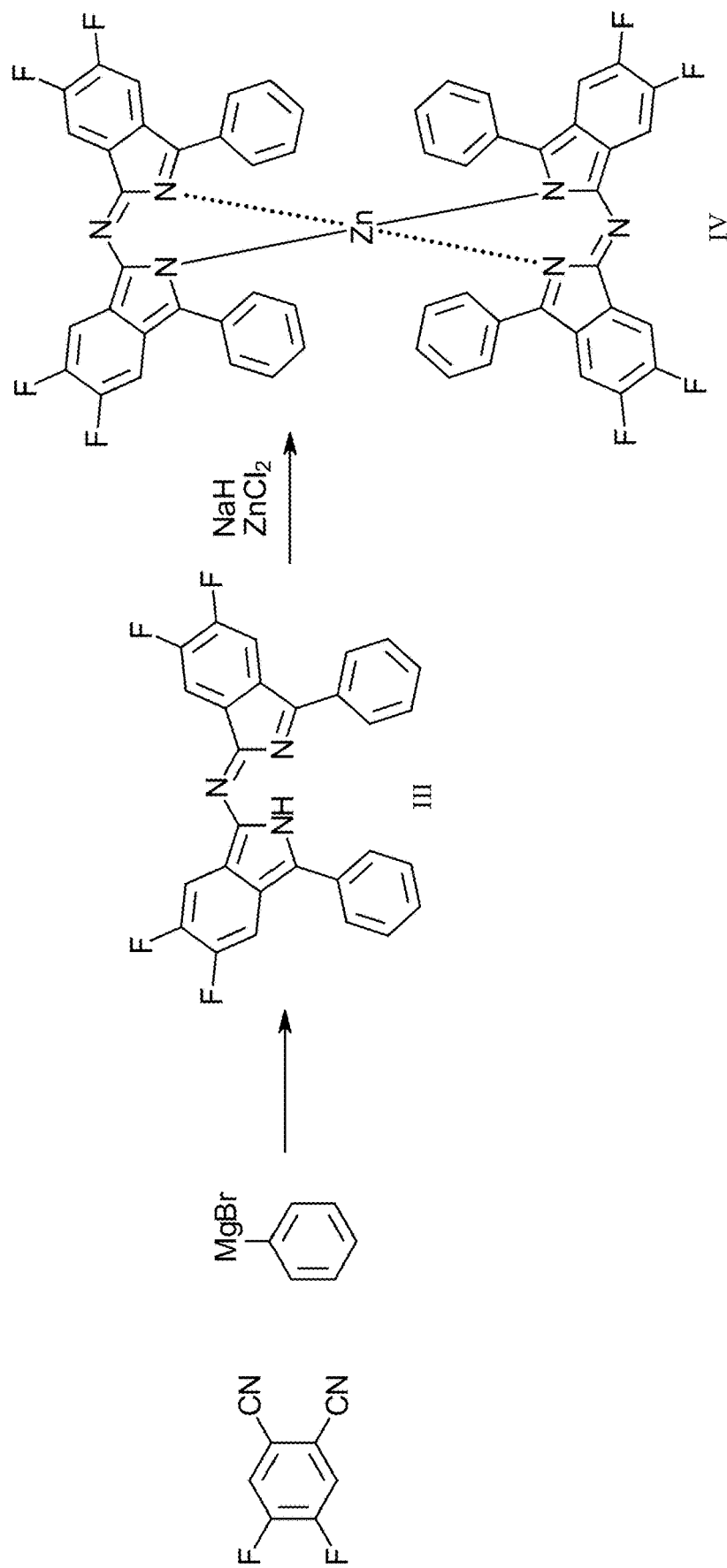
FIG. 9 provides a synthetic scheme for preparation of a second example metal coordinated compound.

FIG. 9 provides a synthetic scheme for preparation of an example metal coordinated compound:

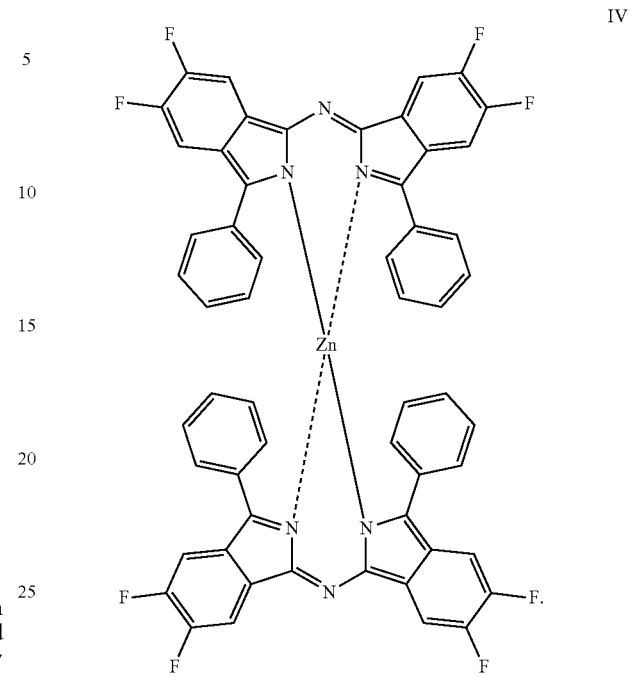

IV

Compound III was synthesized using the same method as described for preparing compound I, substituting 4,5-difluorophthalonitrile in place of phthalonitrile. Compound III was obtained in 33% yield.

Compound IV was synthesized using the same method as described for preparing compound II, substituting compound III in place of compound I. Compound IV was sublimed in 69% yield. Solution (dichloromethane) and film absorption spectra of compound IV is provided in FIG. 15A and FIG. 16, respectively.

Figure 10:
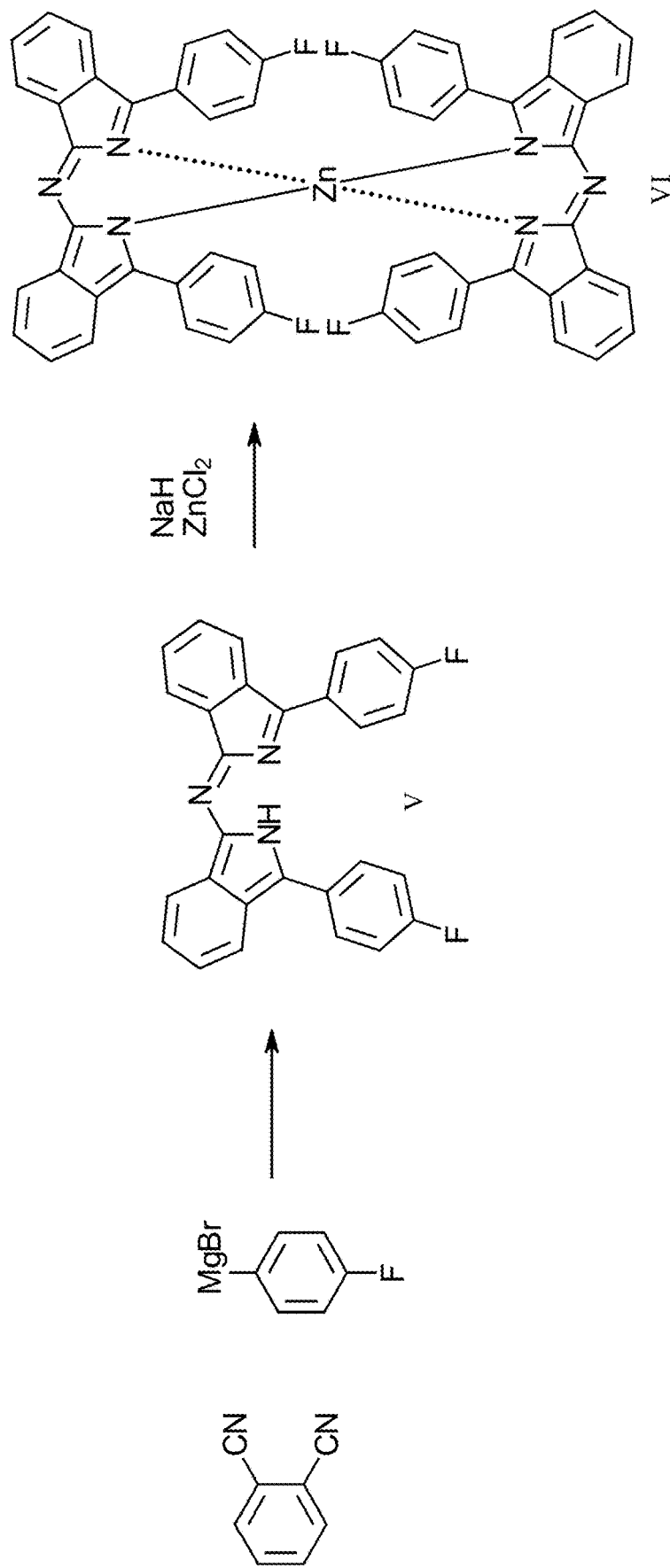
FIG. 10 provides a synthetic scheme for preparation of a third example metal coordinated compound.

FIG. 10 provides a synthetic scheme for preparation of an example metal coordinated compound:

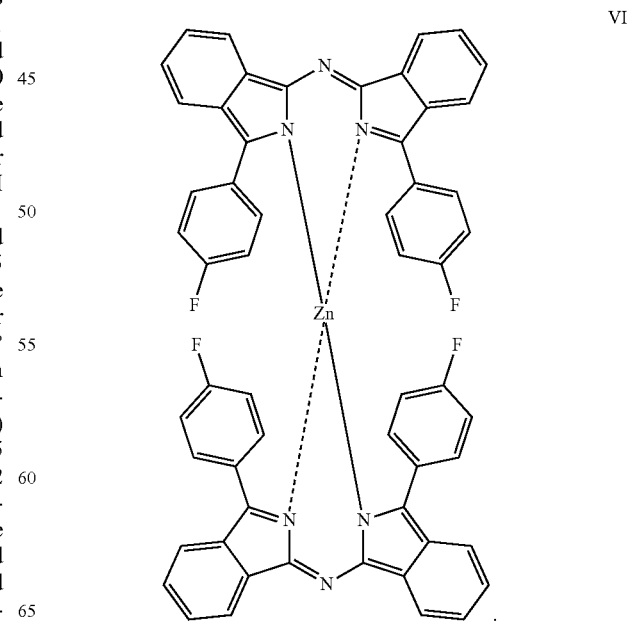

VI

Compound V was synthesized using the same method as described for preparing compound I, substituting 4-fluorophenyl magnesium bromide in place of phenyl magnesium bromide. Compound V was obtained in 56% yield.

Figure 15B:
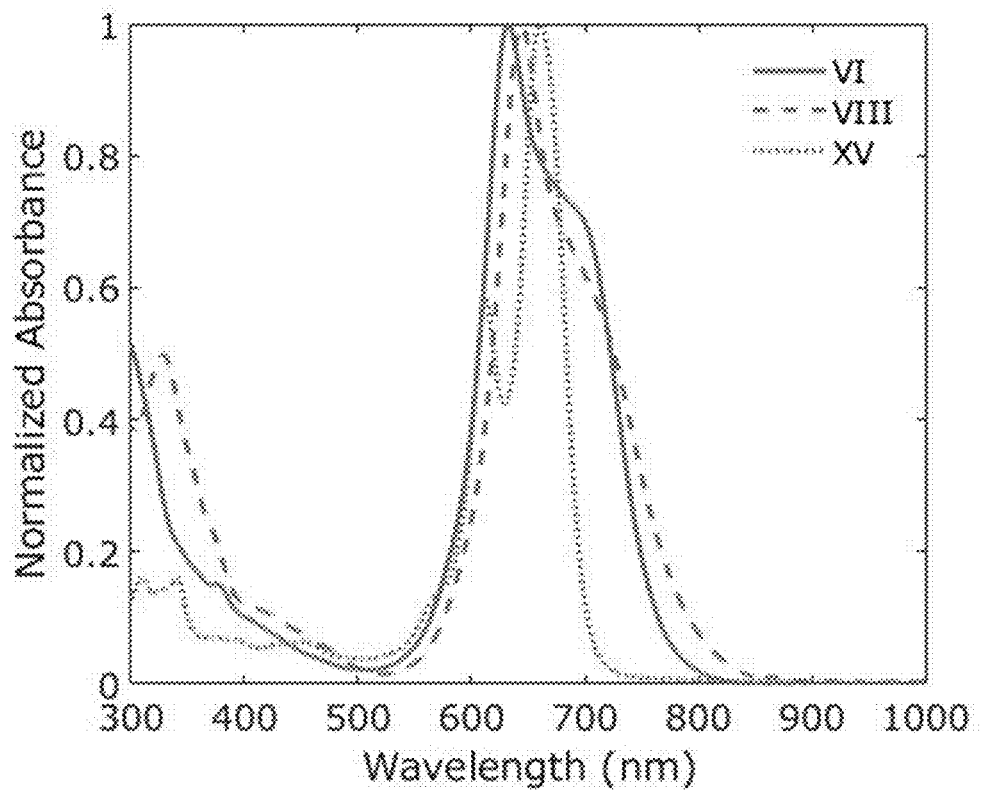

Compound VI was synthesized using the same method as described for preparing compound II, substituting compound V in place of compound I. Compound VI was obtained in 78% yield. A solution (dichloromethane) absorption spectrum of compound VI is provided in FIG. 15B.

Figure 11:
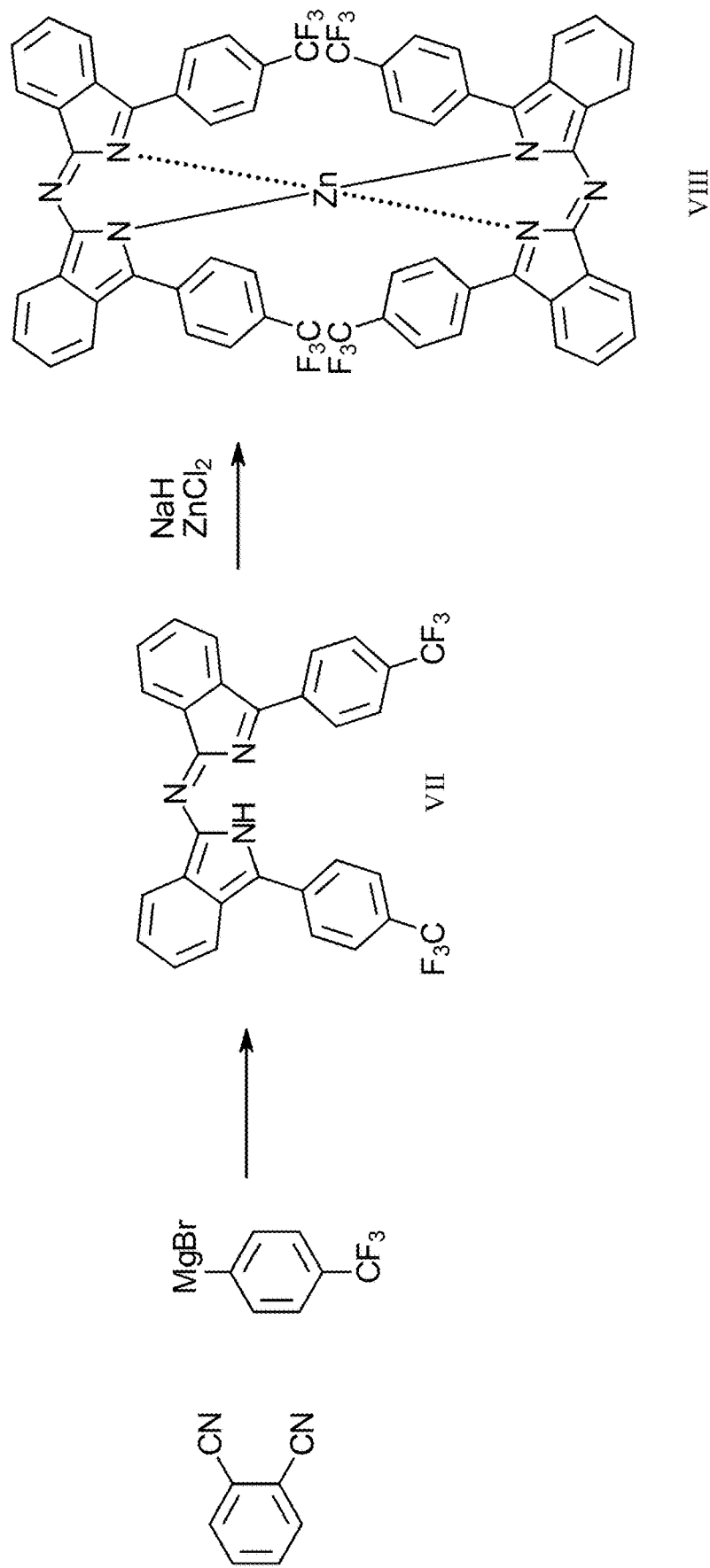
FIG. 11 provides a synthetic scheme for preparation of a fourth example metal coordinated compound.

FIG. 11 provides a synthetic scheme for preparation of an example metal coordinated compound:

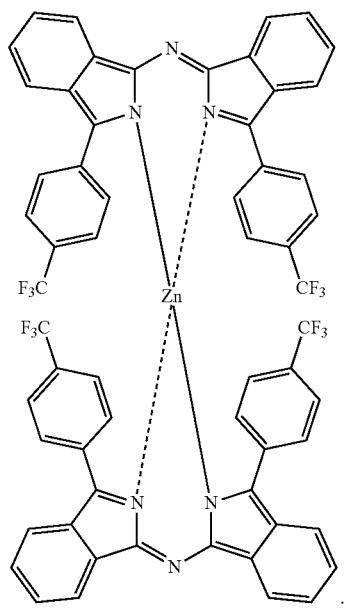

VIII

Compound VII was synthesized using the same method as described for preparing compound I, substituting 4-trifluoromethyl phenyl magnesium bromide in place of phenyl magnesium bromide.

Compound VIII was synthesized using the same method as described for preparing compound II, substituting compound VII in place of compound I. Compound VII was obtained in 63% yield. Compound VIII was sublimed in 14% yield. A solution (dichloromethane) absorption spectrum of compound VIII is provided in FIG. 15B.

Figure 12:
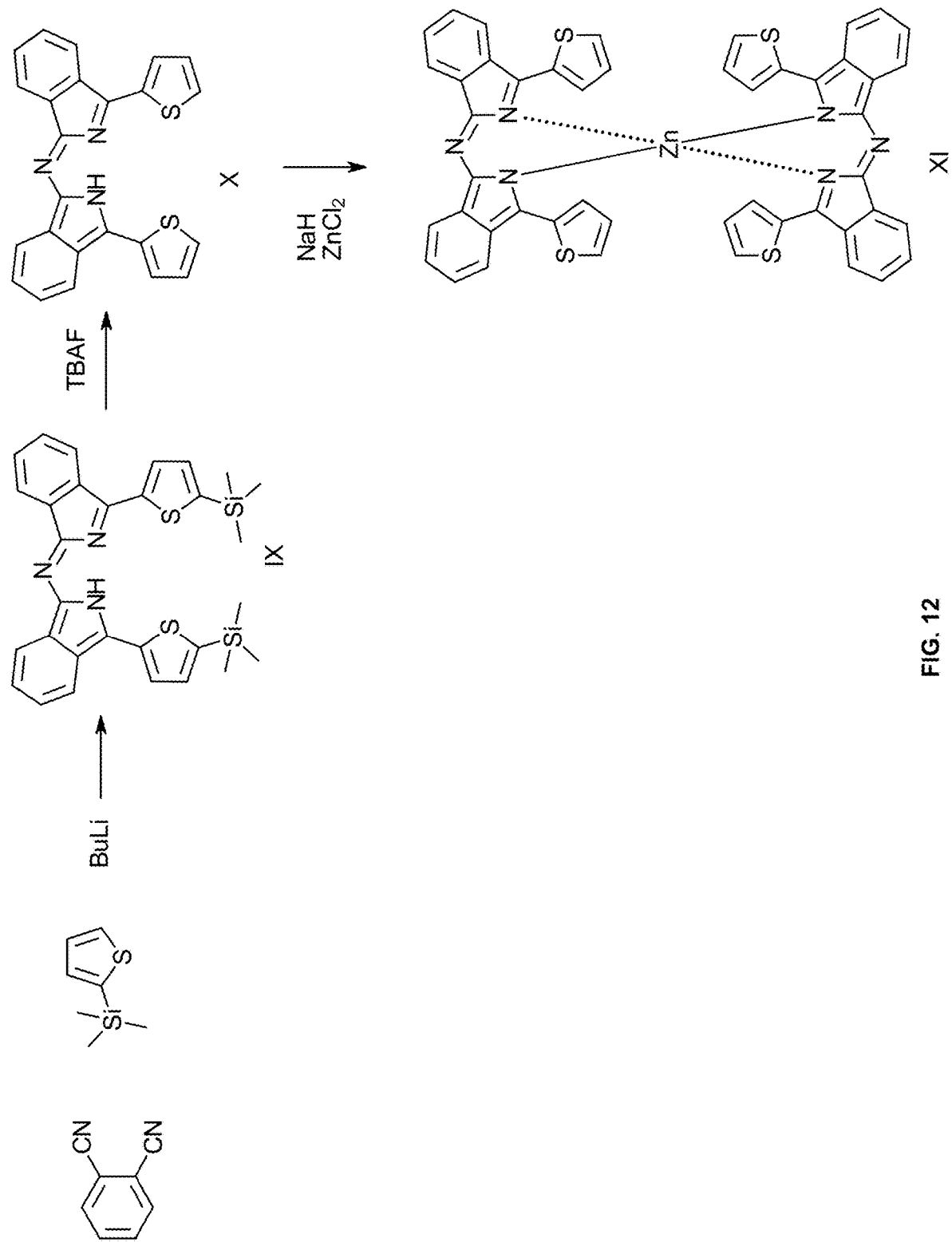
FIG. 12 provides a synthetic scheme for preparation of a fifth example metal coordinated compound.

FIG. 12 provides a synthetic scheme for preparation of an example metal coordinated compound:

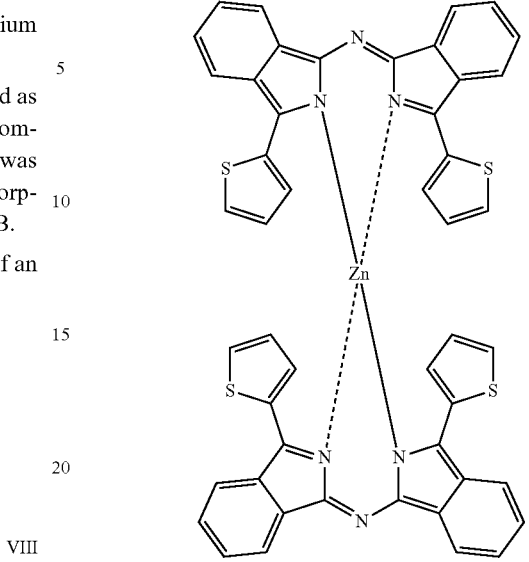

XI

Compound IX: In an oven dried 500 ml 3-neck round bottom flask equipped with Schlenk line, n-butyllithium (70.2 ml, 2.5 M solution, 0.176 mmol) was added dropwise into the vigorously stirring anhydrous diethyl ether solution (150 ml) of 2-trimethylsilyl thiophene (27.4 g, 0.176 mmol) at −78° C. under nitrogen. The solution was allowed to warm to room temperature (around 20° C.) and stirred for another 2 h. In a different oven dried 1 L 3-neck round bottom flask equipped with mechanical stirrer, addition funnel, and temperature probe phthalonitrile (15 g, 0.117 mmol) was suspended in dry toluene (300 ml) under nitrogen and the reaction temperature was adjusted to <−70° C. The addition funnel was charged with organolithium reagent using cannula and added dropwise to the reaction mixture with stirring over 45-60 min keeping reaction temp under −65° C. With addition of organolithium reagent, the reaction mixture gradually turned from white suspension to brown and then green. After complete addition the reaction mixture gets darker. The system was allowed to warm up to room temperature and stirred for another 3 h. The reaction was quenched by adding 20% aqueous $NH_4Cl$ (100 ml) keeping reaction temp under 5° C. Additional water (100 ml) was added and the mixture was steam distilled over 4 hrs. Dark colored precipitate was washed with hot water, filtered, washed with MeOH/Water (2:1) until the washing was colorless. The crude material was stirred with hot (50° C., 250 ml) IPA for 2 h, filtered while hot and washed with IPA until the washing was almost colorless. The solid obtained was dried under high vacuum and was characterized as compound IX (5.6 g, 17.3%).

Compound X: In an oven dried 500 ml 3-neck round bottom flask, compound IX (2.56 g, 5 mmol) was dissolved in anhydrous DCM (200 ml) under nitrogen, followed by dropwise addition of tetrabutylammonium fluoride (TBAF, 36.1 ml of 1 M solution, 37 mmol) and stirred at room temperature. There was no change in reaction temperature or color during addition. LC-MS after 16 h showed complete conversion to desired product. The reaction was quenched by adding water (200 ml). Shiny copper colored precipitate was filtered, washed with hot water and dried under high vacuum to get compound X (1.6 g, 89%).

Compound XI: Compound XI was synthesized using the same method as described for preparing compound II, substituting compound X in place of compound I. Compound XI was sublimed in 54% yield. Solution (dichloromethane) and film absorption spectra of compound XI is provided in FIG. 15A and FIG. 16, respectively.

Figure 13:
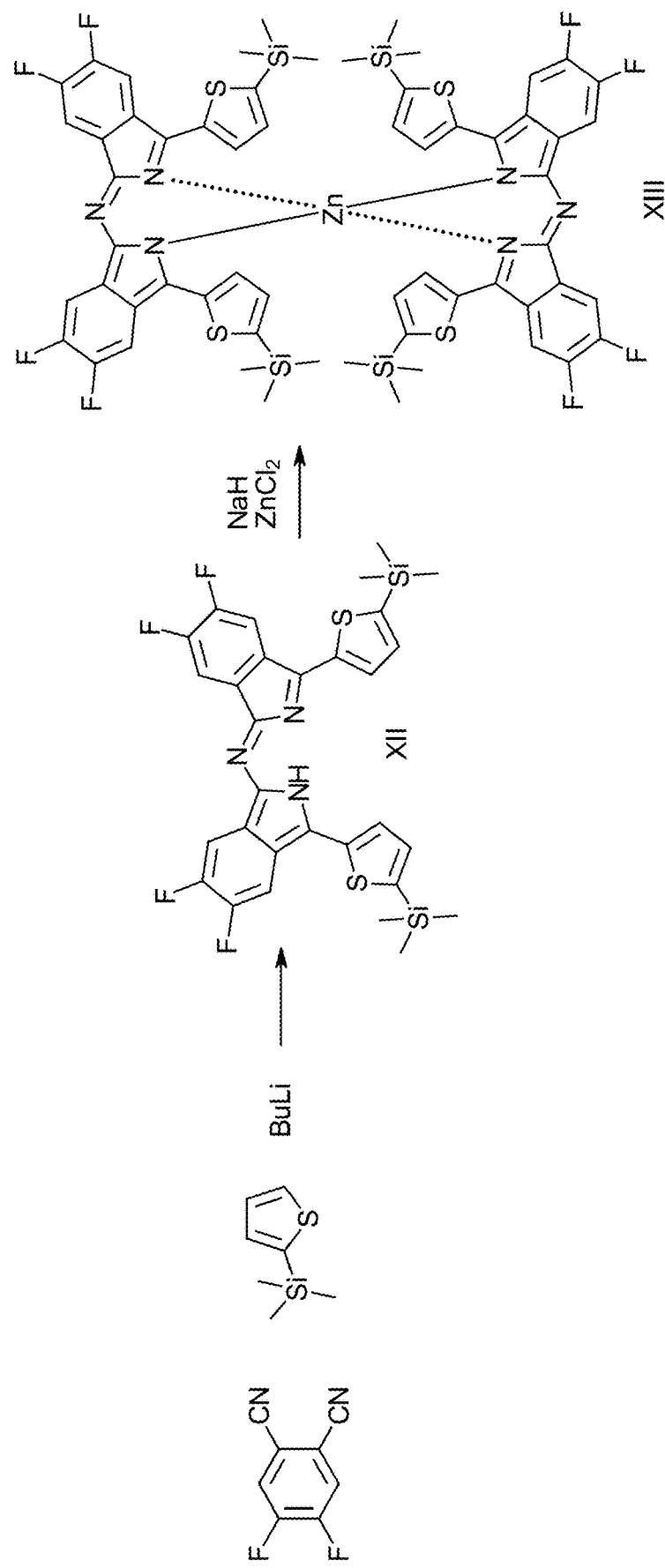
FIG. 13 provides a synthetic scheme for preparation of a sixth example metal coordinated compound.

FIG. 13 provides a synthetic scheme for preparation of an example metal coordinated compound:

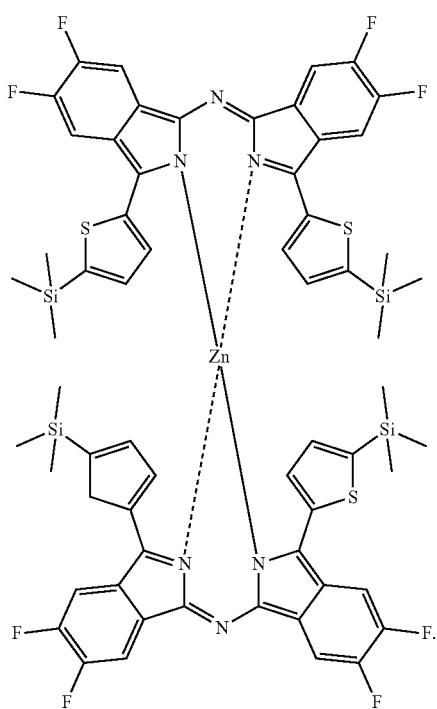

XIII

Compound XII: Compound XII was synthesized using the same method as described for preparing compound IX, substituting 4,5-difluorophthalonitrile in place of phthalonitrile. Compound XII was obtained in 9% yield.

Compound XIII: Compound XIII was synthesized using the same method as described for preparing compound II, substituting compound XII in place of compound I. Compound XIII was obtained in 72% yield. Compound XIII was sublimed in 80% yield. Solution (dichloromethane) and film absorption spectra of compound XIII is provided in FIG. 15A and FIG. 16, respectively.

Figure 14:
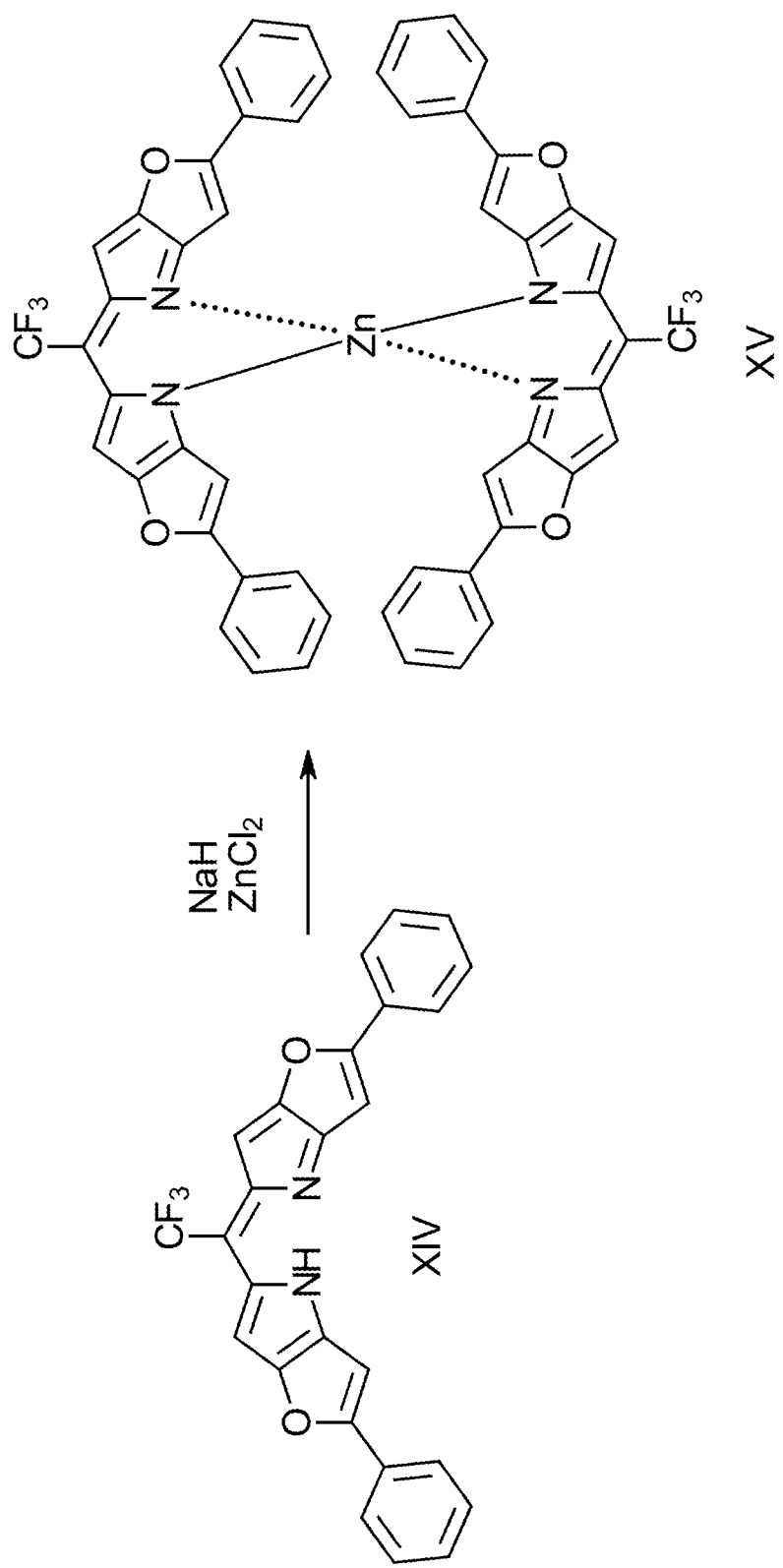
FIG. 14 provides a synthetic scheme for preparation of a seventh example metal coordinated compound.

FIG. 14 provides a synthetic scheme for preparation of an example metal coordinated compound:

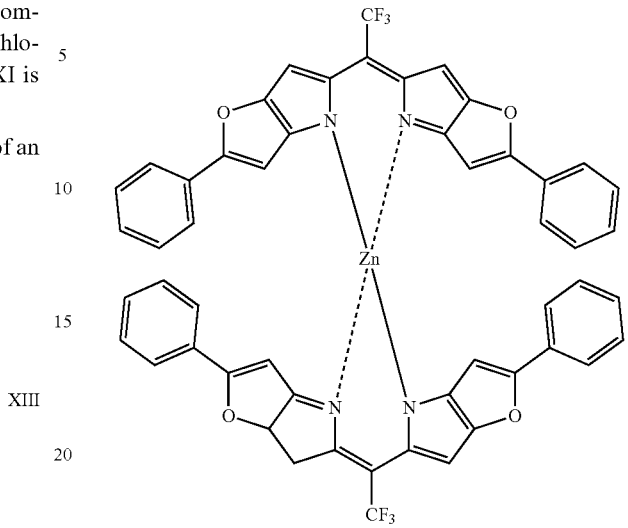

XV

Compound XV: Compound XIV was synthesized using method reported in Li et al. Journal of American Chemical Society 2017, 139, 13636. Compound XV was synthesized using the same method as described for preparing compound II, substituting compound XIV in place of compound I. Compound XV was obtained in 96% yield. A solution (dichloromethane) absorption spectrum of compound XV is provided in FIG. 15B.

Figure 17A:
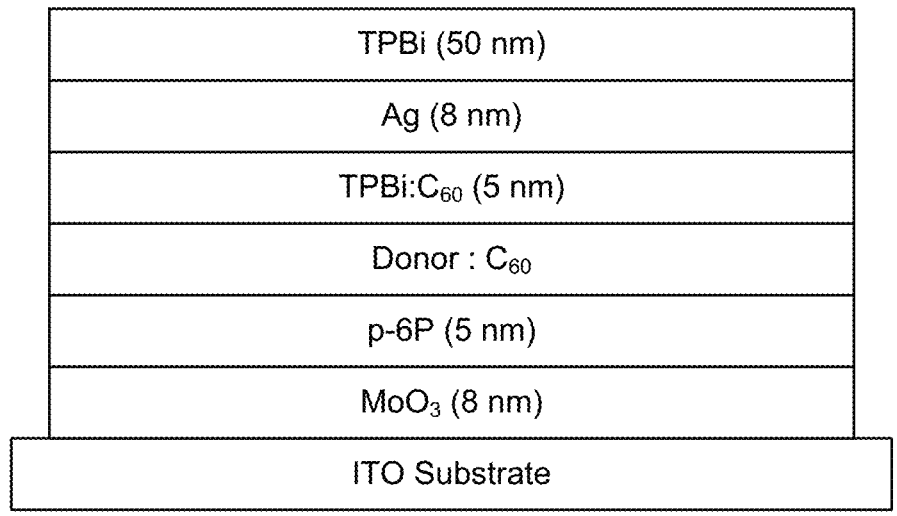
FIG. 17A provides a schematic depiction of a device stack configuration for example photovoltaic devices incorporating a metal coordinated compound.
Figure 17B:
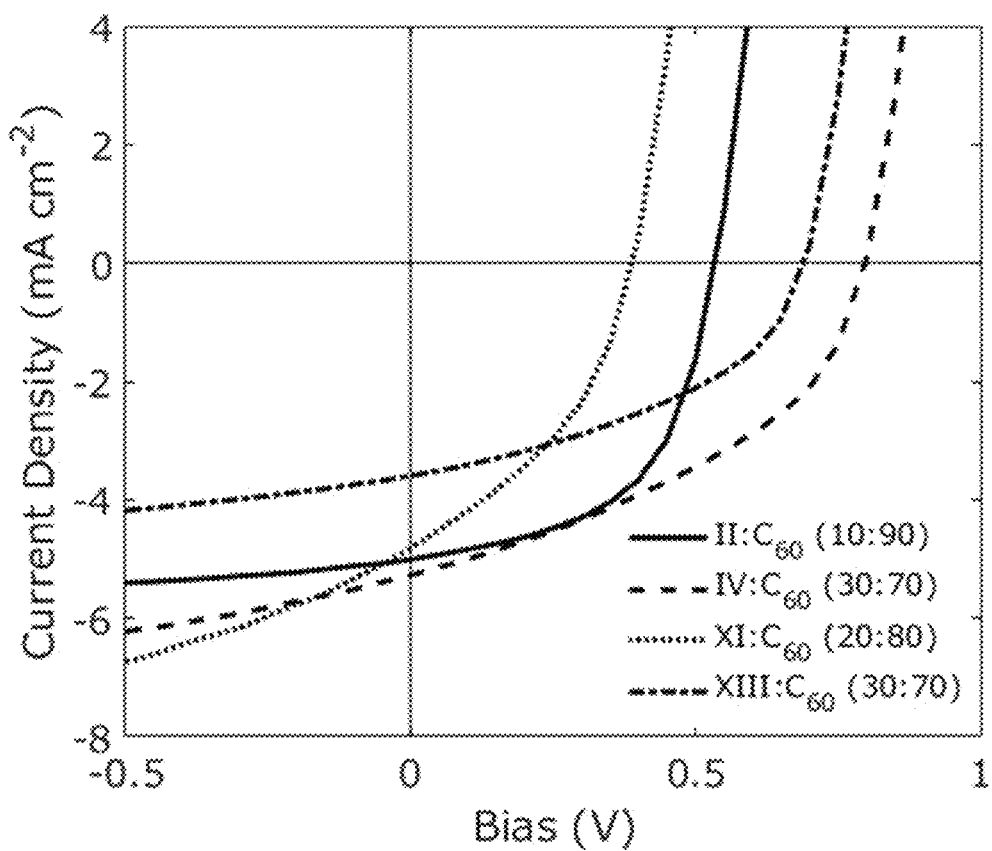
FIG. 17B provides current-voltage (J-V) curves for four photovoltaic devices incorporating different metal coordinated compounds.
Figure 17C:
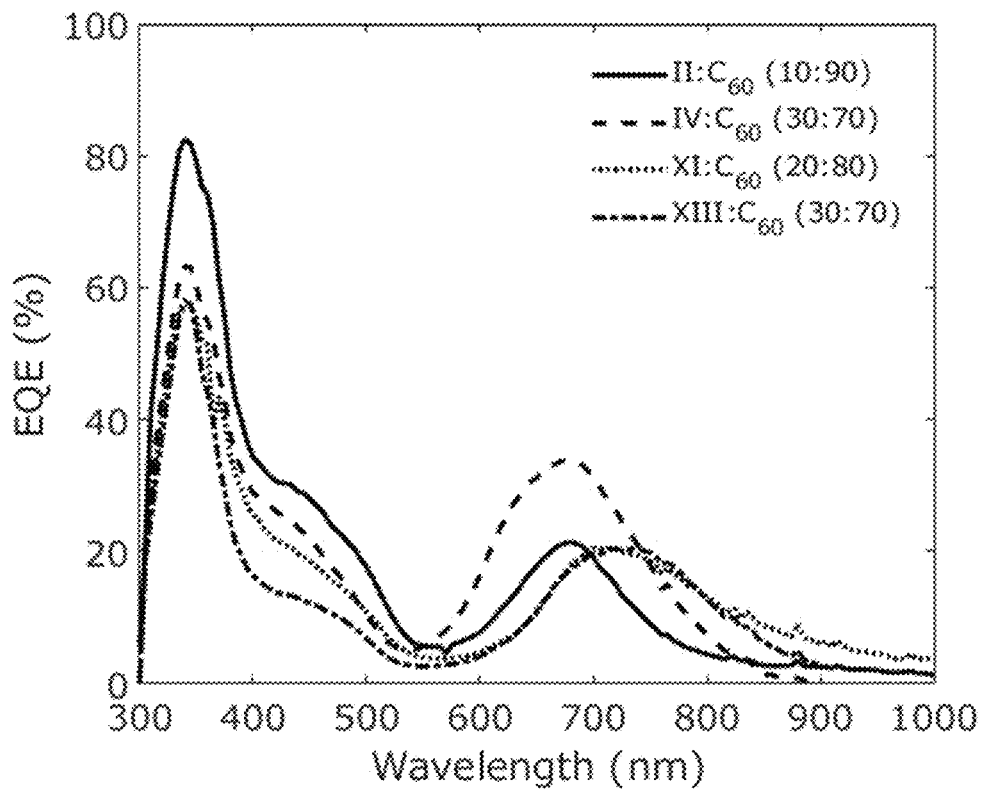
FIG. 17C provides external quantum efficiency (EQE) spectra for four photovoltaic devices incorporating different metal coordinated compounds.
Figure 17D:
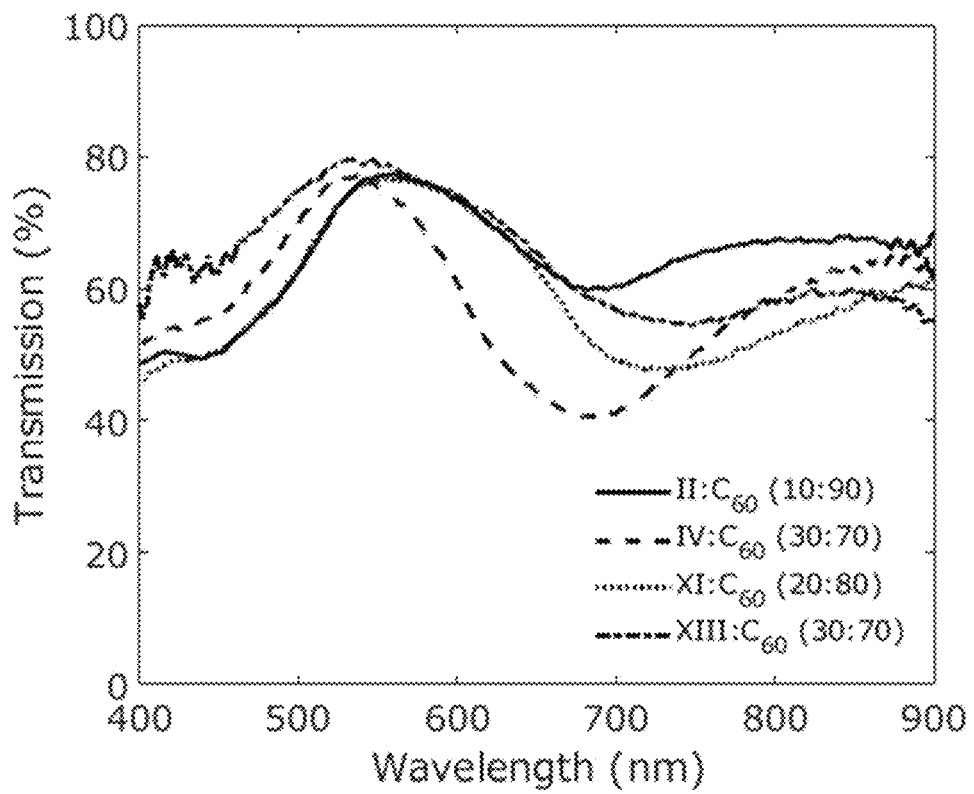
FIG. 17D provides transmission spectra for four photovoltaic devices incorporating different metal coordinated compounds.

Example 2—Photovoltaic Devices Incorporating Metal Coordinated Photoactive Compounds Compounds II, IV, XI, and XIII were incorporated into a transparent photovoltaic device stack as illustrated in FIG. 17A. Each compound was used as an electron donor and mixed in a bulk heterojunction with $C_{60}$ as the electron acceptor. All device layers were deposited via vacuum thermal evaporation under high vacuum conditions (~$10^{-7}$ Torr). Devices comprising compounds II, IV, and XI as donors employed a blend thickness of 60 nm, while devices with compound XIII as a donor employed a thinner blend of 30 nm. FIG. 17B provides the current density-voltage curves for the devices in FIG. 17A as measured under simulated AM1.5G. Devices exhibit clear rectification, photocurrent, and photovoltage production for all four compounds. FIG. 17C and FIG. 17D, respectively, provide the corresponding external quantum efficiency (EQE) and transmission spectra for the devices described in FIG. 17A. Clear contributions to both the EQE and transmission spectra can be seen due to absorption of compounds II, IV, XI, and XIII in the near-infrared wavelengths.

Table 1 provides the measured photovoltaic parameters and average visible transmittance for the devices. Listed are the short-circuit current density ($J_{sc}$), open-circuit voltage ($V_{oc}$), fill factor (FF), power conversion efficiency (PCE), and average visible transmittance ($T_{vis}$) for the devices in FIG. 17A.

TABLE 1

| Donor | $J_{sc}$ (mA cm$^2$) | Voc (V) | FF | PCE (%) | $T_{vis}$ (%) |
|---|---|---|---|---|---|
| II | 5.01 | 0.53 | 0.55 | 1.50 | 71.4 |
| IV | 5.28 | 0.80 | 0.42 | 1.73 | 68.2 |
| XI | 4.82 | 0.39 | 0.40 | 0.76 | 71.1 |
| XIII | 3.60 | 0.69 | 0.43 | 1.05 | 75.4 |

STATEMENTS REGARDING INCORPORATION BY REFERENCE AND VARIATIONS

All references throughout this disclosure, for example patent documents including issued or granted patents or equivalents; patent application publications; and non-patent literature documents or other source material; are hereby incorporated by reference herein in their entireties, as though individually incorporated by reference.

All patents and publications mentioned in this disclosure are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups and classes that can be formed using the substituents are disclosed separately. When a Markush group or other grouping is used herein, all individual members of the group and all combinations and subcombinations possible of the group are intended to be individually included in the disclosure. As used herein, "and/or" means that one, all, or any combination of items in a list separated by "and/or" are included in the list; for example "1, 2 and/or 3" is equivalent to "'1' or '2' or '3' or '1 and 2' or '1 and 3' or '2 and 3' or '1, 2 and 3'".

Every formulation or combination of components described or exemplified can be used to practice the invention, unless otherwise stated. Specific names of materials are intended to be exemplary, as it is known that one of skill in the art can name the same material differently. It will be appreciated that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this disclosure. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

Abbreviations that may be utilized in the present specification include:
TPBi: 2,2',2"-(1,3,5-Benzinetriyl)-tris(1-phenyl-1-H-benzimidazole)
$C_{60}$: Fullerene-$C_{60}$
p-6P: Para-sexiphenyl The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered within the scope of this disclosure as defined by the appended claims.

What is claimed is:

1. A photoactive compound having the formula:

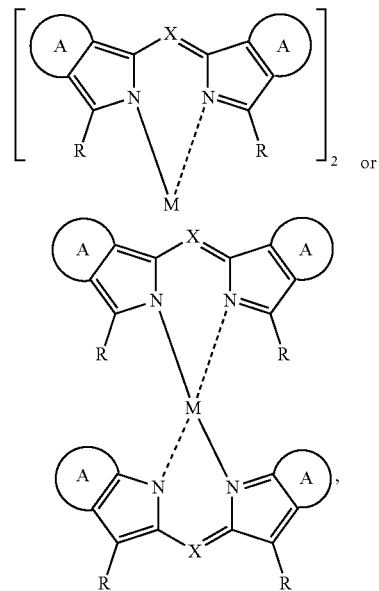

wherein X is N or C-R, wherein M is a metal atom with a stable +2 oxidation state, wherein each R is independently H, F, Cl, Br, I, $CF_3$, CN, a substituted silyl group, a substituted or unsubstituted alkyl group, a substituted or unsubstituted alkenyl group, a substituted or unsubstituted alkynyl group, a substituted or unsubstituted alkoxy group, a substituted or unsubstituted 5-membered ring, a substituted or unsubstituted 5-membered heterocyclic ring, a substituted or unsubstituted 6-membered ring, a substituted or unsubstituted 6-membered heterocyclic ring, or a substituted or unsubstituted fused ring, wherein at least one R comprises

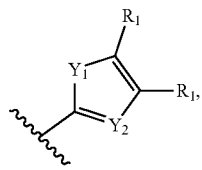

wherein $Y_1$ and $Y_2$ are independently selected from CH, NH, alkyl substituted N, alkyl substituted Si, O, S, Se, or Te, wherein each $R_1$ is independently H, F, Cl, Br, I, $CH_3$, $CF_3$, $C(CH_3)_3$, $CH(CH_3)_2$, $OCH_3$, $Si(CH_3)_3$, or $R_1$ and $R_1$ together form a 5-membered substituted or unsubstituted ring, or a 6-membered substituted or unsubstituted ring, and wherein each A ring independently comprises a 5-membered ring, a 6-membered ring, or a fused ring group including non-aromatic, aromatic, or heteroaromatic ring moieties.

2. The photoactive compound of claim 1, having a molecular weight of from 250 atomic mass units to 1500 atomic mass units.

3. The photoactive compound of claim 1, characterized by a sublimation purification yield by mass of 20% or greater.

4. The photoactive compound of claim 1, having a thermal decomposition temperature of from 200° C. to 500° C.

5. The photoactive compound of claim 1, exhibiting a bandgap of 0.5 eV to 4.0 eV.

6. The photoactive compound of claim 1, exhibiting a sublimation temperature of from 150° C. to 450° C. at pressures of from 0.2 Torr to $10^{-7}$ Torr.

7. The photoactive compound of claim 1, wherein M is Zn, Co, Cu, Ni, Fe, Pb, Mg, Mn, Pd, Pt, or Sn.

8. The photoactive compound of claim 1, wherein at least

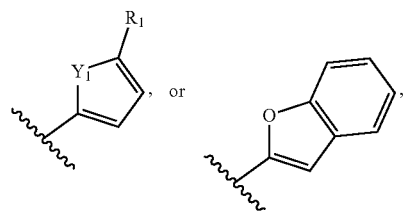

one R is F, Cl, Br, I, $CH_3$, $CF_3$, $C(CH_3)_3$, $CH(CH_3)_2$, $OCH_3$, $Si(CH_3)_3$, wherein $Y_1$ is NH, alkyl substituted N, alkyl substituted Si, O, or S.

9. The photoactive compound of claim 1, having a formula of

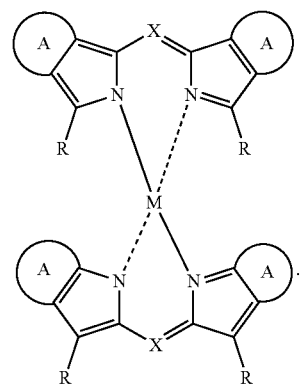

10. The photoactive compound of claim 1, having a formula of:

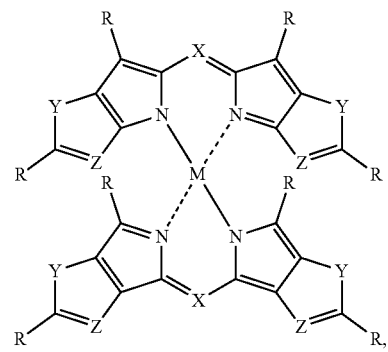

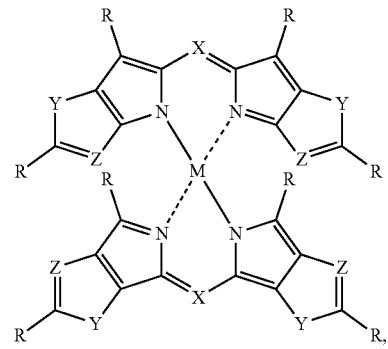

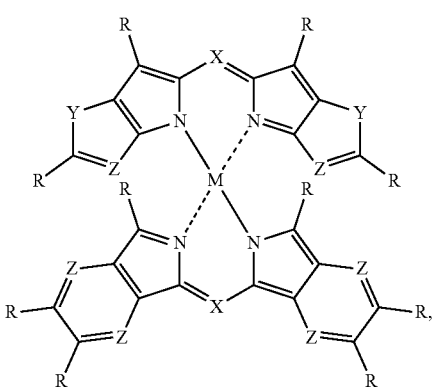

121
-continued
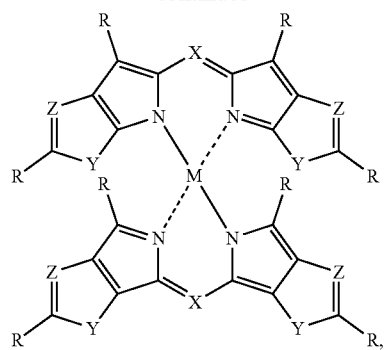
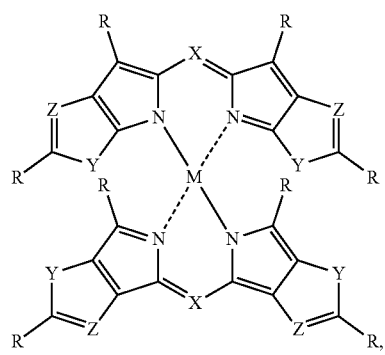
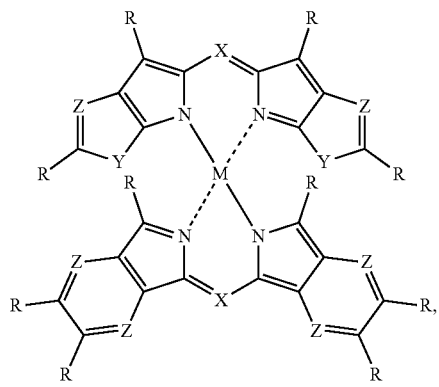
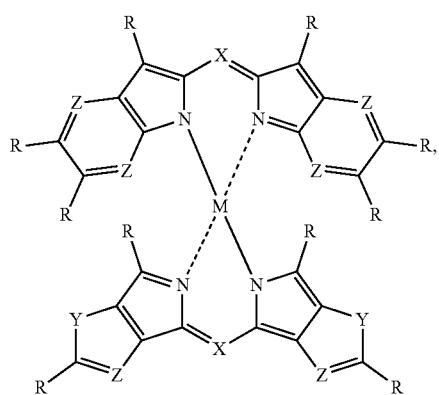
122
-continued
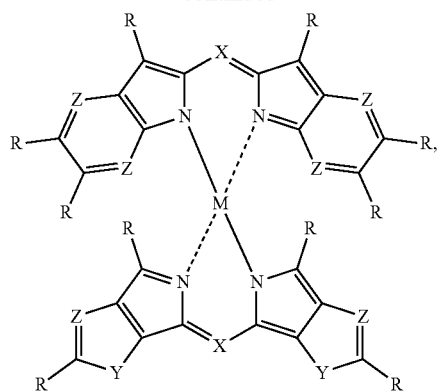
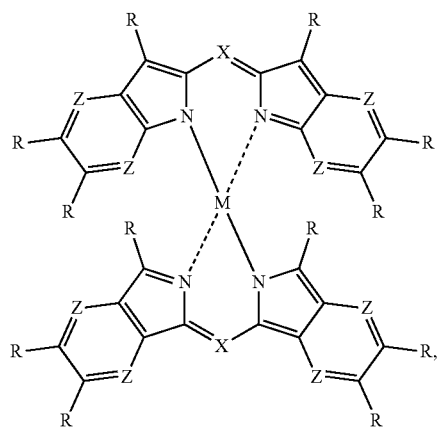
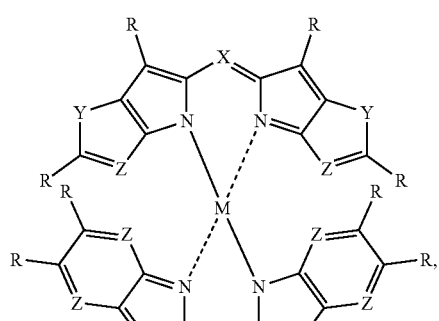
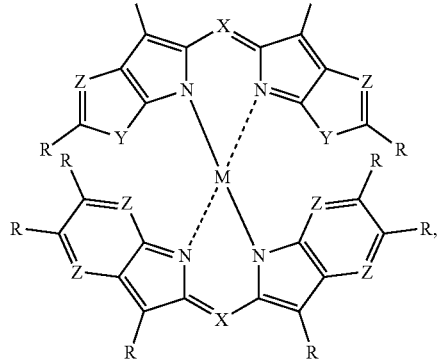

-continued
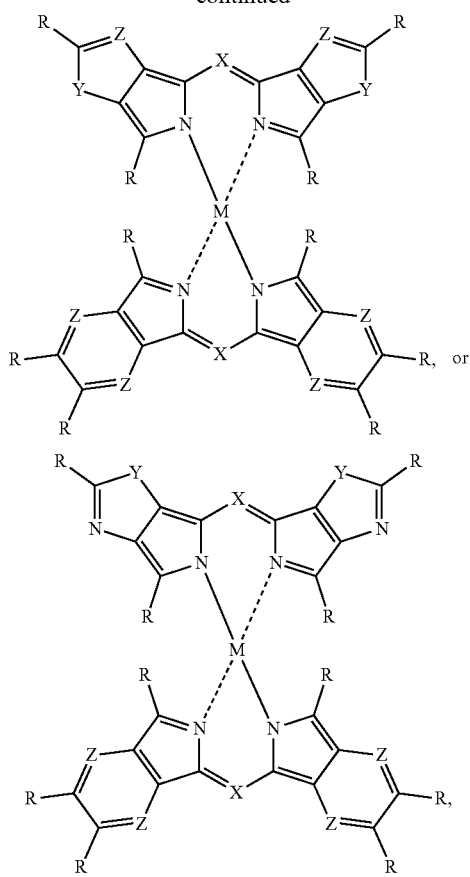
wherein each X is N or C-R, wherein each Y is independently C-R, O, N, alkyl substituted N, alkyl substituted Si, S, Se, or Te, and wherein each Z is independently C-R or N.
11. The photoactive compound of claim 1, having a formula of:
-continued
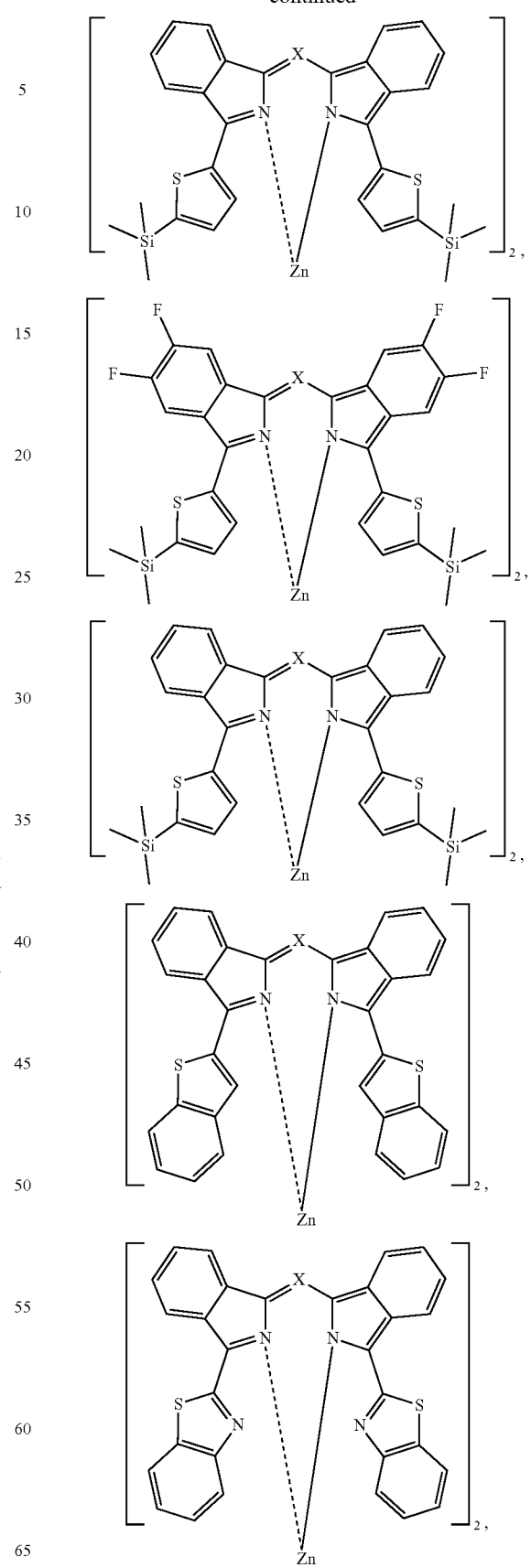

125
-continued
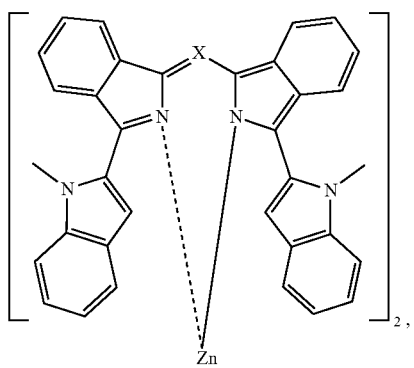
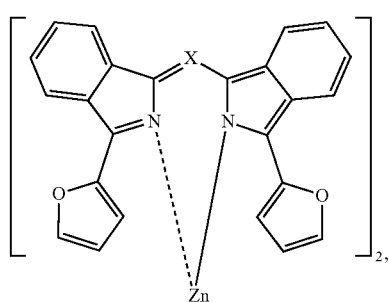
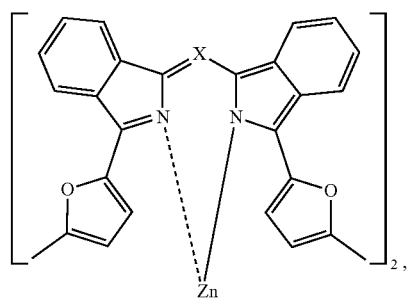
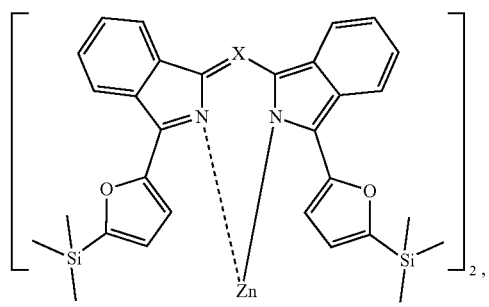
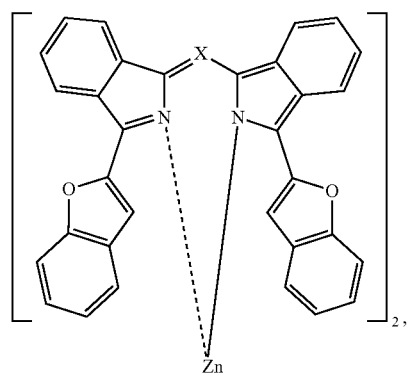
126
-continued
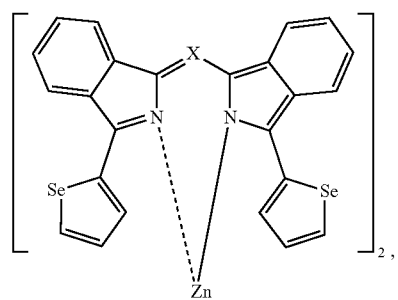
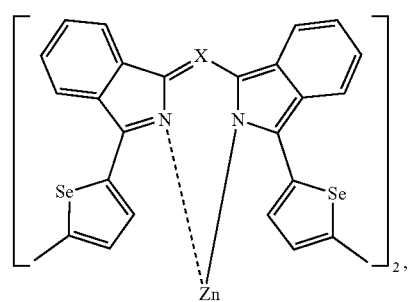
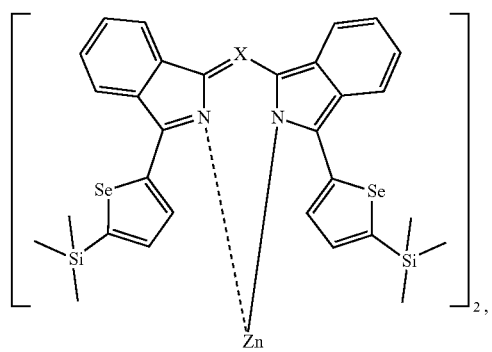
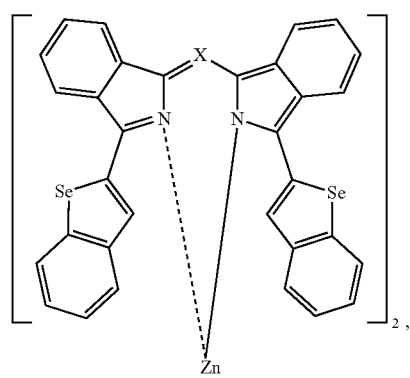

127
-continued
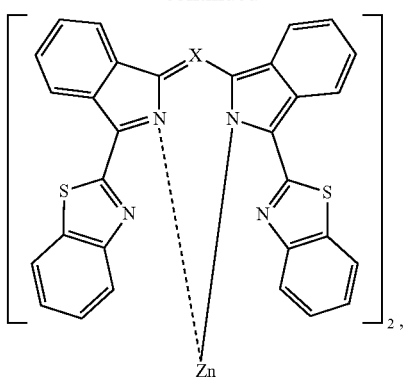
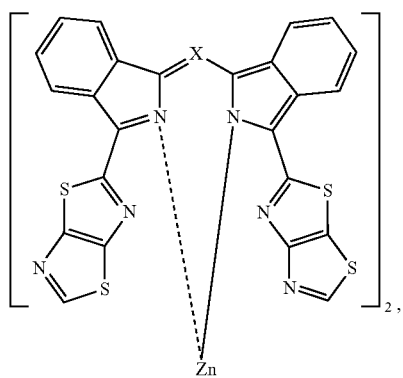
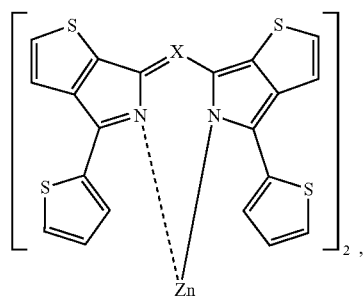
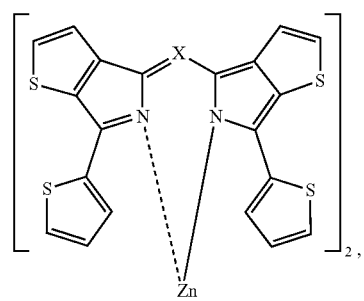
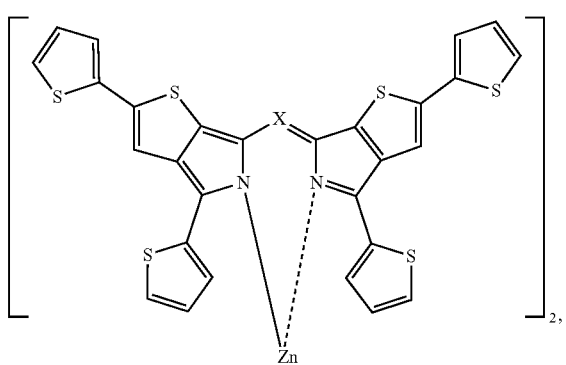
128
-continued
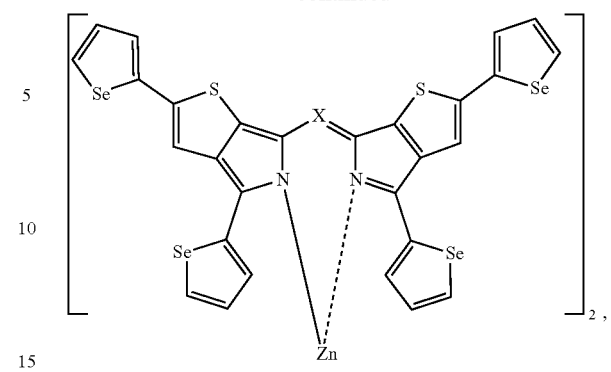
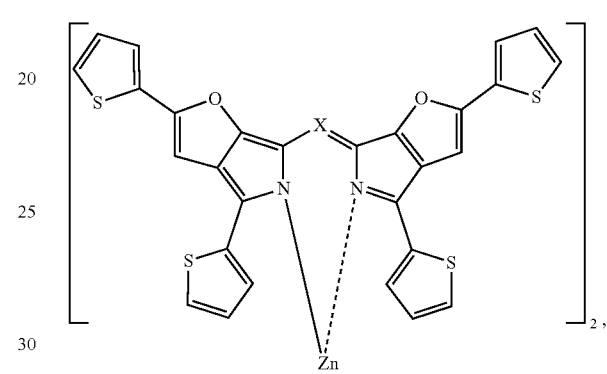
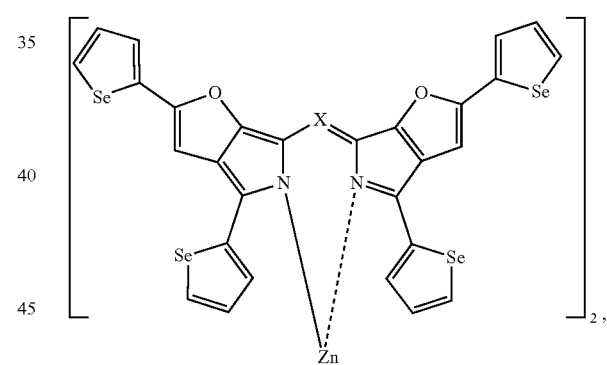
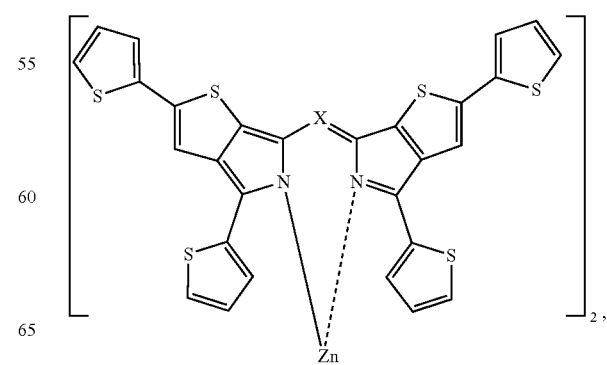

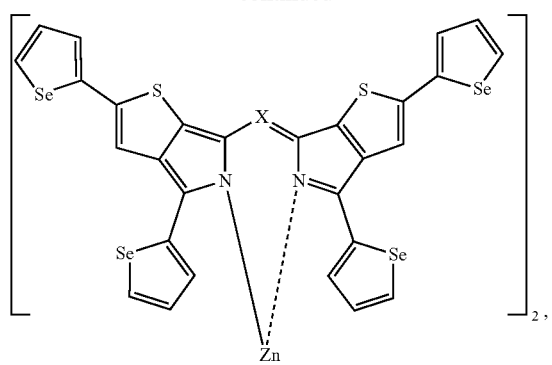
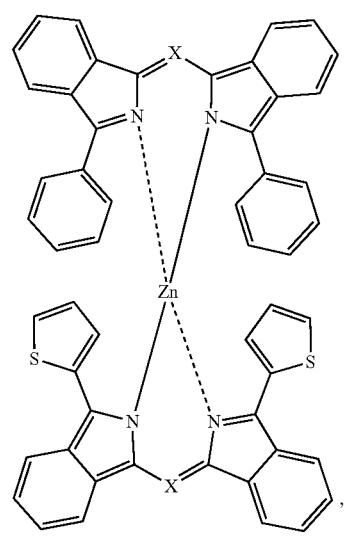
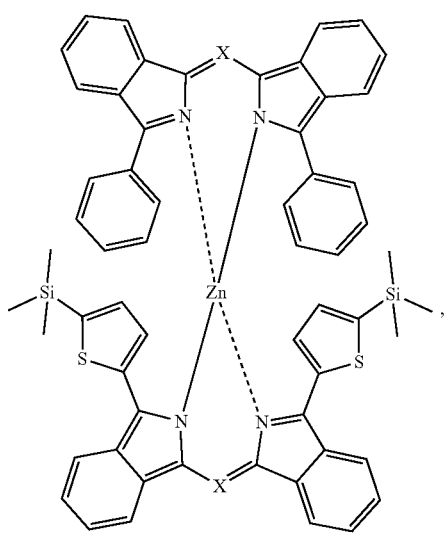
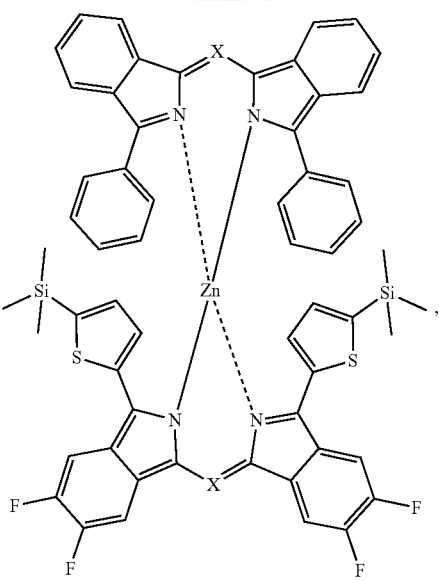
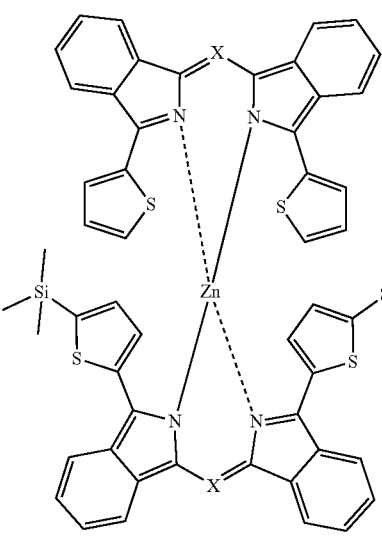
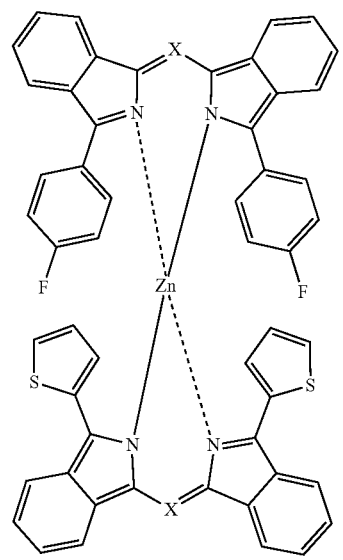

131
-continued
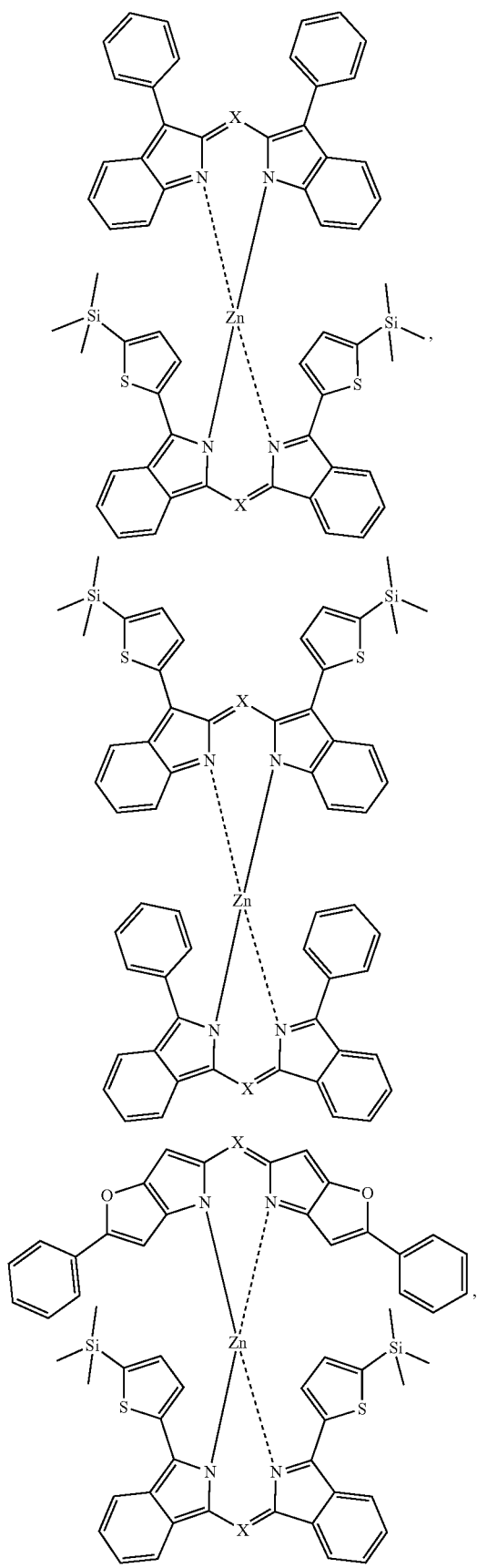
132
-continued
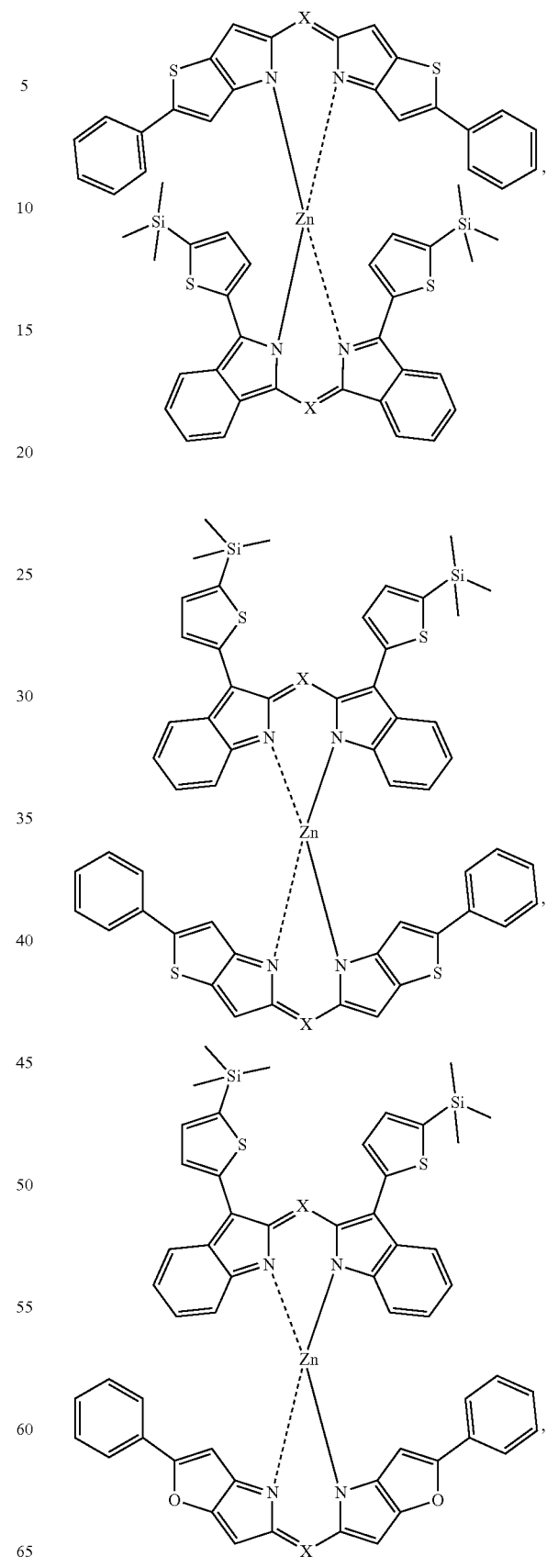

-continued

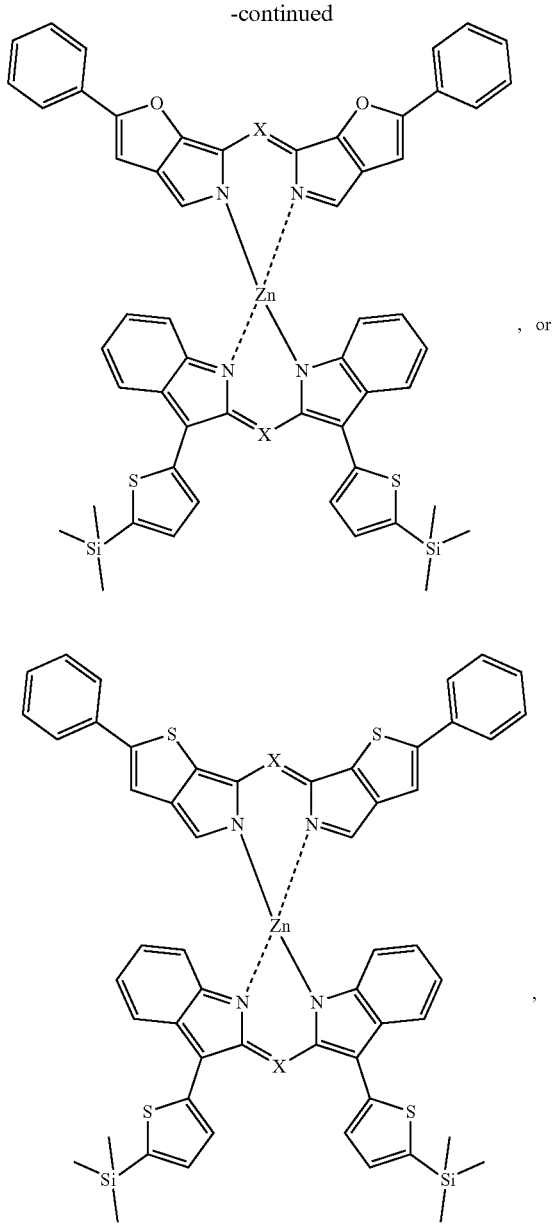

, or wherein X is N, CH, C-CF$_3$, or C-CN.

12. A photovoltaic device comprising:
a substrate;
a first electrode coupled to the substrate;
a second electrode above the first electrode;
a first photoactive layer between the first electrode and the second electrode, wherein the first photoactive layer comprises the photoactive compound of claim 1; and
a second photoactive layer between the first electrode and the second electrode, wherein the second photoactive layer comprises a counterpart electron donor material or a counterpart electron acceptor material, and wherein the first photoactive layer and the second photoactive layer correspond to separate photoactive layers, partially mixed photoactive layers, or a fully mixed photoactive layer.

13. The photovoltaic device of claim 12, wherein one or more or all of the substrate, the first electrode, the second electrode, the first photoactive layer, or the second photoactive layer is visibly transparent.

14. The photovoltaic device of claim 12, wherein one or more of the substrate, the first electrode, the second electrode, the first photoactive layer, or the second photoactive layer is partially transparent or opaque.

15. The photovoltaic device of claim 12, wherein the photoactive compound of claim 1 is an electron acceptor compound and wherein the second photoactive layer comprises a counterpart electron donor material.

16. The photovoltaic device of claim 12, wherein the photoactive compound of claim 1 is an electron donor compound and wherein the second photoactive layer comprises a counterpart electron acceptor material.

17. A method of making a photovoltaic device, the method comprising:
providing a substrate;
providing a first electrode coupled to the substrate;
depositing a photoactive layer over the first electrode and the substrate by a vapor deposition technique, the photoactive layer comprising the photoactive compound of claim 1; and
providing a second electrode over the photoactive layer.

18. The method of claim 17, wherein depositing the photoactive layer comprises depositing the photoactive compound using a thermal evaporation process.

19. The method of claim 17, wherein one or more or all of the substrate, the first electrode, the second electrode, or the photoactive layer is visibly transparent.

20. The method of claim 17, wherein one or more of the substrate, the first electrode, the second electrode, or the photoactive layer is partially transparent or opaque.

* * * * *